United States Patent
Peterson et al.

(10) Patent No.: US 9,486,447 B2
(45) Date of Patent: Nov. 8, 2016

(54) COMPOSITIONS AND METHODS FOR CONTROLLING NEURONAL EXCITATION

(75) Inventors: Randall Peterson, Belmont, MA (US); Chung Yan J. Cheung, Cupertino, CA (US); David Kokel, Somerville, MA (US)

(73) Assignee: The General Hospital Corporation, Boston, MA (US)

( * ) Notice: Subject to any disclaimer, the term of this patent is extended or adjusted under 35 U.S.C. 154(b) by 15 days.

(21) Appl. No.: 14/118,988

(22) PCT Filed: Jun. 13, 2012

(86) PCT No.: PCT/US2012/042151
§ 371 (c)(1),
(2), (4) Date: Mar. 26, 2014

(87) PCT Pub. No.: WO2012/174049
PCT Pub. Date: Dec. 20, 2012

(65) Prior Publication Data
US 2014/0330195 A1    Nov. 6, 2014

Related U.S. Application Data

(60) Provisional application No. 61/496,178, filed on Jun. 13, 2011.

(51) Int. Cl.
| | |
|---|---|
| A61K 31/4439 | (2006.01) |
| A61K 41/00 | (2006.01) |
| A61K 31/427 | (2006.01) |
| A61N 5/06 | (2006.01) |
| A61K 31/426 | (2006.01) |
| A61K 31/4406 | (2006.01) |

(52) U.S. Cl.
CPC ......... *A61K 31/4439* (2013.01); *A61K 31/426* (2013.01); *A61K 31/427* (2013.01); *A61K 31/4406* (2013.01); *A61K 41/00* (2013.01); *A61N 5/062* (2013.01); *A61N 5/0622* (2013.01); *A61N 2005/0661* (2013.01); *A61N 2005/0663* (2013.01)

(58) Field of Classification Search
None
See application file for complete search history.

(56) References Cited

U.S. PATENT DOCUMENTS

| | | | |
|---|---|---|---|
| 5,554,767 A | 9/1996 | Wang et al. | |
| 2005/0065577 A1* | 3/2005 | McArthur | A61N 5/0616 607/88 |
| 2005/0182293 A1* | 8/2005 | Katzman | A61B 18/24 600/108 |
| 2007/0162093 A1* | 7/2007 | Porter | A61N 5/0613 607/89 |
| 2010/0268288 A1 | 10/2010 | Hunter et al. | |

FOREIGN PATENT DOCUMENTS

RU    2072994 C1    2/1997

OTHER PUBLICATIONS

Brain et al., TRPV1 and TRPA1 channels in inflammatory pain: elucidating mechanisms, Ann N Y Acad Sci. 1245:36-7, (2011).

(Continued)

*Primary Examiner* — Adam M Weidner
(74) *Attorney, Agent, or Firm* — Nixon Peabody LLP

(57) ABSTRACT

Embodiments of the technology described herein relate, at least in part, to methods of modulating the activity of a neuron by contacting the neuron with a photo-sensitive TrpA1 agonist and then illuminating the neuron with electromagnetic radiation. Also described herein are photo-sensitive TrpA1 agonists.

15 Claims, 27 Drawing Sheets

(56) References Cited

OTHER PUBLICATIONS

Jordt et al., TRP channels in disease, Subcell Biochem, 45:253-71, (2007).
Kremeyer et al., A gain-of-function mutation in TRPA1 causes familial episodic pain syndrome, Neuron, 66 (5):671-80, (2010).
Mourot et al., "Rapid optical control of nociception with an ion-channel photoswitch", Nature Methods, 9 (4):396-402, (2012).
Scwartz et a., "Synergistic role of TRPV1 and TRPA1 in pancreatic pain and inflammation", Gastroenterology, 140(4):1283-1291.e1-2, (2011).
Bautista et al., PNAS, 102(34):12248-12252 (2012). "Pungent products from garlic activate the sensory ion channel TRPA1."
URL: http://www.ncbi.nlm.nih.gov/pmc/articles/PMC1189336/, abstract.
Rochkind et al., International Review of Neurobiology, 87:445-464 (2009). "Phototherapy in peripheral nerve injury: effects on muscle preservation and nerve regeneration."
Snyder et al., Lasers in Surgery and Medicine, 31(3):216-222 (2002). "Quantitation and calcitonin gene-related peptide mRNA and neuronal cell death in facial motor nuclei following axotomy and 633 nm low power laser treatment.".
Srikameswaran, Study looks at brain stimulation to give stroke recovery a boost. Pittsburgh Post-Gazette, 2006. URL: http://www.post-gazette.com/stories/news/health/study-looks-at-brain-stimulation-to-give-stroke-recovery-a-boost-460570/>.

* cited by examiner

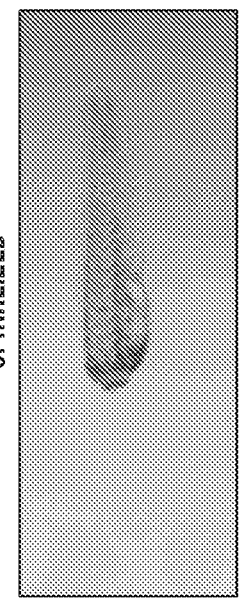
FIG. 10A
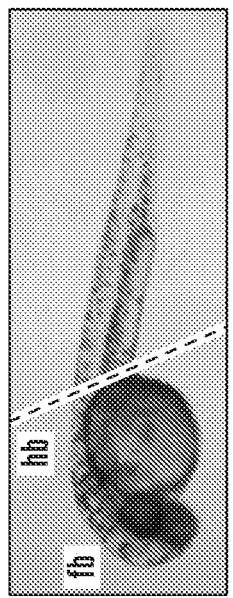
FIG. 10B
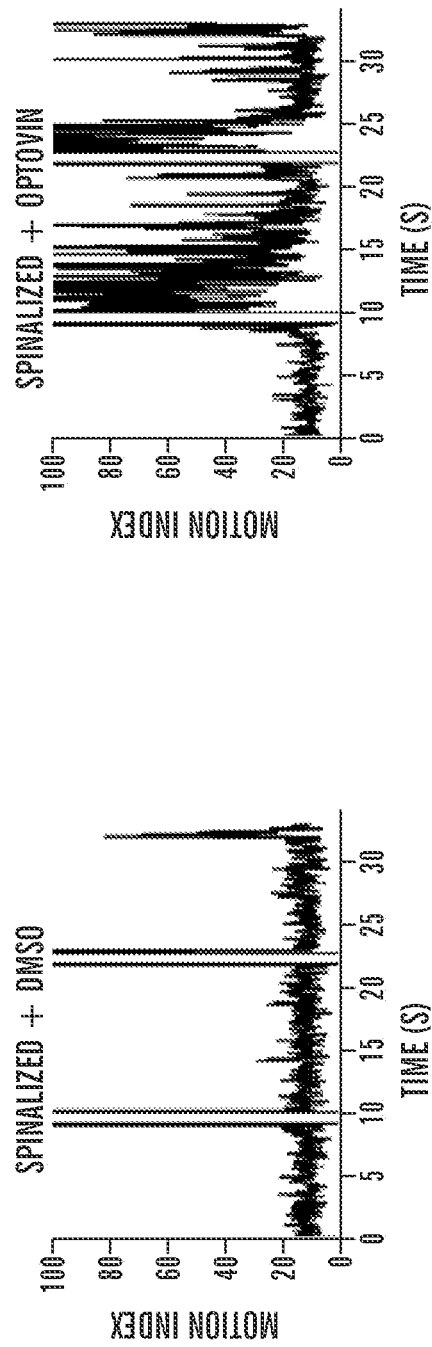
FIG. 10C
FIG. 10D

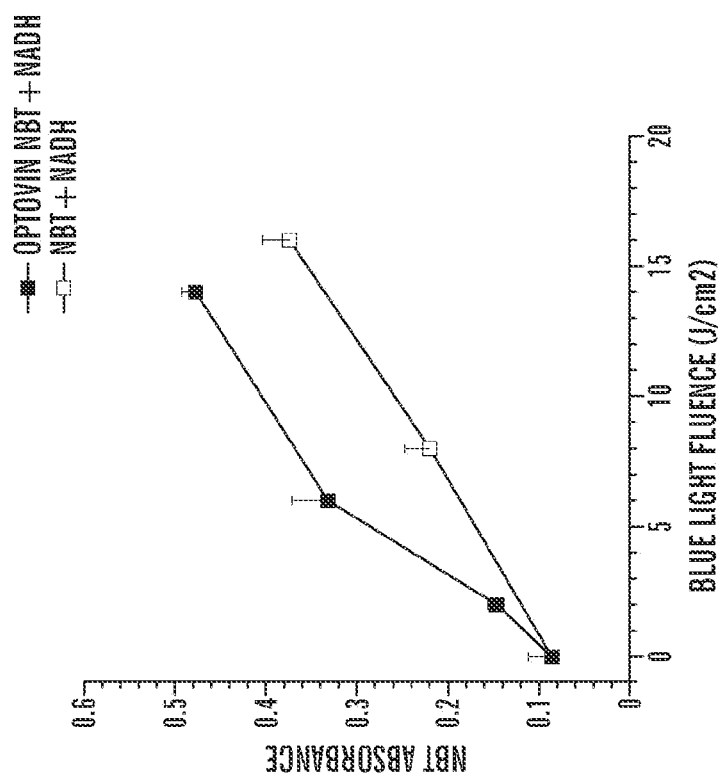
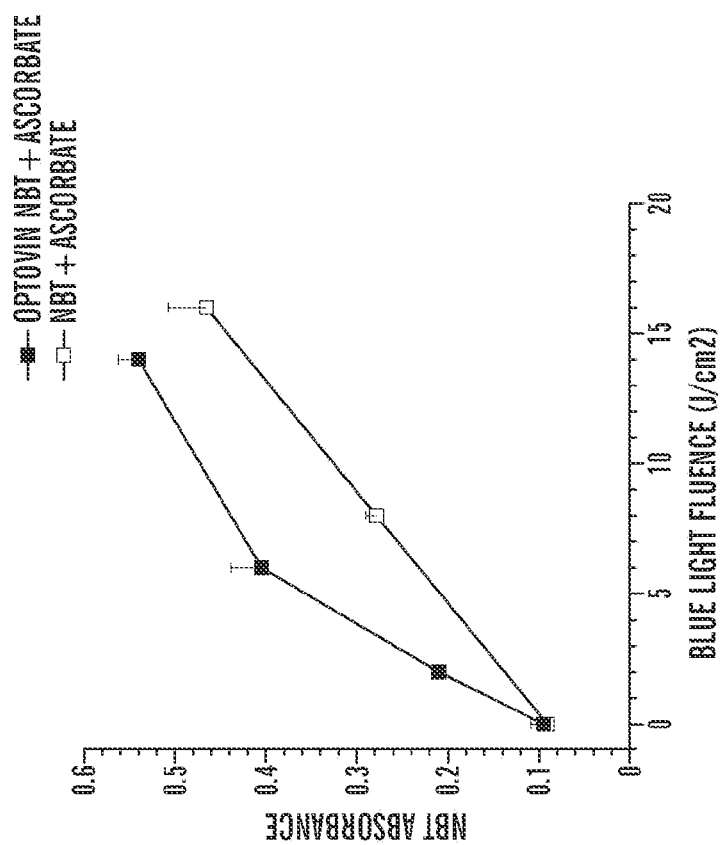
FIG. 14D
FIG. 14C

SEQUENCE LISTING

<160> NUMBER OF SEQ ID NOS: 2

<210> SEQ ID NO 1
<211> LENGTH: 1119
<212> TYPE: PRT
<213> ORGANISM: Homo sapiens

<400> SEQUENCE: 1

Met Lys Arg Ser Leu Arg Lys Met Trp Arg Pro Gly Glu Lys Lys Glu
1               5                   10                  15

Pro Gln Gly Val Val Tyr Glu Asp Val Pro Asp Asp Thr Glu Asp Phe
            20                  25                  30

Lys Glu Ser Leu Lys Val Val Phe Glu Gly Ser Ala Tyr Gly Leu Gln
        35                  40                  45

```
Asn Phe Asn Lys Gln Lys Lys Leu Lys Arg Cys Asp Asp Met Asp Thr
 50                  55                  60
Phe Phe Leu His Tyr Ala Ala Glu Gly Gln Ile Glu Leu Met Glu
 65                  70                  75                  80
Lys Ile Thr Arg Asp Ser Ser Leu Glu Val Leu His Glu Met Asp Asp
                 85                  90                  95
Tyr Gly Asn Thr Pro Leu His Cys Ala Val Glu Lys Asn Gln Ile Glu
                100                 105                 110
Ser Val Lys Phe Leu Leu Ser Arg Gly Ala Asn Pro Asn Leu Arg Asn
            115                 120                 125
Phe Asn Met Met Ala Pro Leu His Ile Ala Val Gln Gly Met Asn Asn
130                 135                 140
Glu Val Met Lys Val Leu Leu Glu His Arg Thr Ile Asp Val Asn Leu
145                 150                 155                 160
Glu Gly Glu Asn Gly Asn Thr Ala Val Ile Ile Ala Cys Thr Thr Asn
                165                 170                 175
Asn Ser Glu Ala Leu Gln Ile Leu Leu Lys Gly Ala Lys Pro Cys
            180                 185                 190
Lys Ser Asn Lys Trp Gly Cys Phe Pro Ile His Gln Ala Ala Phe Ser
            195                 200                 205
Gly Ser Lys Glu Cys Met Glu Ile Ile Leu Arg Phe Gly Glu Glu His
210                 215                 220
Gly Tyr Ser Arg Gln Leu His Ile Asn Phe Met Asn Asn Gly Lys Ala
225                 230                 235                 240
Thr Pro Leu His Leu Ala Val Gln Asn Gly Asp Leu Glu Met Ile Lys
                245                 250                 255
Met Cys Leu Asp Asn Gly Ala Gln Ile Asp Pro Val Glu Lys Gly Arg
                260                 265                 270
Cys Thr Ala Ile His Phe Ala Ala Thr Gln Gly Ala Thr Glu Ile Val
            275                 280                 285
Lys Leu Met Ile Ser Ser Tyr Ser Gly Ser Val Asp Ile Val Asn Thr
290                 295                 300
Thr Asp Gly Cys His Glu Thr Met Leu His Arg Ala Ser Leu Phe Asp
305                 310                 315                 320
His His Glu Leu Ala Asp Tyr Leu Ile Ser Val Gly Ala Asp Ile Asn
                325                 330                 335
Lys Ile Asp Ser Glu Gly Arg Ser Pro Leu Ile Leu Ala Thr Ala Ser
                340                 345                 350
Ala Ser Trp Asn Ile Val Asn Leu Leu Ser Lys Gly Ala Gln Val
            355                 360                 365
Asp Ile Lys Asp Asn Phe Gly Arg Asn Phe Leu His Leu Thr Val Gln
            370                 375                 380
Gln Pro Tyr Gly Leu Lys Asn Leu Arg Pro Glu Phe Met Gln Met Gln
385                 390                 395                 400
Gln Ile Lys Glu Leu Val Met Asp Glu Asp Asn Asp Gly Cys Thr Pro
                405                 410                 415
Leu His Tyr Ala Cys Arg Gln Gly Gly Pro Gly Ser Val Asn Asn Leu
                420                 425                 430
Leu Gly Phe Asn Val Ser Ile His Ser Lys Ser Lys Asp Lys Lys Ser
            435                 440                 445
Pro Leu His Phe Ala Ala Ser Tyr Gly Arg Ile Asn Thr Cys Gln Arg
450                 455                 460
Leu Leu Gln Asp Ile Ser Asp Thr Arg Leu Leu Asn Glu Gly Asp Leu
```

-continued

```
            465                 470                 475                 480
        His Gly Met Thr Pro Leu His Leu Ala Ala Lys Asn Gly His Asp Lys
                        485                 490                 495
        Val Val Gln Leu Leu Lys Lys Gly Ala Leu Phe Leu Ser Asp His
                    500                 505                 510
        Asn Gly Trp Thr Ala Leu His His Ala Ser Met Gly Gly Tyr Thr Gln
                    515                 520                 525
        Thr Met Lys Val Ile Leu Asp Thr Asn Leu Lys Cys Thr Asp Arg Leu
                530                 535                 540
        Asp Glu Asp Gly Asn Thr Ala Leu His Phe Ala Ala Arg Glu Gly His
        545                 550                 555                 560
        Ala Lys Ala Val Ala Leu Leu Leu Ser His Asn Ala Asp Ile Val Leu
                        565                 570                 575
        Asn Lys Gln Gln Ala Ser Phe Leu His Leu Ala Leu His Asn Lys Arg
                    580                 585                 590
        Lys Glu Val Val Leu Thr Ile Ile Arg Ser Lys Arg Trp Asp Glu Cys
                595                 600                 605
        Leu Lys Ile Phe Ser His Asn Ser Pro Gly Asn Lys Cys Pro Ile Thr
                610                 615                 620
        Glu Met Ile Glu Tyr Leu Pro Glu Cys Met Lys Val Leu Leu Asp Phe
        625                 630                 635                 640
        Cys Met Leu His Ser Thr Glu Asp Lys Ser Cys Arg Asp Tyr Tyr Ile
                        645                 650                 655
        Glu Tyr Asn Phe Lys Tyr Leu Gln Cys Pro Leu Glu Phe Thr Lys Lys
                    660                 665                 670
        Thr Pro Thr Gln Asp Val Ile Tyr Glu Pro Leu Thr Ala Leu Asn Ala
                    675                 680                 685
        Met Val Gln Asn Asn Arg Ile Glu Leu Leu Asn His Pro Val Cys Lys
                690                 695                 700
        Glu Tyr Leu Leu Met Lys Trp Leu Ala Tyr Gly Phe Arg Ala His Met
        705                 710                 715                 720
        Met Asn Leu Gly Ser Tyr Cys Leu Gly Leu Ile Pro Met Thr Ile Leu
                        725                 730                 735
        Val Val Asn Ile Lys Pro Gly Met Ala Phe Asn Ser Thr Gly Ile Ile
                    740                 745                 750
        Asn Glu Thr Ser Asp His Ser Glu Ile Leu Asp Thr Thr Asn Ser Tyr
                    755                 760                 765
        Leu Ile Lys Thr Cys Met Ile Leu Val Phe Leu Ser Ser Ile Phe Gly
                770                 775                 780
        Tyr Cys Lys Glu Ala Gly Gln Ile Phe Gln Gln Lys Arg Asn Tyr Phe
        785                 790                 795                 800
        Met Asp Ile Ser Asn Val Leu Glu Trp Ile Ile Tyr Thr Thr Gly Ile
                        805                 810                 815
        Ile Phe Val Leu Pro Leu Phe Val Glu Ile Pro Ala His Leu Gln Trp
                    820                 825                 830
        Gln Cys Gly Ala Ile Ala Val Tyr Phe Tyr Trp Met Asn Phe Leu Leu
                    835                 840                 845
        Tyr Leu Gln Arg Phe Glu Asn Cys Gly Ile Phe Ile Val Met Leu Glu
                850                 855                 860
        Val Ile Leu Lys Thr Leu Leu Arg Ser Thr Val Val Phe Ile Phe Leu
        865                 870                 875                 880
        Leu Leu Ala Phe Gly Leu Ser Phe Tyr Ile Leu Leu Asn Leu Gln Asp
                        885                 890                 895
```

```
Pro Phe Ser Ser Pro Leu Leu Ser Ile Ile Gln Thr Phe Ser Met Met
            900                 905                 910
Leu Gly Asp Ile Asn Tyr Arg Glu Ser Phe Leu Glu Pro Tyr Leu Arg
        915                 920                 925
Asn Glu Leu Ala His Pro Val Leu Ser Phe Ala Gln Leu Val Ser Phe
    930                 935                 940
Thr Ile Phe Val Pro Ile Val Leu Met Asn Leu Leu Ile Gly Leu Ala
945                 950                 955                 960
Val Gly Asp Ile Ala Glu Val Gln Lys His Ala Ser Leu Lys Arg Ile
                965                 970                 975
Ala Met Gln Val Glu Leu His Thr Ser Leu Glu Lys Lys Leu Pro Leu
            980                 985                 990
Trp Phe Leu Arg Lys Val Asp Gln Lys Ser Thr Ile Val Tyr Pro Asn
        995                1000                1005
Lys Pro Arg Ser Gly Gly Met Leu Phe His Ile Phe Cys Phe Leu
   1010                1015                1020
Phe Cys Thr Gly Glu Ile Arg Gln Glu Ile Pro Asn Ala Asp Lys
   1025                1030                1035
Ser Leu Glu Met Glu Ile Leu Lys Gln Lys Tyr Arg Leu Lys Asp
   1040                1045                1050
Leu Thr Phe Leu Leu Glu Lys Gln His Glu Leu Ile Lys Leu Ile
   1055                1060                1065
Ile Gln Lys Met Glu Ile Ile Ser Glu Thr Glu Asp Asp Asp Ser
   1070                1075                1080
His Cys Ser Phe Gln Asp Arg Phe Lys Lys Glu Gln Met Glu Gln
   1085                1090                1095
Arg Asn Ser Arg Trp Asn Thr Val Leu Arg Ala Val Lys Ala Lys
   1100                1105                1110
Thr His His Leu Glu Pro
   1115

<210> SEQ ID NO 2
<211> LENGTH: 5190
<212> TYPE: DNA
<213> ORGANISM: Homo sapiens

<400> SEQUENCE: 2
ccagaagttc tccagggctt ccgcagagcg acttttttcgc tgcctgtgag ctgcagcgcg      60
ggagagctcg ggctcgcgcg gaccccagcg cctggcaggc tgacagcgct ctctcgcccc    120
aggtgcccgc gcgcgtggtg agcagctgca ccaggtggcg tccggggtgg ggtcaatgaa    180
gcgcagcctg aggaagatgt ggcgccctgg agaaaagaag gagccccagg gcgttgtcta    240
tgaggatgtg ccggacgaca cggaggattt caaggaatcg cttaaggtgg ttttttgaagg    300 aagtgcatat ggattacaaa actttaataa gcaaaagaaa ttaaaaagat gtgacgatat    360
ggacaccttc ttcttgcatt atgctgcagc agaaggccaa attgagctaa tggagaagat    420
caccagagat tcctctttgg aagtgctgca tgaaatggat gattatggaa ataccctctct    480 gcattgtgct gtagaaaaaa accaaattga aagcgttaag tttcttctca gcagaggagc    540
aaacccaaat ctccgaaact tcaacatgat ggctcctctc cacatagctg tgcagggcat    600
gaataatgag gtgatgaagg tcttgcttga gcatagaact attgatgtta atttggaagg    660
agaaaatgga acacagctg tgatcattgc gtgcaccaca ataatagcg aagcattgca    720 gatttttgctt aaaaaaggag ctaagccatg taaatcaaat aaatggggat gtttccctat    780
```

```
tcaccaagct gcattttcag gttccaaaga atgcatggaa ataatactaa ggtttggtga    840
agagcatggg tacagtagac agttgcacat taactttatg aataatggga aagccacccc    900
tctccacctg gctgtgcaaa atggtgactt ggaaatgatc aaaatgtgcc tggacaatgg    960
tgcacaaata gacccagtgg agaagggaag gtgcacagcc attcattttg ctgccaccca   1020
gggagccact gagattgtta aactgatgat atcgtcctat tctggtagcg tggatattgt   1080
taacacaacc gatggatgtc atgagaccat gcttcacaga gcttcattgt ttgatcacca   1140
tgagctagca gactatttaa tttcagtggg agcagatatt aataagatcg attctgaagg   1200
acgctctcca cttatattag caactgcttc tgcatcttgg aatattgtaa atttgctact   1260
ctctaaaggt gcccaagtag acataaaaga taattttgga cgtaattttc tgcatttaac   1320
tgtacagcaa ccttatggat taaaaaatct gcgacctgaa tttatgcaga tgcaacagat   1380
caaagagctg gtaatggatg aagacaacga tgggtgtact cctctacatt atgcatgtag   1440
acaggggggc cctggttctg taaataacct acttggcttt aatgtgtcca ttcattccaa   1500
aagcaaagat aagaaatcac ctctgcattt tgcagccagt tatgggcgta tcaatacctg   1560
tcagaggctc ctacaagaca taagtgatac gaggcttctg aatgaaggtg accttcatgg   1620
aatgactcct ctccatctgg cagcaaagaa tggacatgat aaagtagttc agcttcttct   1680 gaaaaaggt gcattgtttc tcagtgacca caatggctgg acagctttgc atcatgcgtc   1740
catgggcggg tacactcaga ccatgaaggt cattcttgat actaatttga agtgcacaga   1800
tcgcctggat gaagacggga acactgcact tcactttgct gcaagggaag gccacgccaa   1860
agccgttgcg cttcttctga gccacaatgc tgacatagtc ctgaacaagc agcaggcctc   1920 cttttttgcac cttgcacttc acaataagag gaaggaggtt gttcttacga tcatcaggag   1980
caaaagatgg gatgaatgtc ttaagatttt cagtcataat tctccaggca ataaatgtcc   2040
aattacagaa atgatagaat acctccctga atgcatgaag gtacttttag atttctgcat   2100
gttgcattcc acagaagaca gtcctgccg agactattat atcgagtata atttcaaata   2160
tcttcaatgt ccattagaat tcaccaaaaa aacacctaca caggatgtta tatatgaacc   2220
gcttacagcc ctcaacgcaa tggtacaaaa taaccgcata gagcttctca atcatcctgt   2280
gtgtaaagaa tatttactca tgaaatggtt ggcttatgga tttagagctc atatgatgaa   2340
tttaggatct tactgtcttg gtctcatacc tatgaccatt ctcgttgtca atataaaacc   2400
aggaatggct ttcaactcaa ctggcatcat caatgaaact agtgatcatt cagaaatact   2460
agataccacg aattcatatc taataaaaac ttgtatgatt ttagtgtttt tatcaagtat   2520
atttgggtat tgcaaagaag cggggcaaat tttccaacag aaaaggaatt attttatgga   2580
tataagcaat gttcttgaat ggattatcta cacgacgggc atcattttg tgctgccctt   2640 gtttgttgaa ataccagctc atctgcagtg gcaatgtgga gcaattgctg tttacttcta   2700
ttggatgaat ttcttattgt atcttcaaag atttgaaaat tgtggaattt ttattgttat   2760
gttggaggta attttgaaaa ctttgttgag gtctacagtt gtatttatct tccttcttct   2820
ggcttttgga ctcagctttt acatcctcct gaatttacag gatcccttca gctctccatt   2880
gctttctata atccagacct tcagcatgat gctaggagat atcaattatc gagagtcctt   2940
cctagaacca tatctgagaa atgaattggc acatccagtt ctgtcctttg cacaacttgt   3000
ttccttcaca atatttgtcc caattgtcct catgaattta cttattggtt tggcagttgg   3060
cgacattgct gaggtccaga acatgcatc attgaagagg atagctatgc aggtggaact   3120
```

-continued

```
tcataccagc ttagagaaga agctgccact ttggtttcta cgcaaagtgg atcagaaatc      3180
caccatcgtg tatcccaaca aacccagatc tggtgggatg ttattccata tattctgttt      3240
tttattttgc actggggaaa taagacaaga aataccaaat gctgataaat ctttagaaat      3300
ggaaatatta aagcagaaat accggctgaa ggatcttact tttctcctgg aaaaacagca      3360
tgagctcatt aaactgatca ttcagaagat ggagatcatc tctgagacag aggatgatga      3420
tagccattgt tcttttcaag acaggtttaa gaaagagcag atggaacaaa ggaatagcag      3480
atggaatact gtgttgagag cagtcaaggc aaaaacacac catcttgagc cttagctcct      3540
cagaccttca gtgaggcttc taatgggggg tgcatgactt gctggttcta actttcaatt      3600
taaaaagagt gaggaagaag cagaatgatt cattttgctg cgtgtgaaat catggttcct      3660
gcatgctgta taaagtaaa ccatcttta tcctctattc atattttcta ccaatcacta       3720
tgtattgggg atatctttgc agatatgttc aaattggact ggactttgat gagatataat      3780
ctcattattt gaatgggtag aaaatgaatt tgctagaaca cacatttta atgaaaagaa       3840 gtaataaatg taactattaa gctaaaatgc aaatgtcagt actgaattcc tgcttgttaa      3900
ttacataata tgtgatgctc tagaaaatag tcacaagtat taataatgcc ttagatgata      3960
gtcttaaata ttaggttgag gtctacctaa cctaagctgc ttcctggaaa gcttcatgtt      4020
gaaagaacct atgggtggca ccatgtggac ttttctgtcc ctactgtgat gaatagcccc      4080
acccttcttg ctgtccccaa cacacctgat gtcactttga gccatatagt tgaagtacaa      4140
attaataggc cttatgatat gcacgaattt tactatagat aatatatgtt gtttctggtt      4200
ttgtttgcca atgagcataa taaatgtaaa acctatatag tatccctgtg attattgtat      4260
gagcctttgt ttgagatttg aaaacaacat ggctccatca catattccct tttttcttt       4320 gatgtctact caaatcatga attaatcaca tacctcatca ttaatctttt caaggtcctt      4380
ctattgtttt gtctgatttt ctccatcatc ctgattagca tgtttattcc ctcactaccc      4440
ccaggagata ttcactgtaa tgaatatgtc tttggctatg tatgtgtcct tgtgttatgt      4500
tgtacagtgt tgttttgagt ctgttattat ttacacagat gttattatgc tatagcttct      4560
atttctgttt ttgcttctta tttctcttat aattctcact tatttcctat tttttctact      4620
catttctatt tgttactcct ttttactgga catgatgttt acaagataca actgtgttac      4680
tgtattccat ctagtacggg gcctttggtg tggcttacta tttcattgtg tgcacccacc      4740
cacccaccac actggacttt tctagagatg gacagcttgg ttacctccac cttcctgcac      4800
tcattctcaa acatactgat gttcatacaa accagcagag tgctgaggga cgatatgtac      4860
tattacaaaa ccagacactt ttacattcat ggtccaacag atcacatggc ctagaggcaa      4920
tgttgcatat accttaatct ttgatatgaa taatatcttt gttctttata tttcttaaaa      4980
cagaaagggt ggaaaatcac tatacagaag caatatccaa agatctcctg atcataaaga      5040 caagggggtct tttcagtctt ccctctcctc aaaccttgtg tagcattgca caatatagat      5100
ctcagtcaac attcactgag tgccaagaat gtgagaaaca ctgtaccatg cctgtcatgc      5160
gaaatattta aataaacaga ttgtcttaca                                       5190
```

COMPOSITIONS AND METHODS FOR CONTROLLING NEURONAL EXCITATION

CROSS-REFERENCE TO RELATED APPLICATIONS

This application is a 35 U.S.C. §371 National Phase Entry Application of International Application No. PCT/US2012/042151 filed Jun. 13, 2012, which designates the U.S., and which claims benefit under 35 U.S.C. §119(e) of U.S. Provisional Application No. 61/496,178 filed Jun. 13, 2011, the contents of each of which are incorporated herein by reference in their entireties.

GOVERNMENT SUPPORT

This invention was made with federal funding under Grant Nos. K01MH091449, MH086867, MH085205, HL109004, and DA026982 awarded by the National Institutes of Health and Grant Nos. R01NS060725, R01NS067688, and F31NS068038 awarded by the National Institute of Neurological Disorders and Stroke. The U.S. government has certain rights in the invention.

TECHNICAL FIELD

The technology described herein relates to methods for modulating the activity of neurons using photo-sensitive compounds as described herein.

SEQUENCE LISTING

The instant application contains a Sequence Listing which has been submitted in ASCII format via EFS-Web and is hereby incorporated by reference in its entirety. Said ASCII copy, created on Nov. 13, 2013, is named 030258-071012-US_SL.txt and is 16,819 bytes in size.

BACKGROUND

The firing of neurons in specific temporal and spatial patterns underlies all the major functions of the nervous system. External stimuli are detected by the excitation of specific sensory neurons, enabling vision, hearing, touch, taste, and smell. Neuronal excitation also enables humans and other animals to move and interact with their environments. Therefore, methods for controlling neuronal excitation could be used to regulate sensation and motor control and to correct nervous system disorders including pain, inflammation, Parkinson's disease, neuron damage, epilepsy, depression, and others. In the clinic, manipulating neuronal activity has required the use of drugs which offer poor spatial and temporal control, and electrical stimulation, which requires placement of electrodes with attendant tissue damage and distortion (Henderson J M, et al., *Neurosurgery*. 2009 64:796-804).

Electromagnetic radiation (e.g. light) is a stimulus that can be controlled with high temporal and spatial resolution. If neuronal activity could be modulated by electromagnetic radiation, it would offer a powerful means of manipulating the nervous system for research and therapy. Indeed, one of the most influential recent innovations in neuroscience has been optogenetics, an approach in which neurons are rendered photosensitive by causing them to express electromagnetic radiation-activated bacterial opsins such as channelrhodopsin or halorhodopsin (Boyden E S, et al., *Nat Neurosci*. 2005 8:1263-8; Zemelman B V, et al., *Neuron*. 2002 33:15-22; Miesenbock G. *Science*. 2009 326:395-9).

Optogenetics has yielded remarkable new insights in cultured cells and in some model organisms, but its use is limited to systems that can be manipulated by transgenesis to express the bacterial opsins. Therefore, current optogenetic approaches are not applicable in the clinic as they do not provide a means to control endogenous neuronal proteins and neuronal signaling in non-transgenic animals with electromagnetic radiation.

Some optogenetics work has been performed with photorelease of caged glutamate, which provides optical control of glutamate receptors in brain slices. Azobenzene-containing photoswitchable ligands have also been designed to control glutamate receptors and potassium channels[6,7,16-23]. However, virtually all prior work in chemical optogenetics has been limited to cultured cells, tissue slices, and other ex vivo preparations because most existing techniques are not effective in vivo.

TRP channels are involved in diverse sensory systems including vision, taste, temperature and touch. TRPA1 signaling contributes to illnesses including neuropathic pain and chronic inflammation[25-28]. Precise control of TRPA1 channels may be useful for understanding and treating these disorders. However, currently available TRPA1 ligands like mustard oil and cinnamaldehyde provide imprecise spatiotemporal control of TRPA1 signaling.

SUMMARY

Embodiments of the present technology are based, at least in part, on the discovery that optovin, and related compounds, can function as photochemical switch compounds with potent bioactivity in intact living animals.

In one aspect, the technology described herein relates to a method of modulating the activity of a neuron, the method comprising; contacting the neuron with a photo-sensitive TrpA1 agonist as described herein, and exposing the neuron to electromagnetic radiation comprising a wavelength of from about 300 nm to about 700 nm. In one aspect, the technology described herein relates to a method of activating a TrpA1 channel, the method comprising; contacting the channel with a photo-sensitive TrpA1 agonist as described herein, and exposing the channel to electromagnetic radiation comprising a wavelength of from about 300 nm to about 700 nm. In one aspect, the technology described herein relates to a method of modulating the activity of a spatially-restricted subset of neurons in a population of neurons, the method comprising: contacting at least the subset of neurons with a photo-sensitive TrpA1 agonist as described herein and exposing at least the subset of neurons to electromagnetic radiation comprising a wavelength of from about 300 nm to about 700 nm. In one aspect, the technology described herein relates to a method of modulating the activity of a neuron for a selected duration, the method comprising contacting the neuron with a photo-sensitive TrpA1 agonist as described herein and exposing the neuron to electromagnetic radiation comprising a wavelength of from about 300 nm to about 700 nm for the selected duration; wherein the exposing modulates the activity of the neuron; and wherein the modulation ends after termination of the electromagnetic radiation exposure.

In some embodiments, the population of neurons can be the neurons present in a subject. In some embodiments, only the subset of neurons can be contacted with the compound. In some embodiments, only the subset of neurons can be exposed to the electromagnetic radiation. In some embodiments, substantially only neurons contacted with the compound and exposed to the electromagnetic radiation can be activated.

In some embodiments, the activity of the neuron can be increased. In some embodiments, the functional output of the neuron can be decreased. In some embodiments, the neuron can be functionally ablated. In some embodiments, the neuron can be ablated.

In some embodiments, the neuron can be a neuron of a subject in need of treatment for pain or inflammation. In some embodiments, the neuron can be exposed to electromagnetic radiation while the area comprising the neuron is anesthetized. In some embodiments, the neuron can be contacted with the compound while the area comprising the neuron is anesthetized. In some embodiments, the pain can be neuropathic.

In some embodiments, the neuron can be a neuron of a subject in need of treatment for spinal cord injury. In some embodiments, neuronal healing can be induced.

In some embodiments, the neuron can be a neuron of a subject in need of treatment for spasticity.

In some embodiments, the neuron can be the neuron of a subject in need of treatment for a condition selected from the group consisting of: chronic pain; back pain; lower back pain; pain resulting from trauma; phantom limb pain; diabetes; brachial plexus injury; neurovascular compression; herniated disc; herniated lumbar disc; herniated lumbar disc with radicular pain; Guillain-Barre syndrome; Charcot-Marie-Tooth disease; amytrophic lateral sclerosis; autoimmune peripheral neuropathies; brachial plexus injury; cervical root avulsion injury; neurovascular compression syndromes; trigmeninal neuralgia; hemifacial spasm; maladaptive CNS plasticity; epilepsy; seizure; dysautonomia; autonomic instability; hyperhidrosis; obsessive compulsive disorder; spinal cord injury; chronic spinal cord injury; acute spinal cord injury; a neurodegenerative disorder; Parkinson's disease; progressive supranuclear plasy; and dysfunction of the micturition reflex.

In one aspect, the technology described herein relates to a method of causing muscle contraction in a target muscle, the method comprising: contacting a neuron controlling a target muscle with a photo-sensitive TrpA1 agonist and exposing the neuron to electromagnetic radiation comprising a wavelength of from about 300 nm to about 700 nm. In some embodiments, the neuron can innervate the target muscle. In some embodiments, the neuron can be a motor neuron. In some embodiments, the target muscle can be a muscle selected from the group consisting of: smooth muscle; skeletal muscle; and cardiac muscle. In some embodiments, the muscle contraction enhances muscle tone. In some embodiments, the muscle contraction can be caused to induce compliance in the subject. In some embodiments, the muscle contraction can be caused to treat anorgasmia. In some embodiments, the muscle contraction can be caused to treat urinary retention or a dysfunction of the micturition reflex.

In one aspect, the technology described herein relates to a method of performing deep brain stimulation, the method comprising contacting a neuron in the brain with a photo-sensitive TrpA1 agonist and exposing the neuron to electromagnetic radiation comprising a wavelength of from about 300 nm to about 700 nm. In some embodiments, the deep brain stimulation can be performed on a subject having a condition selected from the group consisting of: Parkinson's disease; depression; major depression; chronic pain; tremor; dystonia; obsessive-compulsive disorder; bipolar disorder; Tourette syndrome; Lesch-Nyhan syndrome; epilepsy; phantom limb pain; unconsciousness or reduced consciousness; Alzheimer's disease; stroke; traumatic brain injury; impaired gastrointestinal motility; anorexia nervosa; addiction; obesity; and headache.

In one aspect, the technology described herein relates to a method of permitting non-ocular perception of electromagnetic radiation, the method comprising; contacting a neuron of a subject with a photo-sensitive TrpA1 agonist and exposing the neuron to electromagnetic radiation comprising a wavelength of from about 300 nm to about 700 nm; whereby said contacting and exposing activate the neuron, generating a sensation perceptible by the subject, whereby electromagnetic radiation is perceived by the subject in a non-ocular manner. In some embodiments, the neuron can be a peripheral neuron. In some embodiments, the neuron can be a sensory neuron. In some embodiments, at least the epidermis near the peripheral neuron can be exposed to the electromagnetic radiation. In some embodiments, the electromagnetic radiation forms a pattern when it illuminates the epidermis of the subject. In some embodiments, the electromagnetic radiation forms a series of patterns over the course of time during which it illuminates the epidermis of the subject. In some embodiments, the neuron can be a neuron in the subject's thalamus. In some embodiments, the exposure of the neuron to electromagnetic radiation can be controlled by a device which can detect electromagnetic radiation of any wavelength which is present in the environment surrounding the subject. In some embodiments, the subject can have a disease, disorder, or injury of the optic nerve.

In one aspect, the technology described herein relates to a method of providing a subject with voluntary control of a target neuron, the method comprising contacting a target neuron with a photo-sensitive TrpA1 agonist and exposing the target neuron to electromagnetic radiation comprising a wavelength of from about 300 nm to about 700 nm; wherein the electromagnetic radiation exposure is controlled by an input signal controlled by the subject. In some embodiments, the input signal can be the signaling activity of one or more of the subject's central nervous system neurons. In some embodiments, the target neuron can be a motor neuron. In some embodiments, prior to administration of the compound, the subject can be unable to voluntarily activate the motor neuron. In some embodiments, the subject can have a spinal cord injury.

In some embodiments of all the foregoing aspects, neuron can comprise at least one TrpA1 channel. In some embodiments of all the foregoing aspects, the neuron can be a non-retinal neuron. In some embodiments of all the foregoing aspects, the neuron can be a sensory neuron. In some embodiments of all the foregoing aspects, the neuron can be a motor neuron. In some embodiments of all the foregoing aspects, the subject can be non-transgenic. In some embodiments of all the foregoing aspects, the subject can be a mammal.

In some embodiments of all the foregoing aspects, the electromagnetic radiation can comprise a wavelength of from about 360 nm to about 450 nm. In some embodiments of all the foregoing aspects, the electromagnetic radiation can comprise a wavelength of from about 400 nm to about 440 nm. In some embodiments of all the foregoing aspects, the electromagnetic radiation can comprise a wavelength of from about 400 nm to about 420 nm. In some embodiments of all the foregoing aspects, the electromagnetic radiation can be provided by a source selected from the group consisting of: a laser; an electromagnetic radiation-emitting diode; a fluorescent or incandescent bulb; and the sun. In some embodiments of all the foregoing aspects, the electromagnetic radiation can pass through a filter prior to contacting the neuron or the subject.

In some embodiments of all the foregoing aspects, the compound can be administered to a subject by a route selected from the group consisting of: injection; direct application; microsurgery; endoscopic surgery; topically; orally, vaginally, and via contact with the gastro-intestinal lumen. In some embodiments of all the foregoing aspects, the compound can be administered systemically. In some embodiments of all the foregoing aspects, the compound can be administered locally. In some embodiments of all the foregoing aspects, the compound can be administered in a sustained release formulation.

In some embodiments of all the foregoing aspects, the electromagnetic radiation exposure can be localized. In some embodiments of all the foregoing aspects, the electromagnetic radiation exposure can be accomplished by illuminating the subject's epidermis. In some embodiments of all the foregoing aspects, the electromagnetic radiation exposure can be accomplished by illuminating a tissue of the subject by directing the electromagnetic radiation through the epidermis. In some embodiments of all the foregoing aspects, the electromagnetic radiation exposure can be accomplished by providing an electromagnetic radiation source to the vicinity of the neuron by a method selected from the group consisting of: illumination of tissue exposed by a surgical incision; fiber optics; implanted fiber optics; microsurgery; endoscope; endoscopic surgery; catheter; and an internalized or implanted light.

In one aspect of the technology described herein photosensitive TrpA1 agonists having the structure of formulas III, IV, V, VI, VII, and VII are provided.

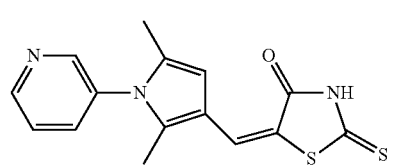

Formula III

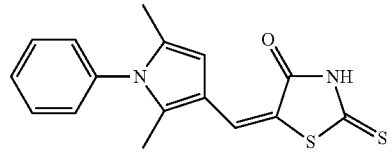

Formula IV

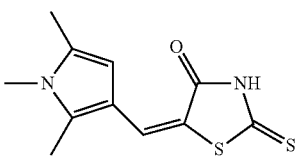

Formula V

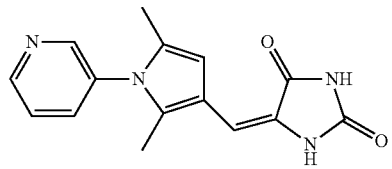

Formula VI

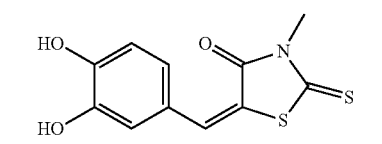

Formula VII

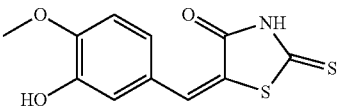

Formula VIII

The details of various embodiments of the invention are set forth in the description below. Other features, objects, and advantages of the present technology will be apparent from the description and the drawings, and from the claims.

DESCRIPTION OF THE DRAWINGS

FIG. 1C depicts a scatter plot demonstrating the behavioral excitation scores from 12,500 individual wells treated with one of 10,000 different compounds or DMSO. The y-axis represents the number of standard deviations of each excitation score from the control mean (Z-score). The labeled arrow indicates which well was treated with optovin. FIG. 1D is a representation of the chemical structure of optovin. FIG. 1E depicts a dose response curve showing optovin's effects on animal behavior ($EC_{50}=2$ μM; n=5). The difference between the 1 μM and 3 μM treatments is significant, p<0.001. FIG. 1F depicts a bar plot showing optovin's effects at the indicated stimulus wavelengths (n=10). At 387 nm, the difference between the treated and untreated groups is significant, p<0.001. FIG. 1G depicts a line plot showing excitation scores at the indicated stimulus intensities (i.e., the radiation intensity)(n=5). The difference between groups treated at 1.6 $\mu W/*mm^{-2}$ and 2 $\mu W*mm^{-2}$ is significant, p<0.001. FIG. 1H depicts a bar plot showing behavioral responses to repeated light stimuli (n=5). Differences between treated and untreated groups are significant, p<0.001. FIG. 1I depicts a dendrogram showing phenotypic distances between optovin and 700 annotated neuroactive compounds. Lower branches of the tree are collapsed for clarity. For all plots of the behavioral excitation score, values are means+/−standard deviation.

FIG. 2A depicts a horizontal bar plot demonstrating behavioral excitation scores from groups treated with the indicated optovin analogs (n=5). Optovin, 6b8, 6c1 analogs are active; 6c5, 6c7,6c2, and 6c3 are inactive. Differences between active and inactive groups are significant, p<0.001. Structures of the analogs are shown to the left of the bar plot. All compounds were tested at 10 μM, except for the 4g6 analog, which was tested at 100 μM. FIG. 2B depicts line plots demonstrating representative responses of animals treated with the indicated compounds. Grey vertical lines indicate light stimuli. Grey horizontal lines indicate the off-latency duration for motor responses following each stimulus. FIG. 2C depicts a bar plot demonstrating average behavioral response duration of groups treated with the indicated optovin analogs. Values are means+/−standard deviations (n=5). Differences between optovin and 4g6 and 6b8 are significant, p<0.01.

FIG. 3A depicts a bar plot demonstrating the behavioral excitation scores of intact and spinalized zebrafish embryos (30 hpf). Differences between treated and untreated groups are significant, p<0.001. Line plots showing calcium imaging of mouse DRG neurons in response to vehicle (FIG. 3B), optovin and light (FIG. 3C), and optovin without light (FIG. 3D). Black traces indicate calcium indicator fluorescence readings. No readings were recorded during the 1 min optovin treatment period in (FIG. 3D) when lights were turned off FIGS. 3E-3F depict line plots demonstrating representative behavioral phenotypes of optovin-treated heterozygous (FIG. 3E) and homozygous (FIG. 3F) TrpA1b mutants. The shaded regions indicate the timing of a 25 s light stimulus at 387 nm FIG. 3G depicts a bar plot showing the behavioral excitation score calculated for WT, heterozygous and homozygous mutant animals (n=21, 23 and 16 respectively). The difference between the WT and mutant groups is significant, p<0.001. FIG. 3H depicts representative series from optovin bathed (10 μM) HEK cells transfected with human TrpA1 (hTrpA1) as measured by whole-cell patch clamp, plotting the slope of the current-voltage relation during voltage ramps from 0 to +70 mV just prior to and following 405 nm illumination. Upper bars indicate the timing of optovin (10 μM), light (405 nm) and mustard oil (100 μM) treatments. FIG. 3I depicts a bar plot demonstrating the average change in current density of cells transfected with hTrpA1 and treated with optovin and/or light as indicated (n=9,*p<0.0085). FIG. 3J depicts a bar plot demonstrating calcium indicator dye fluorescence in cells transfected with GFP or hTrpA1 before and after a 2 min treatment with optovin and light (n=130, 120 cells). The difference between treated and untreated hTRPA1 transfected cells is significant, p<0.001.

FIG. 4A depicts a line plot demonstrating optovin's UV-Vis light spectrum absorbance at the indicated wavelengths. FIG. 4B depicts line plots demonstrating fluorescence of the singlet oxygen indicator dye SOG with and without optovin at the indicated light intensities. FIG. 4C depicts a bar plot demonstrating behavioral excitation scores from animals treated with optovin and DABCO (n=5, p<0.001). FIG. 4D depicts line plots depicting calcium imaging intensities before and after optovin treatment in cells transfected with the GFP, hTRPA1 or the indicated hTRPA1 point mutant. At 150 s on the x-axis, the lines represent cells treated as follows (top line=wildtype TRPA1; second from the top=C621S TRPA1; third line from the top=C633S TRPA1; fourth line from the top=C633/856S TRPA1; bottom line=GFP. FIG. 4E depicts a barplot quantifying the calcium response 1 min after optovin treatment (n=130, 120, 107, 111, 75 cells respectively) (p<0.01, *p<0.0001). The bars, from left to right, represent the response of cells transfected with: GFP; TRPA1; C621S TRPA1; C633S TRPA1; and C633S/C856S TRPA1. FIG. 4F depicts a barplot showing the mean excitation scores of animals treated with the indicated singlet oxygen generating photosensitizer n=130, 120, 107, 111, 75 cells (respectively) (p<0.01, *p<0.0001). Hyper, Hypericin; AO, acridine orange; MC, merocyanine 540; RB, rose bengal. FIG. 4G depicts the structures of the analogs tested in FIG. 4H. Methylation of the potential Michael acceptor is indicated with an arrow in analog 7d1. FIG. 4H depicts a bar plot showing the average behavioral response of groups treated with the indicated optovin analogs. Values are means+/−standard deviations (n=3). Differences between optovin and 7c7 are significant compared to DMSO, p<0.001. The difference between DMSO and 7d1 is not significant, p=0.8. All compounds were tested at 10 μM.

FIG. 5A depicts a bar graph demonstrating the PMR and optovin response of embryos differ at different stages of development (30 or 120 hours post fertilization (hpf)). FIG. 5B is a bar graph demonstrating that the PMR and optovin response varies in intact vs. spinalized animals. FIG. 5C depicts a bar graph demonstrating that the PMR and optovin response vary with the wavelength of light provided. FIG. 5D depicts a bar graph demonstrating that the PMR and optovin response differ as the duration of electromagnetic radiation stimulus is increased.

FIG. 7A depicts a series of photographs of spinalized zebrafish before and after photo-stimulation of the dorsal fin. FIG. 7B depicts a series of photographs of spinalized zebrafish responding to laser photo-stimulation. Arrowheads indicate approximate location of the 405 nm laser point stimulus.

FIGS. 10A-10D demonstrate that optovin-treated spinalized preparations respond to light. Photographs showing zebrafish embryos at 35 hpf before (FIG. 10A) and after (FIG. 10B) transection posterior to the hindbrain as indicated by the dashed line. fb, forebrain; hb, hindbrain. (FIGS. 10C-10D) Examples of how spinalized (10C) and optovin-treated spinalized (FIG. 10D) animals respond to light stimuli.

FIGS. 13A-13C depict the calcium imaging of cells transfected with the TRPV1 (FIG. 13A), TPM8 (FIG. 13B), or TRPA1 (FIG. 13C) and stimulated with the indicated agonist. FIGS. 13D-13F depict the quantification of the responses shown in FIGS. 13A-13C, respectively. (p<0.01, *p<0.0001).

FIGS. 14A-14D are graphs demonstrating that photoactivated optovin generates singlet oxygen, but negligible amounts of hydroxyl radicals and superoxide. FIG. 14A depicts a Line plot showing the fluorescence of singlet oxygen sensor green (SOG) and with the indicated compounds and light. Compared to a known photosensitizer (PEI-ce6) that absorbs blue light and produces singlet oxygen with a quantum yield of about 0.6, optovin could be estimated to have a quantum yield of about 0.04. FIGS. 14B-14D depict line plots showing NBT absorbance (a readout of superoxide generation) at increasing intensity of blue light with optovin and vehicle (FIG. 14B), ascorbate (FIG. 14C), and NADH (FIG. 14D). Increased absorbance would be expected only in presence of an electron donor such as ascorbate or NADH. There is no evidence of hydroxyl radical production (data not shown).

DETAILED DESCRIPTION

Figure 1A:
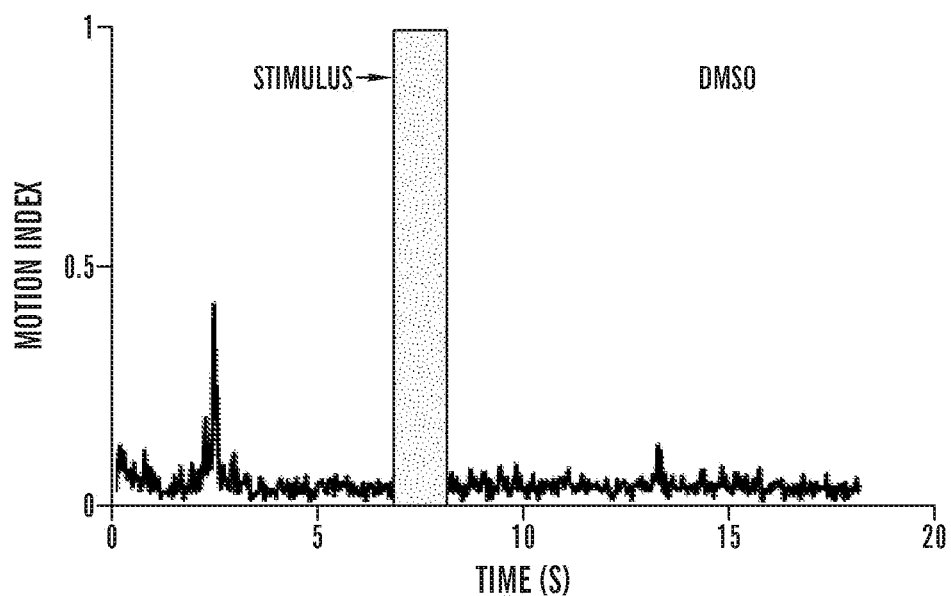
FIGS. 1A-1I depict the identification of optovin, a compound permitting light-mediated neuronal excitation. Plots show the zebrafish behavioral response of DMSO (1A) and optovin (1B) treated animals. The gray vertical bar indicates the timing of a 1 s white light stimulus.

Described herein are methods and compositions for modulating the activity of a neuron with electromagnetic radiation (e.g. light). More specifically, methods and compositions as described relating to the use of optovin and related compositions (e.g. photo-sensitive TrpA1 agonists) to regulate neuronal activity in a spatially and temporally desired manner by illuminating a neuron contacted with optovin or a related compound with electromagnetic radiation, resulting in activation of that neuron. Various embodiments and applications of this technology are described herein below, as are considerations necessary for the practice of such embodiments.

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein, the terms "neuron," "nerve," or "nerve cell" are used interchangeably to refer to cells found in the nervous system that are specialized to receive, process, and transmit information as nerve signals. Neurons can include a central cell body or soma, and two types of projections: dendrites, by which, in general, the majority of neuronal signals are conveyed to the cell body; and axons, by which, in general, the majority of neuronal signals are conveyed from the cell body to effector cells, such as target neurons or muscle. Neurons can convey information from tissues and organs into the central nervous system (afferent or sensory neurons) and transmit signals from the central nervous systems to effector cells (efferent or motor neurons). Other neurons, designated interneurons, connect neurons within the nervous system. In some embodiments, the neuron modulated according to the methods described herein is not a retinal neuron. In some embodiments, the neuron modulated according to the methods described herein comprises at least one TrpA1 polypeptide.

As used herein, the term "peripheral neuron" refers to a neuron located, at least in part, outside of the brain and/or spinal cord.

As used herein, the term "motor neuron" refers to a neuron that sends output signals to a muscle, gland, or other effector tissue. Motor neurons can be neurons located in the central nervous system (CNS) that project their axons outside the CNS and directly or indirectly control muscles or other effector tissues.

As used herein, the term "sensory neuron" refers to a neuron that receives and transmits information relating to sensory input, e.g. stimuli such as heat, touch, pressure, cold, vibration, etc. Sensory neurons can be peripheral neurons or can be located partially or entirely within the central nervous system.

As used herein, the term "electromagnetic radiation" refers to a beam of photons of any appropriate wavelength(s), i.e. a wavelength which can activate a photosensitive TrpA1 agonist as described herein. This can include the optical spectrum (e.g. from about 400 nm to 800 nm) (i.e. visible light) but can also include electromagnetic radiation of other wavelengths, e.g. ultraviolet radiation, infrared radiation, X-rays, gamma radiation, and microwave, radar and/or radio waves. Electromagnetic radiation can also be defined as radiation comprising oscillating electric and magnetic fields. The term illuminating includes directing or transmitting electromagnetic radiation to a target. Electromagnetic radiation comprising part or all of the spectrum of electromagnetic radiation which can be visible to the unaided human eye can be referred to herein as "light."

As used herein, the term "dosage combination" refers to the dose of a photo-sensitive TrpA1 agonist in combination with a dose of electromagnetic radiation. Parameters which can differentiate two separate dosage combinations include, but are not limited to: the identity of the photo-sensitive TrpA1 agonist, the concentration of the photo-sensitive TrpA1 agonist, the frequency of administration of the agonist, the route of administration, the intensity of radiation, the wavelength(s) of the electromagnetic radiation exposure, the means of transmitting the radiation, and the frequency of the electromagnetic radiation exposure.

The terms "decrease," "reduce," "reduced", "reduction", "decrease," and "inhibit" are all used herein generally to mean a decrease by a statistically significant amount relative to a reference. However, for avoidance of doubt, "reduce," "reduction" or "decrease" or "inhibit" typically means a decrease by at least 10% as compared to the absence of a given reference and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to a given reference, or any decrease between 10-99% as compared to a given reference.

The terms "increased", "increase" or "enhance" or "activate" are all used herein to generally mean an increase by a statically significant amount; for the avoidance of any doubt, the terms "increased", "increase" or "enhance" or "activate" mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, the terms "treat," "treatment," "treating," or "amelioration" when used in reference to a disease, disorder, or medical condition, refer to therapeutic treatments for a condition, wherein the object is to reverse, alleviate, ameliorate, inhibit, slow down, or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of symptoms, delay or slowing of symptoms and/or the condition, and amelioration or palliation of symptoms associated with the condition.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutical composition" refers to the active agent in combination with a pharmaceutically acceptable carrier e.g. a carrier commonly used in the pharmaceutical industry.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

As used herein, the term "proteins" and "polypeptides" are used interchangeably herein to designate a series of amino acid residues connected to each other by peptide bonds between the alpha-amino and carboxy groups of adjacent residues. The terms "protein", and "polypeptide", which are used interchangeably herein, refer to a polymer of protein amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. The terms, "patient", "individual" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used, for example, as subjects that represent animal models of, for example, inflammation. In addition, the methods described herein can be used to treat domesticated animals and/or pets. A subject can be male or female.

A subject can be one who has been previously diagnosed with or identified as suffering from or having a condition in need of treatment (e.g. pain) or one or more complications related to such a condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to condition or a subject who does not exhibit risk factors. A "subject in need" of treatment for a particular condition can be a subject having that condition, diagnosed as having that condition, or at risk of developing that condition.

As used herein, the term "inflammation" refers to the complex biological response of vascular tissues to stimuli, such as pathogens, damaged cells, ischemia, antigen-antibody interactions, irritants and thermal or other physical injury. Inflammation is characterized by an increase in erythema, edema, tenderness (hyperalgesia), and pain at the inflamed site. In some embodiments, inflammation can be chronic. In some embodiments, inflammation can be acute.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Other than in the operating examples, or where otherwise indicated, all numbers expressing quantities of ingredients or reaction conditions used herein should be understood as modified in all instances by the term "about." The term "about" when used in connection with percentages can mean±1%.

The term "statistically significant" or "significantly" refers to statistical significance and generally means a two standard deviation (2SD) difference, above or below a reference value. Additional definitions are provided in the text of individual sections below.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); and Molecular Biology and Biotechnology: a Comprehensive Desk Reference, published by VCH Publishers, Inc., 1995 (ISBN 1-56081-569-8).

Unless otherwise stated, the present invention was performed using standard procedures, as described, for example in Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

Embodiments of the technology described herein relate to methods and compositions which activate the Transient Receptor Potential cation channel, subfamily A, member 1 (TrpA1) ion channel. As used herein, "TrpA1" refers to a chemosensor transmembrane ion channel polypeptide encoded by the TrpA1 gene. Human sequences include e.g. SEQ ID NO: 1 (human polypeptide); SEQ ID NO: 2 (human mRNA); NCBI Gene ID 8989. Other species' TrpA1 genes and polypeptides are known in the art. The TrpA1 channel is capable of responding to a number of stimuli, including, e.g. formalin, isothyocyanate compounds, and nicotine. The TRP family of polypeptides comprises at least six subfamilies; TRPV, TRPC, TRPM, TRPA, TRPP, and TRPML. The TRP channel family comprises ion channels formed from polypeptides with six transmembrane segments and carboxy and amino termini facing the intracellular side of the membrane. The channels are believed to be formed by four subunits. The pore of the channel is predicted to be between the fifth and sixth segment and upon activating becomes non-selectively permeable to cations. The channels formed by members of the TRP family can vary in overall shape, e.g. TRPC3 and TRPM2 form very high volume structures while TRPV1 forms a lower volume structure with a "hanging gondola" in the cytoplasmic space. TRP channels can comprise a number of domains, including ankyrin repeat domains (ARDs), coiled-coils (e.g. TRPM7 and TRP2), alpha-kinase domains (e.g. TRPM7), and EF-hand domains (e.g. TRPP2). The ARD of a TRP channel (e.g. the TRPV subfamily) can comprise an ATP binding site and interact with the Ca-calmodulin complex. The C-terminal coiled-coil domain (e.g. of the TRPM subfamily), structure and symmetry can control specificity for channel assembly with other subunits.

TRPA1 can comprise between 14 and 17 N-terminal ankyrin repeats per subunit, an N-terminal EF hand motif between the $11^{th}$ and $12^{th}$ ankyrin repeat, and possibly a C-terminal coiled-coil domain. The ankyrin domain has been suggested to play a role in mechano-sensing, channel gating, protein-protein interaction, and/or multi-ligand binding. The ARD is necessary for plasma membrane expression of TrpA1. The EF-hand domain is necessary for TrpA1 function. TrpA1 can be activated, for example, by covalent modification of certain of its cysteine residues or by thiol trapping. These residues are located in the N-terminal region of the polypeptide. Electrophilic agonists are believed to covalently bind lysine and cysteine N-terminal residues. The critical cysteine residues in the human TrpA1 can include Cys619, Cys649, Cys663, Cys622, Cys642, Cys666, Cys422, and Cys415. The overall structure is similar to that of TRPV, with a compact transmembrane domain, tetrameric assembly, and a basket-like cytoplasmic domain. It is believed that residues 31-437 of the ankyrin repeat domain can be brought into proximity to residues 438-667 of an adjacent monomer to form a ligand-binding structure. TrpA1 is $Ca^{2+}$-selective, a property which requires Asp918. The cysteines at residues 621, 633, and 856 of wildtype human TrpA1 can be important for activation of a TrpA1 channel by electrophile compounds. See, e.g. Latorre, R. JGP 2009 133:227-9; Cvetkov, T. L. et al. JBC 2011 286:38168-76; Hinman, A. et al. PNAS 2006 103:19564-8; and Nilius, B. et al. J Physiol 2011 589:1543-9; which are incorporated by reference herein in their entireties.

Mice administered TrpA1 antagonists, or in which TrpA1 has been genetically ablated appear to be insensitive to formalin-induced pain. TrpA1 may also be responsive to mechanical stress or temperature extremes; e.g. TrpA1 is implicated in the detection of infrared radiation of pit vipers. Activation of TrpA1 can also have an antinociceptive effect; e.g. acetaminophen-induced antinociception in the spinal cord has been shown to be dependent upon TrpA1 (Andersson et al. Nature Communications 2011 2:1559).

When TrpA1 is activated, the channel allows, for example, the flow of $Ca^{2+}$ into the cytoplasm of a cell. The change in ion concentrations results in a change in the voltage gradient which exists across the plasma membrane of a neuron. If the change in voltage is significant enough, an action potential (i.e. an electrochemical pulse) will travel along the neuron's axon and activate signaling to other cells via the synapse. As used herein, "activating a TrpA1 channel" refers to causing the TrpA1 channel to permit the flow of ions across a plasma membrane. Methods for detecting activation of a TrpA1 channel are known in the art and are described herein in the Examples. Briefly, a cell which normally does not express TrpA1 (e.g. HEK293T) which is transfected with a functional TrpA1 gene can be contacted with a candidate activator of TrpA1. The concentration of ions, e.g. calcium, inside the cell can be monitored with fluorescent calcium-sensitive reporter molecules (e.g. Fura 2-AM; Cat. No. F0888 Sigma-Aldrich; St. Louis, Mo. or Fluo-4 Cat No. F-14201 Invitrogen, Grand Island, N.Y.; fluorescent indicators of calcium concentration). An increase in TrpA1 channel activation can result in a higher Ca2+ concentration and thus a higher fluorescent signal. Appropriate cells can include, for example, HEK cells, stably transfected with the TRP channel of interest (Chantest, Cleveland Ohio). Cells can be plated in 384 well plates and loaded with Fluo-4 acetoxy methyl ester at 2-4 uM for 30-60 minutes, followed by 3 five minute wash steps. Then the basal fluorescence can be measured using a standard F ITC filter set, followed by addition of compounds at a range of doses and repeated measurement of fluorescence. Next each well can be illuminated with a one second pulse of unfiltered light from a mercury bulb source and the fluorescence re-assayed. Finally, known agonists for each TRP channel can be added and fluorescence re-assayed. This last step serves not only as a positive control, but also permits identification of antagonists of ligand-gated activity. Compounds with measurable activity can be assayed over the full range of concentrations from no effect to saturation. In addition, compounds can be assayed over the full spectrum of light activation (300-800 nm) and their kinetics of photo-activation/deactivation can be fully characterized. Alternatively, ion channel activity can be analyzed via whole-cell patch clamping to detect changes in voltage or current.

Activation of TrpA1 can lead to activation of a neuron comprising TrpA1. As used herein, "activating a neuron" refers to causing an action potential to travel along the neuron's axon. In some embodiments, the neuron is a sensory neuron and activation can result in transmission of a signal to the central nervous system. In some embodiments, the neuron is a motor neuron and activation can result in transmission of a signal to a muscle cell which causes contraction of the muscle fiber.

As used herein, a "neuron comprising a TrpA1 channel" can refer to any neuron (e.g. a sensory neuron or a motor neuron) which comprises at least one functional TrpA1 channel. A neuron comprising a TrpA1 channel can be found in any tissue of a vertebrate organism. TrpA1 expression has been detected in, for example, DRG neurons, sensory epithelium of the utricle, sensory neurons, hair cells, vasculature, heart, brain, thymus, bone marrow, spleen, blood, spinal cord, skeletal muscle, smooth muscle, kidney, lung, liver, prostate, skin, thyroid, salivary gland, ovary, placenta, testis, cervix, and pancreas.

Described herein are methods and compounds relating to the activation of TrpA1 channels and/or neurons comprising TrpA1 channels. In some embodiments, the activation of TrpA1 channels and/or neurons comprising TrpA1 channels can be photo-regulated according to the methods described herein. Accordingly, provided herein are compounds which can activate TrpA1 channels in an electromagnetic radiation-dependent manner. Absent an appropriate electromagnetic-radiation stimulus, the compounds exist in a state that will not affect TrpA1 activity. Upon illumination by electromagnetic radiation, the compounds can be activated, and, in turn, can induce TrpA1 activity. As electromagnetic radiation can be applied non-invasively, with varying levels of intensity, and with a high degree of spatial and temporal control, this allows activation of specific channels and/or neurons in a spatially and temporally-controlled manner. Compounds suitable for use in the methods described herein are referred to herein as "photo-sensitive TrpA1 agonists."

In one aspect of the technology described herein, the photo-sensitive TrpA1 agonists are of formula Ia or Ib:

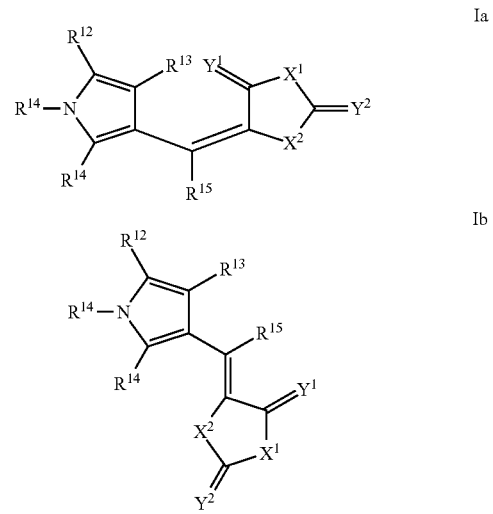

wherein $R^{11}$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo; $R^{12}$, $R^{13}$, $R^{14}$, and $R^{15}$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; -; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo; $Y^1$ and $Y^2$ are independently O or S; $X^1$ is O, N$R^{16}$, or S;

$X^2$ is O, N$R^{17}$, or S; $R^{16}$ and $R^{17}$ are independently hydrogen; a protecting group; aliphatic; heteroaliphatic; acyl; aryl; alkylhalo; or heteroaryl;

with the proviso that Formula Ia is not

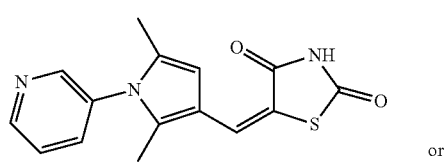

or

In some embodiments $R^{11}$ is cyclic, substituted or unsubstituted, branched or unbranched aliphatic; cyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl.

In some embodiments $R^{11}$ is substituted or unsubstituted, branched or unbranched aryl. In some embodiments, $R^{11}$ is unsubstituted aryl. In some embodiments, $R^{11}$ is substituted aryl. In some embodiments, $R^{11}$ is unsubstituted phenyl. In some embodiments, $R^{11}$ is substituted phenyl.

In some embodiments $R^{11}$ is substituted or unsubstituted, branched or unbranched heteroaryl. In some embodiments, $R^{11}$ is unsubstituted heteroaryl. In some embodiments, $R^{11}$ is substituted heteroaryl. In some embodiments, $R^{11}$ is unsubstituted pyridine. In some embodiments, $R^{11}$ is unsubstituted 2-pyridine. In some embodiments, $R^{11}$ is substituted pyridine. In some embodiments, $R^{11}$ is substituted 2-pyridine.

In some embodiments, $R^{11}$ is substituted at least at the ortho position. In some embodiments, $R^{11}$ is substituted at least at the meta position. In some embodiments, $R^{11}$ is substituted at least at the para position. In some embodiments, $R^{11}$ is substituted at more than one position. In some embodiments, $R^{11}$ is substituted with at least one $C_{1-4}$ alkyl. In some embodiments, $R^{11}$ is substituted with at least one $C_{1-4}$ alkoxy. In some embodiments, $R^{11}$ is substituted with at least one $NO_2$. In some embodiments, $R^{11}$ is substituted with at least one halogen. In some embodiments, $R^{11}$ is substituted with at least one O(PG), wherein PG is a hydroxyl protecting group. In some embodiments, $R^{11}$ is substituted with at least one OH. In some embodiments, $R^{11}$ is substituted with at least two OH.

In some embodiments, $R^{11}$ is a straight chain aliphatic. In some embodiments, $R^{11}$ is a branched chain aliphatic. In some embodiments, $R^{11}$ is a straight chain heteroaliphatic. In some embodiments, $R^{11}$ is a branched chain heteroaliphatic. In some embodiments, $R^{11}$ is $C_{1-8}$ alkyl, $C_{2-4}$ alkenyl, $C_{2-4}$ alkynyl. In some embodiments $R^{11}$ is acyl. In some embodiments, $R^{11}$ is $C_{1-4}$ alkyl. In some embodiments, $R^{11}$ is methyl, ethyl, n-propyl, i-propyl, n-butyl, i-butyl, or t-butyl.

In some embodiments $R^{12}$ is cyclic, substituted or unsubstituted, branched or unbranched aliphatic; cyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl.

In some embodiments $R^{12}$ is substituted or unsubstituted, branched or unbranched aryl. In some embodiments, $R^{12}$ is unsubstituted aryl. In some embodiments, $R^{12}$ is substituted aryl. In some embodiments, $R^{12}$ is unsubstituted phenyl. In some embodiments, $R^{12}$ is substituted phenyl.

In some embodiments $R^{12}$ is substituted or unsubstituted, branched or unbranched heteroaryl. In some embodiments, $R^{12}$ is unsubstituted heteroaryl. In some embodiments, $R^{12}$ is substituted heteroaryl.

In some embodiments, $R^{12}$ is substituted at least at the ortho position. In some embodiments, $R^{12}$ is substituted at least at the meta position. In some embodiments, $R^{12}$ is substituted at least at the para position. In some embodiments, $R^{12}$ is substituted at more than one position. In some embodiments, $R^{12}$ is substituted with at least one $C_{1-4}$ alkyl. In some embodiments, $R^{12}$ is substituted with at least one $C_{1-4}$ alkoxy. In some embodiments, $R^{12}$ is substituted with at least one $NO_2$. In some embodiments, $R^{12}$ is substituted with at least one halogen. In some embodiments, $R^{12}$ is substituted with at least one O(PG), wherein PG is a hydroxyl protecting group. In some embodiments, $R^{12}$ is substituted with at least one OH. In some embodiments, $R^{12}$ is substituted with at least two OH.

In some embodiments, $R^{12}$ is a straight chain aliphatic. In some embodiments, $R^{12}$ is a branched chain aliphatic. In some embodiments, $R^{12}$ is a straight chain heteroaliphatic. In some embodiments, $R^{12}$ is a branched chain heteroaliphatic. In some embodiments, $R^{12}$ is $C_{1-8}$ alkyl, $C_{2-4}$ alkenyl, $C_{2-4}$ alkynyl. In some embodiments $R^{12}$ is acyl. In some embodiments, $R^{12}$ is $C_{1-4}$ alkyl. In some embodiments, $R^{12}$ is methyl, ethyl, n-propyl, i-propyl, n-butyl, i-butyl, or t-butyl. In some embodiments, $R^{12}$ is hydrogen.

In some embodiments $R^{13}$ is substituted or unsubstituted, branched or unbranched aryl. In some embodiments, $R^{13}$ is unsubstituted aryl. In some embodiments, $R^{13}$ is substituted aryl. In some embodiments, $R^{13}$ is unsubstituted phenyl. In some embodiments, $R^{13}$ is substituted phenyl.

In some embodiments $R^{13}$ is substituted or unsubstituted, branched or unbranched heteroaryl. In some embodiments, $R^{13}$ is unsubstituted heteroaryl. In some embodiments, $R^{13}$ is substituted heteroaryl.

In some embodiments, $R^{13}$ is substituted at least at the ortho position. In some embodiments, $R^{13}$ is substituted at least at the meta position. In some embodiments, $R^{13}$ is substituted at least at the para position. In some embodiments, $R^{13}$ is substituted at more than one position. In some embodiments, $R^{13}$ is substituted with at least one $C_{1-4}$ alkyl. In some embodiments, $R^{13}$ is substituted with at least one $C_{1-4}$ alkoxy. In some embodiments, $R^{13}$ is substituted with at least one $NO_2$. In some embodiments, $R^{13}$ is substituted with at least one halogen. In some embodiments, $R^{13}$ is substituted with at least one O(PG), wherein PG is a hydroxyl protecting group. In some embodiments, $R^{13}$ is substituted with at least one OH. In some embodiments, $R^{13}$ is substituted with at least two OH.

In some embodiments, $R^{13}$ is a straight chain aliphatic. In some embodiments, $R^{13}$ is a branched chain aliphatic. In some embodiments, $R^{13}$ is a straight chain heteroaliphatic. In some embodiments, $R^{13}$ is a branched chain heteroaliphatic. In some embodiments, $R^{13}$ is $C_{1-8}$ alkyl, $C_{2-4}$ alkenyl, $C_{2-4}$ alkynyl. In some embodiments $R^{13}$ is acyl. In some embodiments, $R^{13}$ is $C_{1-4}$ alkyl. In some embodiments, $R^{13}$ is methyl, ethyl, n-propyl, i-propyl, n-butyl, i-butyl, or t-butyl. In some embodiments, $R^{13}$ is hydrogen.

In some embodiments $R^{14}$ is substituted or unsubstituted, branched or unbranched aryl. In some embodiments, $R^{14}$ is unsubstituted aryl. In some embodiments, $R^{14}$ is substituted aryl. In some embodiments, $R^{14}$ is unsubstituted phenyl. In some embodiments, $R^{14}$ is substituted phenyl.

In some embodiments $R^{14}$ is substituted or unsubstituted, branched or unbranched heteroaryl. In some embodiments, $R^{14}$ is unsubstituted heteroaryl. In some embodiments, $R^{14}$ is substituted heteroaryl.

In some embodiments, $R^{14}$ is substituted at least at the ortho position. In some embodiments, $R^{14}$ is substituted at least at the meta position. In some embodiments, $R^{14}$ is substituted at least at the para position. In some embodiments, $R^{14}$ is substituted at more than one position. In some embodiments, $R^{14}$ is substituted with at least one $C_{1-4}$ alkyl. In some embodiments, $R^{14}$ is substituted with at least one $C_{1-4}$ alkoxy. In some embodiments, $R^{14}$ is substituted with at least one $NO_2$. In some embodiments, $R^{14}$ is substituted with at least one halogen. In some embodiments, $R^{14}$ is substituted with at least one O(PG), wherein PG is a hydroxyl protecting group. In some embodiments, $R^{14}$ is substituted with at least one OH. In some embodiments, $R^{14}$ is substituted with at least two OH.

In some embodiments, $R^{14}$ is a straight chain aliphatic. In some embodiments, $R^{14}$ is a branched chain aliphatic. In some embodiments, $R^{14}$ is a straight chain heteroaliphatic. In some embodiments, $R^{14}$ is a branched chain heteroaliphatic. In some embodiments, $R^{14}$ is $C_{1-8}$ alkyl, $C_{2-4}$ alkenyl, $C_{2-4}$ alkynyl. In some embodiments, $R^{14}$ is aryl or heteroaryl. In some embodiments $R^{14}$ is acyl. In some embodiments, $R^{14}$ is $C_{1-4}$ alkyl. In some embodiments, $R^{14}$ is methyl, ethyl, n-propyl, i-propyl, n-butyl, i-butyl, or t-butyl. In some embodiments, $R^{14}$ is hydrogen.

In some embodiments, $R^{12}$ and $R^{14}$ are the same. In some embodiments, $R^{12}$ and $R^{14}$ are different. In some embodiments, at least $R^{12}$ or $R^{14}$ is $C_{1-4}$ alkyl. In some embodiments, at least $R^{12}$ or $R^{14}$ is $C_{1-4}$ alkyl. In some embodiments, both $R^{12}$ and $R^{14}$ are $C_{1-4}$ alkyl. In some embodiments, at least $R^{12}$ or $R^{14}$ is methyl. In some embodiments, at least $R^{12}$ or $R^{14}$ is methyl. In some embodiments, both $R^{12}$ and $R^{14}$ are methyl.

In some embodiments, $R^{12}$ and $R^{13}$ are the same. In some embodiments, $R^{12}$ and $R^{13}$ are different. In some embodiments, $R^{13}$ and $R^{14}$ are the same. In some embodiments, $R^{13}$ and $R^{14}$ are different. In some embodiments, $R^{12}$, $R^{13}$ and $R^{14}$ are the same. In some embodiments, $R^{12}$, $R^{13}$ and $R^{14}$ are different. In some embodiments, at least two of $R^{12}$, $R^{13}$ and $R^{14}$ are the same. In some embodiments, $R^{12}$ and $R^{14}$ are methyl and $R^{13}$ is hydrogen.

In some embodiments $R^{15}$ is substituted or unsubstituted, branched or unbranched aryl. In some embodiments, $R^{15}$ is unsubstituted aryl. In some embodiments, $R^{15}$ is substituted aryl. In some embodiments, $R^{15}$ is unsubstituted phenyl. In some embodiments, $R^{15}$ is substituted phenyl.

In some embodiments $R^{15}$ is substituted or unsubstituted, branched or unbranched heteroaryl. In some embodiments, $R^{15}$ is unsubstituted heteroaryl. In some embodiments, $R^{15}$ is substituted heteroaryl.

In some embodiments, $R^{15}$ is substituted at least at the ortho position. In some embodiments, $R^{15}$ is substituted at least at the meta position. In some embodiments, $R^{15}$ is substituted at least at the para position. In some embodiments, $R^{15}$ is substituted at more than one position. In some embodiments, $R^{15}$ is substituted with at least one $C_{1-4}$ alkyl. In some embodiments, $R^{15}$ is substituted with at least one $C_{1-4}$ alkoxy. In some embodiments, $R^{15}$ is substituted with at least one $NO_2$. In some embodiments, $R^{15}$ is substituted with at least one halogen. In some embodiments, $R^{15}$ is substituted with at least one O(PG), wherein PG is a hydroxyl protecting group. In some embodiments, $R^{15}$ is substituted with at least one OH. In some embodiments, $R^{15}$ is substituted with at least two OH.

In some embodiments, $R^{15}$ is a straight chain aliphatic. In some embodiments, $R^{15}$ is a branched chain aliphatic. In some embodiments, $R^{15}$ is a straight chain heteroaliphatic. In some embodiments, $R^{15}$ is a branched chain heteroaliphatic. In some embodiments, $R^{15}$ is $C_{1-8}$ alkyl, $C_{2-4}$ alkenyl, $C_{2-4}$ alkynyl. In some embodiments $R^{15}$ is acyl. In some embodiments, $R^{15}$ is $C_{1-4}$ alkyl. In some embodiments, $R^{15}$ is methyl, ethyl, n-propyl, i-propyl, n-butyl, i-butyl, or t-butyl. In some embodiments, $R^{15}$ is hydrogen.

In some embodiments, $Y^1$ is O. In some embodiments, $Y^1$ is S. In some embodiments, $Y^2$ is O. In some embodiments, $Y^2$ is S. In some embodiments, $Y^1$ and $Y^2$ are the same. In some embodiments, $Y^1$ and $Y^2$ are different.

In some embodiments, $X^1$ is O. In some embodiments, $X^1$ is S. In some embodiments, $X^1$ is $NR^{16}$.

In some embodiments, $R^{16}$ is hydrogen. In some embodiments, $R^{16}$ is a nitrogen protecting group. In some embodiments, $R^{16}$ is $C_{1-8}$ alkyl. In some embodiments, $R^{16}$ is heteroaliphatic. In some embodiments, $R^{16}$ is acyl. In some embodiments, $R^{16}$ is aryl or heteroaryl. In some embodiments, $R^{16}$ is alkylamino or dialkylamino. In some embodiments, $R^{16}$ is alkylhalo.

In some embodiments, $X^2$ is O. In some embodiments, $X^2$ is S. In some embodiments, $X^2$ is $NR^{17}$.

In some embodiments, $R^{17}$ is hydrogen. In some embodiments, $R^{17}$ is a nitrogen protecting group. In some embodiments, $R^{17}$ is $C_{1-8}$ alkyl. In some embodiments, $R^{17}$ is heteroaliphatic. In some embodiments, $R^{17}$ is acyl. In some embodiments, $R^{17}$ is aryl or heteroaryl. In some embodiments, $R^{17}$ is alkylamino or dialkylamino. In some embodiments, $R^{17}$ is alkylhalo.

In some embodiments, a compound of formula Ia can have the structure of formula III, also referred to herein as optovin.

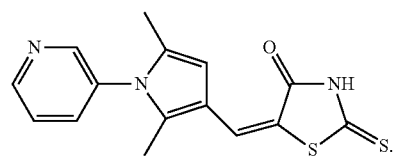

Formula III

In some embodiments, a compound of formula Ia can have the structure of Formula IV, also referred to herein as 6b8.

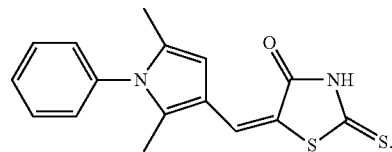

Formula IV

In some embodiments, a compound of formula Ia can have the structure of Formula V, also referred to herein as 6c1.

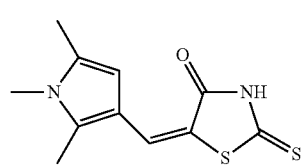

Formula V

In some embodiments, a compound of formula Ia can have the structure of Formula VI, also referred to herein as 6c4.

Formula VI

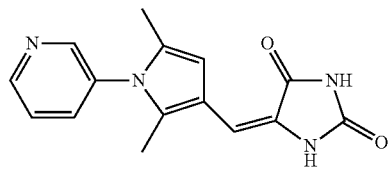

In one aspect of the technology described herein, the photo-sensitive TrpA1 agonists are of formula IIa or IIb:

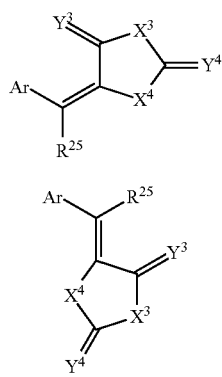

wherein Ar is cyclic substituted or unsubstituted, branched or unbranched aliphatic; cyclic substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $R^{25}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo; $Y^3$ and $Y^4$ are independently O or S; $X^3$ is O, $NR^{26}$, or S; $X^4$ is O, $NR^{27}$, or S; $R^{26}$ and $R^{27}$ are independently hydrogen; a protecting group; aliphatic; heteroaliphatic; acyl; aryl; alkylhalo; or heteroaryl; with the proviso that Formula IIa is not

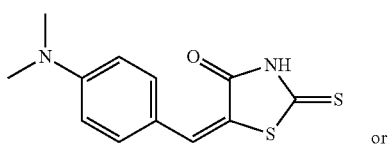

or

-continued

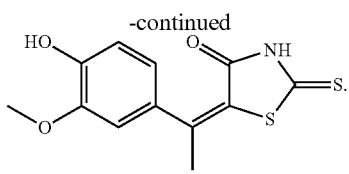

In some embodiments, Ar is aryl. In some embodiments, Ar is a five-membered aryl. In some embodiments, Ar is a six-membered aryl. In some embodiments, Ar is a seven-membered aryl. In some embodiments, Ar is a eight-membered aryl. In some embodiments, Ar is a nine-membered aryl. In some embodiments, Ar is a ten-membered aryl. In some embodiments, Ar is an eleven-membered aryl. In some embodiments, Ar is a twelve-membered aryl. In some embodiments, Ar is a thirteen-membered aryl. In some embodiments, Ar is a fourteen-membered aryl.

In some embodiments, Ar is heteroaryl. In some embodiments, Ar is a five-membered heteroaryl. In some embodiments, Ar is a six-membered heteroaryl. In some embodiments, Ar is a seven-membered heteroaryl. In some embodiments, Ar is a eight-membered heteroaryl. In some embodiments, Ar is a nine-membered heteroaryl. In some embodiments, Ar is a ten-membered heteroaryl. In some embodiments, Ar is an eleven-membered heteroaryl. In some embodiments, Ar is a twelve-membered heteroaryl. In some embodiments, Ar is a thirteen-membered heteroaryl. In some embodiments, Ar is a fourteen-membered heteroaryl.

In some embodiments, Ar is a N-containing heteroaryl. In some embodiments, Ar is a O-containing heteroaryl. In some embodiments, Ar is a S-containing heteroaryl. In some embodiments, Ar contains at least one heteroatom. In some embodiments, Ar contains at least two heteroatoms. In some embodiments, Ar contains at least three heteroatoms. In some embodiments, Ar contains at least four heteroatoms. In some embodiments, Ar contains at least five heteroatoms. In some embodiments, Ar contains at least six heteroatoms. In some embodiments, at least two heteroatoms are the same. In some embodiments, all heteroatoms are different. In some embodiments, all heteroatoms are the same.

In some embodiments Ar is substituted or unsubstituted, branched or unbranched aryl. In some embodiments, Ar is unsubstituted aryl. In some embodiments, Ar is substituted aryl. In some embodiments, Ar is unsubstituted phenyl. In some embodiments, Ar is substituted phenyl.

In some embodiments Ar is substituted or unsubstituted, branched or unbranched heteroaryl. In some embodiments, Ar is unsubstituted heteroaryl. In some embodiments, Ar is substituted heteroaryl.

In some embodiments, Ar is substituted at least at the ortho position. In some embodiments, Ar is substituted at least at the meta position. In some embodiments, Ar is substituted at least at the para position. In some embodiments, Ar is substituted at more than one position. In some embodiments, Ar is substituted with at least one $C_{1-4}$ alkyl. In some embodiments, Ar is substituted with at least one $C_{1-4}$ alkoxy. In some embodiments, Ar is substituted with at least one NO$_2$. In some embodiments, $R^{15}$ is substituted with at least one halogen. In some embodiments, Ar is substituted with at least one O(PG), wherein PG is a hydroxyl protecting group. In some embodiments, Ar is substituted with at least one OH. In some embodiments, Ar is substituted with at least two OH.

In some embodiments $R^{25}$ is substituted or unsubstituted, branched or unbranched aryl. In some embodiments, $R^{25}$ is unsubstituted aryl. In some embodiments, $R^{25}$ is substituted aryl. In some embodiments, R$^{25}$ is unsubstituted phenyl. In some embodiments, R$^{25}$ is substituted phenyl.

In some embodiments R$^{25}$ is substituted or unsubstituted, branched or unbranched heteroaryl. In some embodiments, R$^{25}$ is unsubstituted heteroaryl. In some embodiments, R$^{25}$ is substituted heteroaryl.

In some embodiments, R$^{25}$ is substituted at least at the ortho position. In some embodiments, R$^{25}$ is substituted at least at the meta position. In some embodiments, R$^{25}$ is substituted at least at the para position. In some embodiments, R$^{25}$ is substituted at more than one position. In some embodiments, R$^{25}$ is substituted with at least one C$_{1-4}$ alkyl. In some embodiments, R$^{25}$ is substituted with at least one C$_{1-4}$ alkoxy. In some embodiments, R$^{25}$ is substituted with at least one NO$_2$. In some embodiments, R$^{25}$ is substituted with at least one halogen. In some embodiments, R$^{25}$ is substituted with at least one O(PG), wherein PG is a hydroxyl protecting group. In some embodiments, R$^{25}$ is substituted with at least one OH. In some embodiments, R$^{25}$ is substituted with at least two OH.

In some embodiments R$^{25}$ is substituted or unsubstituted, branched or unbranched heteroaryl.

In some embodiments, R$^{25}$ is a straight chain aliphatic. In some embodiments, R$^{25}$ is a branched chain aliphatic. In some embodiments, R$^{25}$ is a straight chain heteroaliphatic. In some embodiments, R$^{25}$ is a branched chain heteroaliphatic.

In some embodiments, R$^{25}$ is C$_{1-8}$ alkyl, C$_{2-4}$ alkenyl, C$_{2-4}$ alkynyl. In some embodiments, R$^{25}$ is aryl or heteroaryl. In some embodiments R$^{25}$ is acyl.

In some embodiments, R$^{15}$ is C$_{1-4}$ alkyl. In some embodiments, R$^{25}$ is methyl, ethyl, n-propyl, i-propyl, n-butyl, i-butyl, or t-butyl.

In some embodiments, R$^{25}$ is hydrogen.

In some embodiments, Y$^3$ is O. In some embodiments, Y$^3$ is S.

In some embodiments, Y$^4$ is O. In some embodiments, Y$^4$ is S.

In some embodiments, Y$^3$ and Y$^4$ are the same. In some embodiments, Y$^3$ and Y$^4$ are different.

In some embodiments, X$^3$ is O. In some embodiments, X$^3$ is S. In some embodiments, X$^3$ is NR$^{26}$.

In some embodiments, R$^{26}$ is hydrogen. In some embodiments, R$^{26}$ is a nitrogen protecting group. In some embodiments, R$^{26}$ is C$_{1-8}$ alkyl. In some embodiments, R$^{26}$ is heteroaliphatic. In some embodiments, R$^{26}$ is acyl. In some embodiments, R$^{26}$ is aryl or heteroaryl. In some embodiments, R$^{26}$ is alkylamino or dialkylamino.

In some embodiments, R$^{26}$ is alkylhalo.

In some embodiments, X$^4$ is O. In some embodiments, X$^4$ is S. In some embodiments, X$^4$ is NR$^{27}$.

In some embodiments, R$^{27}$ is hydrogen. In some embodiments, R$^{27}$ is a nitrogen protecting group. In some embodiments, R$^{27}$ is C$_{1-8}$ alkyl. In some embodiments, R$^{27}$ is heteroaliphatic. In some embodiments, R$^{27}$ is acyl. In some embodiments, R$^{27}$ is aryl or heteroaryl. In some embodiments, R$^{27}$ is alkylamino or dialkylamino. In some embodiments, R$^{27}$ is alkylhalo.

In some embodiments, a compound of formula IIa can have the structure of formula VII, also referred to herein as 4g6.

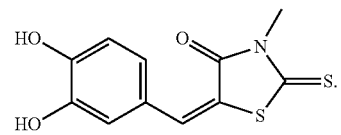

Formula VII

In some embodiments, a compound of formula IIa can have the structure of formula VIII, also referred to herein as 7c7.

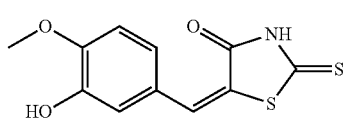

Formula VII

In some embodiments, provided herein are compounds having the structures of formula III, IV, V, VI, or VII. In some embodiments, the compounds provided herein can be used to activate TrpA1 channels or neurons comprising TrpA1 channels in an electromagnetic-dependent manner.

The compound of formula III comprises three rings; a pyridine, a pyrrole, and a rhodanine ring. In some embodiments, the pyridine ring can be unnecessary for photo-sensitive TrpA1 agonist activity. In some embodiments, a photo-sensitive TrpA1 agonist can comprise a pyridine ring. In some embodiments, a photo-sensitive TrpA1 agonist can lack a pyridine ring. In some embodiments, the pyrrole ring, or a close structural analog (e.g. as in formula VII) can be necessary for optimal photo-sensitive TrpA1 agonist activity. In some embodiments, a photo-sensitive TrpA1 agonist can comprise a pyrrole ring. In some embodiments, a photo-sensitive TrpA1 agonist can comprise a structural analog of a pyrrole ring. In some embodiments, a rhodanine ring can be necessary for optimal photo-sensitive TrpA1 agonist activity. In some embodiments, a photo-sensitive TrpA1 agonist can comprise a rhodanine ring. In some embodiments, a photo-sensitive TrpA1 agonist can comprise a rhodanine ring with a nitrogen methylation. In some embodiments, a photo-sensitive TrpA1 agonist can comprise a hydantoin in place of the rhodanine ring. In some embodiments, a photo-sensitive TrpA1 agonist can be unmethylated. As discussed in the Examples herein, the structure of a photo-sensitive TrpA1 agonist can affect the relative potency and duration of effect on activation of a TrpA1 channel after exposure to electromagnetic radiation.

As described herein, photo-sensitive TrpA1 agonists can be specifically activated by particular wavelengths of electromagnetic radiation, i.e. a photo-sensitive TrpA1 agonist will only cause TrpA1 activity when exposed to electromagnetic radiation of an appropriate wavelength. In some embodiments, a photo-sensitive TrpA1 agonist as described herein can be activated when exposed to electromagnetic radiation comprising a wavelength of from about 300 nm to about 700 nm. In some embodiments, a photo-sensitive TrpA1 agonist as described herein can be activated when exposed to electromagnetic radiation comprising a wavelength of from 300 nm to 700 nm. In some embodiments, a photo-sensitive TrpA1 agonist as described herein can be activated when exposed to electromagnetic radiation comprising visible light. In some embodiments, a photo-sensitive TrpA1 agonist as described herein can be activated when exposed to electromagnetic radiation comprising a wavelength of from about 360 nm to about 450 nm. In some embodiments, a photo-sensitive TrpA1 agonist as described herein can be activated when exposed to electromagnetic radiation comprising a wavelength of from about 400 nm to about 440 nm. In some embodiments, a photo-sensitive TrpA1 agonist as described herein can be activated when exposed to electromagnetic radiation comprising a wavelength of from about 400 nm to about 420 nm. It is contemplated that photo-sensitive TrpA1 agonist described herein with structures varying from that of optovin can have different optimum wavelengths for TrpA1 activation. Optimum wavelengths for any such TrpA1 agonist can be determined with no more than routine experimentation by one of ordinary skill in the art. Optovin is selectively activated by violet light and is not activated by other wavelengths. Derivatives that respond to blue, green, red, and infrared light can be selected.

As described herein, photo-sensitive TrpA1 agonists can be bioavailable. In some embodiments, a photo-sensitive TrpA1 agonist, when applied topically, can penetrate the epidermis and be bioavailable to peripheral motor neurons in order to activate the neuron in a photo-dependent manner according to the methods described herein (a property which has been demonstrated on a human subject). In some embodiments, a photo-sensitive TrpA1 agonist can be bioavailable when administered systemically. It is contemplated that, as optovin has been demonstrated to be able to cross the epidermis of humans as well as zebrafish to reach underlying muscles at an effective concentration, that systemic administration of a photo-sensitive TrpA1 agonist can be considered for any method described herein. In some embodiments, oral administration of a photo-sensitive TrpA1 agonist can be considered for any method described herein.

Photo-sensitive TrpA1 agonists can be targeted to specific tissues, areas, and/or neurons by, e.g. localized delivery. In some embodiments, a photo-sensitive TrpA1 agonist can be targeted to specific tissues, area, and/or neurons by e.g. coupling (e.g. covalently bonding or use of a nanosphere composition comprising targeting molecules) the agonist to a targeting molecule. A targeting molecule can be, for example, a nucleic acid, polypeptide, or small molecule which binds to or is bound by a subset of tissues, cell types, and/or neurons. In some embodiments, the targeting molecule can target the photo-sensitive TrpA1 agonist to one or more tissues and/or neurons which it is desired to treat according to the methods described herein. By way of non-limiting example, a photo-sensitive TrpA1 agonist can be targeted to liver tissue by coupling the agonist to e.g., asialoglycoproteins. In some embodiments, the targeting molecule can prevent the photo-sensitive TrpA1 agonist from accumulating in and/or entering one or more non-target tissues and/or neurons. By way of non-limiting example, a photo-sensitive TrpA1 agonist can be coupled to a lipophobic molecule to prevent the agonist from crossing the blood-brain barrier. Further examples of targeting molecules are well known in the art.

The electromagnetic radiation to which the neuron is exposed can be generated by any electromagnetic radiation source capable of generating radiation of the desired wavelength. Non-limiting examples of devices which can be used to generate electromagnetic radiation include a laser, an electromagnetic radiation-emitting diode, a fluorescent or incandescent bulb, and/or the sun. The electromagnetic radiation source can generate radiation consisting of or comprising any of the desired wavelengths of radiation. For example, if the desired wavelength of radiation is from about 400 nm to 420 nm the electromagnetic radiation source can be a laser generating radiation comprising primarily radiation of about 415 nm or the electromagnetic radiation source can be an incandescent bulb generating radiation comprising a multitude of wavelengths, including those of the visible light spectrum and the infrared spectrum. A filter can also serve to spatially-restrict the electromagnetic radiation to which the subject and/or neuron will be exposed.

In some embodiments, the electromagnetic radiation can be passed through a filter prior to contacting the neuron or subject. For example, if an incandescent bulb is the electromagnetic radiation source, the spectrum of radiation produced by the source can be directed through a wavelength-selective filter to reduce the amount of radiation of a non-desired wavelength which contacts the neuron and/or subject.

In some embodiments, the electromagnetic radiation exposure can be widespread or systemic. In some embodiments, the electromagnetic radiation exposure can be localized, e.g. to a tissue or to a spatially-restricted subset of neurons. In some embodiments, the number of channels and/or cells exposed to the radiation can be as few as one channel and/or cell, e.g. at least one channel and/or cell, at least two channels and/or cells, at least 10 channels and/or cells, at least 100 channels and/or cells, at least 1,000 channels and/or cells, or more.

In some embodiments, the electromagnetic radiation exposure can be of an intensity of 1 uW/mm$^2$ or greater, e.g. 1 uW/mm$^2$ or greater, 2 uW/mm$^2$ or greater, 3 uW/mm$^2$ or greater, 5 uW/mm$^2$ or greater, 10 uW/mm$^2$ or greater, 50 uW/mm$^2$ or greater, or 100 uW/mm$^2$ or greater. In some embodiments, the electromagnetic radiation exposure can be of an intensity of 2 uW/mm$^2$ or greater. In some embodiments, the electromagnetic radiation exposure can be of an intensity of from about 1 uW/mm$^2$ to 10 1 uW/mm$^2$ In some embodiments, the electromagnetic radiation intensity can be the intensity of the electromagnetic radiation the target channel and/or neuron experiences. In some embodiments, the electromagnetic radiation intensity can be the intensity of the electromagnetic radiation emitted by the electromagnetic radiation source. In some embodiments, the intensity of the electromagnetic radiation is the intensity of radiation at a wavelength of from about 300 nm to about 700 nm. In some embodiments, the intensity of the electromagnetic radiation is the intensity of radiation at a wavelength of from about 360 nm to about 450 nm. In some embodiments, the intensity of the electromagnetic radiation is the intensity of radiation at a wavelength of from about 400 nm to about 440 nm. In some embodiments, the intensity of the electromagnetic radiation is the intensity of radiation at a wavelength of from about 400 nm to about 420 nm.

In some embodiments, the electromagnetic radiation exposure can be accomplished by illuminating the subject's epidermis. In some embodiments, the electromagnetic radiation exposure can be accomplished by directing the electromagnetic radiation through the epidermis, e.g. illuminating the epidermis with a wavelength of radiation which can, at least in part, penetrate the epidermis or by directing the radiation through the epidermis via a device, e.g. a fiber optic device which penetrates the epidermis. In some embodiments, the electromagnetic radiation can be provided within the subject, e.g. via a surgical incision or via insertion of a probe or means of conducting electromagnetic radiation into the subject via an incision or an orifice. In some embodiments, the electromagnetic radiation exposure can be accomplished by providing an electromagnetic radiation source to the vicinity of the neuron. In some embodiments, the electromagnetic radiation can be caused to illuminate an area in the vicinity of a neuron. As used herein, "the vicinity of the neuron" refers to a distance from the neuron at which the source of electromagnetic radiation can generate electromagnetic radiation which will reach the neuron in sufficient intensity at the appropriate wavelength such that a neuron which comprises at least one TrpA1 channel and which has been exposed to or contacted with a photosensitive TrpA1 agonist as described herein will be activated. The vicinity of the neuron is a distance which is thus dependent upon, for example, the intensity of the electromagnetic radiation generated, the characteristics of the tissue or matter between the radiation source and the neuron, the amount of photo-sensitive TrpA1 agonist to which the neuron was exposed, and the number and concentration of TrpA1 channels which are comprised by the neuron. The vicinity for the neuron for a given set of tissues, electromagnetic radiation sources, neurons, and doses of photo-sensitive TrpA1 agonists can be determined by routine experimentation, e.g. using the assays for efficacy as described elsewhere herein.

In some embodiments, electromagnetic radiation can be provided to the desired channel(s) and/or neuron(s) (i.e. the channel(s) and/or neuron(s) can be illuminated by the electromagnetic radiation) by allowing the electromagnetic source to directly illuminate a channel, neuron, and/or subject without an intervening structure(s) and/or manipulation. By way of non-limiting example, a bulb can be caused to illuminate the skin of the subject. In some embodiments, electromagnetic radiation can be provided to the desired channel(s) and/or neuron(s) by directing the electromagnetic radiation to the desired channel and/or neuron. Materials and devices for directing and/or transmitting electromagnetic radiation are known in the art. A means of directing the electromagnetic radiation can be distinct from the source of the electromagnetic radiation and can allow control of the intensity, location, wavelength, and/or duration of the electromagnetic radiation which ultimately illuminates the channel, neuron, and/or subject. Means of directing the electromagnetic radiation can be include, but are not limited to; illumination of tissue exposed by a surgical incision, fiber optics, implanted fiber optics, microsurgery, endoscope, endoscopic surgery, and/or catheter.

An electromagnetic source and/or means of directing the electromagnetic radiation can be implanted in and/or internalized by the subject. For example, a battery-powered source of electromagnetic radiation can be implanted via surgical incision or internalized (e.g. swallowing or by insertion into the urethra, vagina, or anus).

A consideration in selecting a source of electromagnetic radiation and a means for directing the electromagnetic radiation to the neuron is the degree to which the desired wavelength of electromagnetic radiation can penetrate biological tissues. For example, if the neuron to be activated according to the methods described herein is near the skin, illuminating the epidermis and/or directing a beam of radiation through the epidermis can be sufficient to illuminate the desired neuron. If the neuron is not in close proximity to the epidermis, e.g. if the neuron is a motor neuron controlling the bladder, it can be advantageous to direct the electromagnetic radiation through a probe which can be inserted into the subject's body, thereby reducing the distance the radiation must travel through tissue. The tissue the radiation will be directed through, the intensity of the electromagnetic radiation that is to contact the neuron, and the wavelength of the electromagnetic radiation are further factors that can influence the selection of a source of electromagnetic radiation and a means for directing the electromagnetic radiation to the neuron. The characteristics of electromagnetic radiation traveling through biological tissues have been described in the art, e.g. Stolik et al. Journal of Photochemistry and Photobiology B 2000 57:90-3; Shackley et al. BJU International 2000 86:638-643; which are incorporated by reference herein in their entirety.

In some embodiments, an electromagnetic source can comprise a means of manipulating the characteristics of the electromagnetic radiation, e.g. the duration of the radiation, the frequency of radiation pulses, the intensity of the radiation. The means can include, for example, dials, knobs, digital displays and inputs, or by being coupled to a computer, which can be provided with computer-readable media encoding particular patterns of duration, frequency, and intensity for use in particular applications.

The methods described herein allow two general approaches to modulating the activity of a spatially-restricted subset of neurons and/or channels. In some embodiments, for any purpose described herein, a photo-sensitive TrpA1 agonist can be administered systemically and a localized area of the subject and/or neuron (e.g. the area comprising and/or consisting of a spatially-restricted subset of channels and/or neurons) can be exposed to electromagnetic radiation. Alternatively, in some embodiments, for any purpose described herein, a photo-sensitive TrpA1 agonist can be administered locally (e.g. to the area comprising and/or consisting of a spatially-restricted subset of channels and/or neurons) and part or all of the subject and/or neuron can be exposed to electromagnetic radiation.

Described herein are methods of activating a TrpA1 channel or modulating the activity of a neuron comprising a TrpA1 channel. The methods can comprise: a) contacting the channel and/or neuron with a photo-sensitive TrpA1 agonist as described herein and b) exposing the channel and/or neuron to electromagnetic radiation comprising a wavelength to which the photo-sensitive TrpA1 agonist is responsive to, i.e. a wavelength which will activate the photo-sensitive TrpA1 agonist. In some embodiments, the electromagnetic radiation can comprise radiation of a wavelength of from about 300 nm to 700 nm. In some embodiments, the TrpA1 channel can be comprised by a neuron. In some embodiments, the channel and/or neuron can be comprised by a subject. In embodiments wherein the channel or neuron is comprised by a subject, the methods described herein can allow for activating the channel and/or modulating the activity of the neuron without transgenically altering the subject, i.e. without introducing exogenous nucleic acids and/or proteins to the subject. In some embodiments, the subject can be non-transgenic.

In some embodiments, the methods described herein can allow a spatially-restricted subset of TrpA1 channels and/or neurons comprising a TrpA1 channel to be modulated. As used herein, a "spatially-restricted subset" when used in reference to, e.g. neurons, refers to a subset comprising 1+n neurons (n≥0) where the set of neurons comprises at least n+2 neurons, wherein the neurons in the subset have been selected on the basis of their location. When the activity of a spatially-restricted subset of neurons is modulated, the activity of neurons not in the subset will not be modulated. By way of non-limiting example, a spatially-restricted subset of neurons can comprise the neurons found in a region defined by a 1 cm diameter circle in a muscle tissue. A spatially-restricted subset can be of any 2- or 3-dimensional shape, any size, and can be contiguous or non-contiguous. In some embodiments, the methods of activating a spatially-restricted subset of TrpA1 channels and/or modulating the activity of neurons comprising a TrpA1 channel can comprise contacting only the channels and/or neurons in the subset with a photo-sensitive TrpA1 agonist. By way of non-limiting example, a photo-sensitive TrpA1 agonist can be applied topically only to the area defining the subset of channels and/or neurons which is to be activated and/or modulated. A photo-sensitive TrpA1 agonist can be applied selectively to a subset of channels and/or neurons by any of the methods described herein other than systemic methods, e.g. applied topically, by microsurgery, by injection, or by direct application (e.g. vaginally).

In some embodiments, the methods of activating a spatially-restricted subset of TrpA1 channels and/or modulating the activity of neurons comprising a TrpA1 channel can comprise exposing only the channels and/or neurons in the subset to electromagnetic radiation comprising a wavelength suitable to activate the photo-sensitive TrpA1 agonist. By way of non-limiting example, a neuron and/or subject can be exposed to electromagnetic radiation in the form of a focused beam, e.g. a laser, only in the area defining the subset of channels and/or neurons which is to be activated. The exposure to electromagnetic radiation can be spatially-restricted by, e.g. the use of lasers, the use of shielding devices that are impermeable to electromagnetic radiation, by fiber optics, by microsurgery, or by endoscopic devices. In some embodiments, the population can be a subset of the neurons present in a subject. In some embodiments, only the subset of neurons can be contacted with the compound. In some embodiments, only the subset of neurons can be exposed to the electromagnetic radiation.

In some embodiments, the methods described herein can allow temporal control of the activation and/or modulation of TrpA1 channels and/or neurons comprising a TrpA1 channel. The photo-sensitive TrpA1 agonists described herein can have a transitory effect on the activation of TrpA1 channel that does not persist for extended periods of time once the activating electromagnetic radiation exposure ceases. Thus, activation and/or modulation of a channel and/or neuron can be maintained by maintaining the electromagnetic radiation exposure and activation of a channel and/or neuron can be terminated by terminating the exposure the electromagnetic radiation. Activation and/or modulation of a channel and/or neuron can also be performed in a temporal pattern, e.g. a series of pulses, by exposing the channel and/or neuron to electromagnetic radiation, terminating the electromagnetic radiation, and then repeating the exposure and termination of the exposure to electromagnetic radiation. In some embodiments, there is provided herein a method of modulating the activity of a neuron for a selected duration, the method comprising contacting the neuron with a photo-sensitive TrpA1 agonist as described herein and exposing the neuron to electromagnetic radiation wherein the exposing modulates the activity of the neuron and wherein the modulation ends after termination of the electromagnetic radiation exposure. In some embodiments the electromagnetic radiation can comprise radiation of a wavelength of from about 300 nm to about 700 nm. In some embodiments, the activation of the TrpA1 channel will cease within about $1/10^{th}$ to 10 seconds of the termination of the electromagnetic radiation exposure. In some embodiments, the activation of the TrpA1 channel will cease within about ½ to 5 seconds of the termination of the electromagnetic radiation exposure. In some embodiments, the activation of the TrpA1 channel will cease within about 2 seconds of the termination of the electromagnetic radiation exposure.

Described herein are methods of modulating the activity of a neuron by activating at least one TrpA1 channel comprised by the neuron, resulting in activating of the neuron. Activation of neurons, depending upon the identity of the neuron and the intensity and duration of the stimulation, can modulate the neuron's activity, signaling, and/or functional output. As used herein, the "functional output" of a neuron is distinguished from the signaling of the same neuron. The functional output refers to the end result of normal activation of the neuron, e.g. contraction of a muscle when a motor neuron is activated or perception (either consciously or unconsciously) of a sensation when a sensory neuron is activated. A neuron can be signaling, i.e. transmitting a nervous signal without achieving a functional output (e.g. the signal may be of the wrong intensity or neurons and/or tissue downstream of the neuron may not be able and/or sensitive to the signaling activity of the neuron). As used herein, the term "activity" when referring to a neuron can refer to either signaling activity or functional output. In some embodiments, the methods described herein modulate the signaling activity of a neuron. In some embodiments the methods described herein modulate the functional output of a neuron. Modulation of the functional output of a neuron can be due to remodeling of the nervous system. Modulation can refer either to an increase or decrease in activity, signaling, and/or functional output. In some embodiments, a mild stimulus can activate a neuron. In some embodiments, a stronger stimulus can functionally ablate a neuron, preventing any change in the activation status of the neuron. In some embodiments, a strong stimulus can ablate a neuron due to excitotoxicity as described herein. In some embodiments, a stimulus can modulate neuronal signaling pathways by modulating spike-time dependent plasticity, a natural process that adjusts the strength of connections between neurons on the basis of the timing difference between a neuron's output and input action potentials.

TrpA1 activation has been implicated in antinociceptive effects, (e.g. Andersson et al. Nature Communications 2011 2:1559; which is incorporated by reference herein in its entirety). In some contexts, TrpA1 activation has been implicated in the perception and/or transmittal of painful stimuli. Stimulation of nerves can ultimately result in pain relief, a technique well known in the art and referred to as hyperstimulation analgesia. Hyperstimulation analgesia encompasses techniques such as acupuncture, ice packs, or chemical irritants. Accordingly, in some embodiments, the methods described herein can relate to treatments for pain and/or inflammation, the method comprising contacting the neuron with a photo-sensitive TrpA1 agonist as described herein and exposing the neuron to electromagnetic radiation. In some embodiments, the electromagnetic radiation can comprise a wavelength of from about 300 nm to about 700 nm. In some embodiments, the activity of the neuron is modulated. In some embodiments, the activity of a sensory neuron can be functionally ablated. In some embodiments, a sensory neuron can be ablated. In some embodiments, the activity of a sensory neuron can be increased. In some embodiments, the functional output of a sensory neuron can be decreased, e.g. by at least 10%, i.e. by 10% or more, 20% or more, 30% or more, 50% or more, 70% or more, or 90% or more. In some embodiments, the neuron can be a neuron of a subject in need of treatment for pain or inflammation Examples of conditions involving pain and/or inflammation which can be treated according to the methods described herein include, but are not limited to; chronic pain, back pain, lower back pain, pain resulting from trauma, phantom limb pain, diabetes, brachial plexus injury, neurovascular compression, herniated disc, herniated lumbar disc, herniated lumbar disc with radicular pain, Guillain-Barre syndrome, Charcot-Marie-Tooth disease, amytrophic lateral sclerosis, autoimmune peripheral neuropathies, brachial plexus injury, cervical root avulsion injury, neurovascular compression syndromes, trigmeninal neuralgia, and/or hemifacial spasm. In some embodiments, the pain can be neuropathic pain.

In some embodiments, the nerves at a location afflicted by pain and/or inflammation can be treated and/or their activity modulated according to the methods described herein. In some embodiments, the nerves connecting a location afflicted by pain and/or inflammation to the central nervous system can be treated according to the methods described herein. In some embodiments, the pain can be neuropathic pain. In some embodiments, the pain is neuropathic pain arising as a symptom of diabetes. In some embodiments, the pain is pain in the peripheral appendicular structures.

In some embodiments, the treatment described herein can be administered to the subject while the subject and/or the area of the subject afflicted by pain and/or inflammation is anesthetized. In some embodiments, a neuron can be exposed to electromagnetic radiation while the area comprising the neuron is anesthetized. In some embodiments, a neuron can be contacted with the compound while the area comprising the neuron is anesthetized.

In some embodiments, pain can be physiological pain, protective pain, inflammatory pain, and/or neuropathic pain. In some embodiments, pain can be acute pain. In some embodiments, pain can be chronic pain. Chronic pain can arise from a number of causes. Non-limiting examples of types of chronic pain and/or conditions which can cause chronic pain include, diabetes, uremia, AIDs, nutritional deficiencies, a malfunction in the nervous system (i.e. neuropathic pain), atherosclerosis, systemic lupus erythematous, scleroderma, sarcoidosis, rheumatoid arthritis, polyarteritis nodosa, compression, entrapment, direct trauma, penetrating injuries, contusions, fractured or dislocated bones, tumors, intraneural hemorrhages, exposure to cold and/or radiation, staying in one position too long, constant or acute pressure on any peripheral nerve, traumatic peripheral nerve injury, painful peripheral neuropathy, post herpetic neuralgia, shingles, reflex sympathetic dystrophy, fibromyalgia, failed back surgery syndrome, disc herniation, epidural scarring, arachnoiditis, chronic pelvic pain syndrome, occipital neuralgia, back pain, and/or cardiac pain.

In some embodiments, the pain to be treated according to the methods described herein is phantom limb pain and/or maladaptive CNS plasticity. In some embodiments, the phantom limb pain can be treated by modulation of the afferent signaling neurons affected by the amputation. In some embodiments, the treatment according the methods described herein is initiated soon after the amputation, e.g. within 3 months of the amputation, within 2 months of the amputation, within 1 month of the amputation, within 2 weeks of the amputation, within 1 week of the amputation, or within 1 day of the amputation.

In some embodiments, the subject has or is diagnosed has having a herniated lumbar disc with radicular pain. In such embodiments, the nerve modulated according to the methods described herein can be a nerve leading to a lower extremity. In some embodiments, the nerve modulated according to the methods described herein can be a peripheral nerve. In some embodiments, the nerve modulated according to the methods described herein can be a peripheral nerve suffering from neural compression. In some embodiments, the nerve modulated according to the methods described herein can be a nerve in the neural foramina.

In some embodiments, neurovascular compression syndromes (e.g. trigmeninal neuralgia and/or hemifacial spasm) can be treated by modulating the activity of a cranial nerve in a subject whose tortuous blood vessels have come in contact with the dorsal root entry zone.

Subjects with spinal cord injuries can benefit from neural stimulation, both with respect to a) maintaining muscle tone and general health (e.g. by inducing muscle contraction as discussed elsewhere herein) and b) in regaining function and control of affected areas of their anatomy. Electrical stimulation of damaged neurons can enhance and/or induce healing, growth, repair and/or regeneration of those neurons, and/or restore functionality of those neurons (see, e.g. Brushart et al. Journal of Neuroscience 2002 22:6631-6638; which is incorporated by reference herein in its entirety). Accordingly, provided herein are methods of enhancing and/or inducing neuronal healing comprising contacting the neuron with a photo-sensitive TrpA1 agonist as described herein and exposing the neuron to electromagnetic radiation. In some embodiments, the activity of the neuron can be modulated. In some embodiments, the activity of the neuron can be increased. In some embodiments, the electromagnetic radiation can comprise a wavelength of from about 300 nm to about 700 nm. In some embodiments, the neuron can be a crushed neuron. In some embodiments, the neuron can be a severed neuron. In some embodiments, the neuron can be the neuron of a subject having or in need of treatment for a brachial plexus injury. In some embodiments, the neuron can be the neuron of a subject having or in need of treatment for a spinal cord injury. In some embodiments, the healing or growth of the neuron can be induced and/or enhanced as compared to the healing or growth which occurs in an untreated reference neuron, e.g. at least a 10% increase in healing or growth as compared to an untreated reference neuron. See, e.g. functional electrical stimulation as described in US Patent Publication 2012/0109230 or the FREEHAND device described, e.g. in U.S. Pat. No. 5,167, 229; which publications are incorporated by reference herein in their entireties.

Stimulation and/or activation of particular neurons is known to have therapeutic effects in a variety of conditions. In some embodiments, a neuron can be stimulated and/or activated according to the methods described herein. In some embodiments, the neuron can be the neuron of a subject in need of treatment for epilepsy. In some embodiments, the neuron can be the vagal nerve of a subject in need of treatment for epilepsy. In some embodiments, a source of electromagnetic radiation and/or a means for directing the radiation can be implanted in a subject in need of treatment for epilepsy such that the vagal nerve can be stimulated and/or activated. Methods of vagal nerve stimulation using electric pulse-generating devices is known in the art and can be adapted to administer a photo-sensitive TrpA1 agonist and/or illuminate the neuron as described herein. In some embodiments, the neuron can be a neuron of a subject in need of treatment for seizures. In some embodiments, the neuron can be a neuron in the temporal lobe of a subject in need of treatment for seizures. Devices and methods for monitoring the temporal lobe for seizure activity and then applying an electrical signal to abort/synchronize activity to stop spreading depolarization are known in the art, e.g. NEUROPACE™ (Mountain View, Calif.) and can be adapted to administer a photo-sensitive TrpA1 agonist and/ or illuminate the neuron as described herein.

Dysautonomia is a malfunction of the autonomic nervous system (i.e. the aspect of the nervous system controlling unconscious biological functions). In some embodiments, dysautonomia can be autonomic instability, particularly as it relates to blood pressure and/or vasoactive tone. It is believed that, in at least some cases, autonomic instability and/or dysautonomia symptoms relating to blood pressure can be due to dysfunctional alpha adrengenic receptor signaling. For example, it has been suggested that alpha-1 adrenergic receptor hypersensitivity may be responsible for dysautonomia (see, e.g. Stewart and Erickson emedicine Journal 2002 3:1; which is incorporated by reference herein in its entirety). Accordingly, provided herein is a method of treating autonomic instability by modulating the activity of peripheral autonomic neurons according the methods described herein. In some embodiments, a subject in need of treatment for autonomic instability can be a subject in need of treatment for or diagnosed as having a condition selected from; spinal cord injury, chronic spinal cord injury, acute spinal cord injury, a neurodegenerative disorder, Parkinson's disease, and progressive supranuclear plasy and the like.

Hyperhidrosis is a condition resulting from sympathetic outflow characterized by excessive sweating in various areas of the body. In some embodiments, the sympathetic outflow can be from the thalamus. Current treatments include surgical destruction of the sympathetic cervical ganglia or injection of botulinum toxin every 4-6 months. Accordingly, provided herein is a method of treating hyperhidrosis comprising modulating the activity of the sympathetic cervical ganglia according to the methods described herein.

Spasticity can arise from a number of causes. Cerebral infarcts are often followed by a period of initial flaccidity and then the development of severe spasticity. Current treatments can include physical therapy, botulinum toxin injection, and surgical tendon section. Cerebral palsy subjects display spasticity which can be treated by afferent spinal root section (dorsal segment). Primary or secondary dystonia can result in spasticity which is sometimes treated with deep brain stimulation (of the *globus pallidus internus*). In some embodiments, spasticity arising from, or associated with, any condition can be linked to an imbalance in afferent and efferent signaling. In some embodiments, the imbalance in afferent and efferent signaling can occur in the intrafusal muscle fibers. Accordingly, there is provided herein a method of treating spasticity comprising modulation the activity of a neuron according the methods described herein. In some embodiments, the method can comprise contacting the neuron with a photo-sensitive TrpA1 agonist as described herein and exposing the neuron to electromagnetic radiation. In some embodiments, the functional output of the neuron can increased. In some embodiments, the neuron can be an afferent spinal root neuron. In some embodiments, the neuron can be a neuron of the *globus pallidus internus*. In some embodiments, the electromagnetic radiation can comprise a wavelength of from about 300 nm to about 700 nm. In some embodiments, the activity of a peripheral neuron in the tissue affected by spasticity can be modulated. In some embodiments, the activity of the dorsal root ganglia in the tissue affected by spasticity can be modulated. In some embodiments, the activity of a neuron in the *globus pallidus internus* can be modulated. In some embodiments, the activity of the afferent spinal root can be modulated.

Neuronal ablation is a technique known in the art for treatment of conditions caused by overstimulated, damaged, or dysfunctional nerves. Excessive stimulation of a neuron can result in damage or cell death, a phenomenon known as excitotoxicity. Induced excitotoxicity can therefore be used to therapeutically ablate neurons according to the methods described herein. A dosage combination of photo-sensitive TrpA1 agonist and electromagnetic radiation which is high enough to induce excitotoxicity can be administered to a neuron in need of ablation in accordance with the methods described herein. The methods described herein for neuronal ablation can be used in existing procedures for treating certain conditions. Non-limiting examples of such existing procedures include rhizotomy and cingulotomy. Rhizotomy comprises ablation of the trigeminal nerve and/or spinal nerve roots to treat pain. Cingulotomy comprises ablation of specific nerves in the brain to treat conditions such as obsessive compulsive disorder.

Stimulation of neurons in the brain, (i.e. deep brain stimulation) can provide therapeutic benefit for a number of conditions including Parkinson's disease, dystonia, and essential tremor. Existing methods of performing deep brain stimulation rely upon implantation of a medical device called a 'brain pacemaker' which transmits electrical impulses to selected areas of the brain. For example, the ventrointermediate nucleus of the thalamus can be stimulated to treat essential tremor while the *globus pallidus* or subthalamic nucleus can be stimulated to treat Parkinson's disease or dystonia. Deep brain stimulation has been described in the art, see, e.g. Bersani et al. Eur Psychiatry 2012; Pizzolato and Mandat. Front Integr Neurosci 2012 6:2; Kringelback et al. Nature Review Neruoscience 2007 8:623-635; Gildenberg. Sterotact Funt Neurosurg 2005 83:2-3; Volkmann et al. Mov Disord. 2002 17:S181-7; which are incorporated by reference herein in their entirety. Accordingly, in some embodiments, the methods described herein relate to a method of performing deep brain stimulation in a subject, the method comprising contacting a neuron in the brain with photo-sensitive TrpA1 agonist as described herein and exposing the neuron to electromagnetic radiation. In some embodiments, the electromagnetic radiation can comprise radiation of a wavelength of from about 300 nm to about 700 nm.

The frequency and force of the neuronal stimulation can be controlled by the frequency, localization, duration, and/or intensity of the electromagnetic radiation exposure as well as by the dose, dosing frequency, and/or localization of the photo-sensitive TrpA1 agonist as described herein. For example, a larger dose of the photo-sensitive TrpA1 agonist as described herein can result in stimulation of greater magnitude or a longer duration of electromagnetic exposure can result in a more sustained stimulation. It is contemplated that delivery of the agonist can be accomplished by systemic administration or via catheter. In some embodiments, the electromagnetic radiation can be directed to the neuron by an implanted fiber optic device. Subjects in need of treatment with deep brain stimulation can include subjects having, diagnosed as having, or in need of treatment for a condition selected from the group consisting of: Parkinson's disease, depression, major depression, Alzheimer's disease, stroke recovery, dystonia, traumatic brain injury, impaired gastrointestinal motility, chronic pain, tremor, dystonia, obsessive-compulsive disorder, bipolar disorder, Tourette's syndrome, anorexia nervosa, Lesch-Nyhan syndrome, epilepsy, phantom limb pain, unconsciousness, reduced consciousness, addiction, obesity, and various severe headache syndromes related to sympathetic outflow from the hypothalamus and/or thalamus. In some embodiments, the source of and/or means of directing electromagnetic radiation can be implanted in the subject. By way of non-limiting example, a diode can be implanted in the subject and a fiber optic probe implanted to transmit the electromagnetic radiation to the region of the brain to be stimulated according to the methods described herein. In some embodiments, the electromagnetic source and/or the means of directing electromagnetic radiation can be controlled transcutaneously. In some embodiments, the electromagnetic source and/or the means of directing electromagnetic radiation can be controlled wirelessly. In some embodiments, the electromagnetic source and/or the means of directing electromagnetic radiation, when implanted within the subject, do not comprise a power source, lead, or other aspect of the device which crosses the subject's epidermis. In some embodiments, the neuronal stimulation can inhibit neuron function or dysfunction. In some embodiments, the neuronal stimulation can result in functional "ablation", i.e. the target neuron is, at least temporarily, unable to transmit a nervous system signal but is not subject to cell death. In some embodiments, the neuronal stimulation can alter the neurochemical balance in the neuron and/or the brain, e.g. the concentration and pattern of 5HT and/or dopamine.

Stimulation of neurons, particularly of motor neurons, can cause contraction of a muscle which is a target tissue of the stimulated neuron. Accordingly, in some embodiments, the methods described herein can relate to a method of causing a muscle contraction in a target muscle, the method comprising contacting a neuron in or near the target muscle with a photosensitive TrpA1 agonist as described herein and exposing the neuron to electromagnetic radiation. In some embodiments, the electromagnetic radiation can comprise radiation of a wavelength of from about 300 nm to about 700 nm. In some embodiments, the neuron can be a motor neuron. In some embodiments, the neuron can be a neuron controlling a target muscle, i.e. a neuron, which, when stimulated, will cause contraction in the target muscle. The identity and location of neurons which control particular target muscles is well known in the art, see, e.g. Standring, S. "Gray's Anatomy" 40$^{th}$ edition, Churchill Livingstone 2008; which is incorporated by reference herein in its entirety. In some embodiments, the neuron can be a neuron comprising an axon which contacts the target muscle. In some embodiments, the neuron can innervate the target muscle. In some embodiments, the target muscle can be a smooth muscle, a skeletal muscle, and/or a cardiac muscle. In some embodiments, a nerve which is capable of transmitting signals to the target muscle can be repeatedly stimulated in order to cause the muscle to repeatedly contract. The frequency and force of the muscle contraction can be controlled by the frequency, localization, duration, and/or intensity of the electromagnetic radiation exposure as well as by the dose, dosing frequency, and/or localization of the photo-sensitive TrpA1 agonist as described herein. For example, a larger dose of the photo-sensitive TrpA1 agonist as described herein can result in a more forceful contraction, or a longer duration of electromagnetic exposure can result in a more sustained contraction. In some embodiments, the muscle contraction can be non-voluntary.

Contraction of a muscle(s), depending on the frequency and force of contraction, as well as the identity of the muscle can be directed to a number of possible outcomes. In some embodiments, muscle contraction can improve, enhance, and/or maintain muscle tone. The methods described herein can relate, for example, to improving or maintaining muscle tone in subjects who are mobility impaired, and/or have a reduced ability to exercise a target muscle. Non-limiting examples of such subjects are those who are bed-ridden, suffering from nerve damage, those with spinal cord injuries, those who are subject to extended periods of unconsciousness (e.g. those in comas, both as a result of trauma or injury and those which are medically-induced), or those suffering from a condition which impedes their ability to exercise, (e.g. a neck or head injury, or a broken leg). The methods described herein can also relate to improving and/or maintaining muscle tone in subjects undergoing physical therapy, subjects desiring to augment an exercise regimen, or subjects desiring the aesthetic benefits of improved muscle tone.

In some embodiments, muscle contraction induced by the methods described herein can relate to methods of treating impaired gastrointestinal motility. In some embodiments, impaired gastrointestinal motility can comprise impaired gastrointestinal motility of the upper GI tract. In some embodiments, impaired gastrointestinal motility can comprise impaired gastrointestinal motility of the lower GI tract. In some embodiments, a subject in need of treatment for impaired gastrointestinal motility can be a subject having or diagnosed as having diabetes. In some embodiments, muscles in the gastrointestinal tract, or nerves controlling muscles in the gastrointestinal tract are contacted with a photo-sensitive TrpA1 agonist. In some embodiments, the intestinal and/or subintestinal mucosal surfaces are contacted with a photo-sensitive TrpA1 agonist. In some embodiments, the electromagnetic radiation is provided to the targeted neurons via endoscopy. In some embodiments, the electromagnetic radiation is provided to the targeted neurons via capsule endoscopy. In some embodiments, the electromagnetic radiation is provided to the targeted neurons via wireless capsule endoscopy.

In some embodiments, muscle contraction induced by the methods described herein can relate to methods to induce compliance in a subject. Muscle contraction is currently utilized by, for example, law enforcement as a less-lethal means of subduing a violent or non-compliant subject (e.g. tasers). Described herein is a non-electric method of causing muscle contraction in a subject. A subject contacted with a photo-sensitive TrpA1 agonist as described herein (e.g. as a spray or fluid) can be exposed to electromagnetic radiation of the appropriate wavelength (e.g. from about 300 nm to about 700 nm), thereby inducing non-voluntary muscle contraction in at least one muscle. The subject can be a subject who is non-compliant with a law enforcement officer or a subject who is threatening others with force (e.g. a rioter, a combative patient, etc.). In some embodiments, the subject is an aggressive animal, e.g. an aggressive dog. In some embodiments, multiple subjects can be subdued via muscle contraction as described herein. In some embodiments, the muscle contractions can be painless.

In some embodiments, muscle contraction induced by the methods described herein can relate to a treatment for female sexual dysfunction. Female sexual dysfunction can refer to both hypoorgasmia and anorgasmia. Hypoorgasmia and anorgasmia refer to a reduced rate or lack of orgasm when sufficient sexual stimulation has been experienced. Orgasm itself can comprise muscle contractions of the uterus, vagina, anus, and/or pelvic muscles. Orgasm can also be stimulated by stimulation of nerves in a variety of erogenous tissues, including, but not limited to the clitoris, the vagina, the anus, and the nipples. The erogenous stimulation necessary to achieve orgasm and the experience of orgasm itself can be widely divergent between individuals, and the location and intensity of treatment according to the methods described herein can be directed by the subject's own experience, preferences, and input. A composition comprising a photo-sensitive TrpA1 agonist as described herein can be applied (e.g. by the subject or a sexual partner) to a tissue involved in stimulating or propagating an orgasm. The photo-sensitive TrpA1 agonist can be applied, e.g., topically, intravaginally, or in conjunction with and/or as part of a composition further comprising other substances commonly applied during intercourse or sexual stimulation (e.g. lubricants, spermicides, etc.). The tissue can then be exposed to electromagnetic radiation, thereby inducing muscle contraction. The tissue can be exposed to electromagnetic radiation by using a device for external use, or a probe and/or device for internal (e.g. vaginal) exposure. The electromagnetic radiation source and/or the means of delivering the electromagnetic radiation can be incorporated into devices commonly used during intercourse or sexual stimulation (e.g. vibrators, dildos, etc.). The intensity and frequency of contractions can be varied by the dose of photo-sensitive TrpA1 agonist used, the intensity of the electromagnetic radiation applied, and the frequency and duration of electromagnetic radiation stimulation.

In some embodiments, muscle contraction induced by the methods described herein can relate to modulation of the micturition reflex. In some embodiments, the modulation of the micturition reflex can comprise treating bladder atonia and/or spasm. In some embodiments, the method of modulating the micturition reflex can comprise increasing the activity of the afferent limb of the micturition reflex by activating nerves implicated in the micturition reflex according to the methods described herein. In some embodiments, nerves implicated the micturition reflex can include, but are not limited to, the pelvic splanchnic nerve and sensory neurons located, at least in part, in the prefrontal area and/or the pons. In some embodiments, a subject in need of modulation of the micturition reflex is a subject having or diagnosed as having spinal cord injury.

In some embodiments, a subject in need of modulation of the micturition reflex is a subject in need of treatment for urinary retention or ischuria. Urinary retention can result from a failure of the relevant muscle to contract or to maintain contraction (e.g. intermittent flow, hesitancy, or incomplete voiding symptoms). Causes can be both biological and physical. In some embodiments, a photo-sensitive TrpA1 agonist as described herein can be administered at least to the nerves in or around the bladder (e.g. nerves controlling the bladder wall or the bulbospongious muscle, or the sacral preganglionic neurons) and the neurons can then be exposed to electromagnetic radiation as described herein. In some embodiments, the photo-sensitive TrpA1 agonist can be administered systemically, topically, or via the urethra. In some embodiments, the electromagnetic radiation can be directed through the subject's epidermis or via a probe implanted in the subject. A physician is able to recognize when inducing muscle contraction may not be beneficial to a subject suffering from urinary retention, e.g. such as a subject suffering from a stone or metastasis in in the urethra which blocks the flow of urine from the bladder.

Embodiments of the methods described herein can further comprise methods and devices relating to prosthetic devices, e.g. neuroprosthetics. Current neuroprosthetics can involve the implantation of a neural interface in the brain of a subject in need of a neuroprosthetic (e.g. a subject with a spinal cord injury). The interface can detect neuronal signaling, e.g. the signaling that would have controlled a now amputated limb, and send a signal to a prosthetic device, e.g. a robotic and/or mechanical version of an arm. This approach allows the subject to direct the movement of a prosthetic device merely by thinking about moving the device (see, e.g. Hochberg et al. Nature 2012 485:372-5; which is incorporated by reference herein in its entirety). One disadvantage of some currently used neural interface devices is that they protrude form the head of the subject, putting ght subject at high risk of serious, potentially life-threatening infection. In the case of subjects who have lost the ability to control of one or more of their limbs, e.g. subjects with a spinal cord injury resulting in partial paralysis, the neural interface can be adapted to send electric signals to the subject's own limb, allowing them to control their own limb as they would control a mechanical prosthesis. It is contemplated that the methods described herein could be utilized to cause muscles in a subject's limbs to contract in response to signals detected by a neural interface. In some embodiments, the neural interface can be linked to implanted electromagnetic radiation sources and/or means of directing electromagnetic radiation implanted in or on a limb of the subject. The neural interface can be connected wirelessly or via wires, either implanted in the subject or external to the subject.

Accordingly, provided herein is a method of providing a subject with voluntary control of a target neuron, the method comprising contacting a target neuron with a photosensitive TrpA1 agonist as described herein and exposing the target neuron to electromagnetic radiation wherein the electromagnetic radiation exposure is controlled by an input signal. In some embodiments, the electromagnetic radiation can comprise radiation of a wavelength of from about 300 nm to about 700 nm. In some embodiments, the input signal is the signaling activity of one or more of the subject's central nervous system neurons. In some embodiments, the target neuron is a motor neuron. In some embodiments, prior to administration of the photo-sensitive TrpA1 agonist, the subject can lack the ability to activate the motor neuron.

Described herein is a method of permitting non-ocular perception of electromagnetic radiation. As used herein, "non-ocular perception of electromagnetic radiation" refers to the ability to recognize, detect, or perceive a pattern of electromagnetic radiation independent of the eyes and/or ocular nerve. In some embodiments, the electromagnetic radiation can comprise radiation in the visible or near visible wavelengths (e.g. about 300 nm to about 700 nm). Thus, non-ocular perception can be a way of "seeing" without the use of the eyes, i.e. neurons contacted with the photo-sensitive TrpA1 agonists described herein are capable of serving as photosensors. As used herein, a "pattern of electromagnetic radiation" refers to the two-dimensional shape or figure created on a surface by a beam of electromagnetic radiation to which the surface is not entirely transparent. The pattern of electromagnetic radiation can be comprised by a system of symbols or figures which encode information, e.g. an alphabet or the symbols of Morse code.

In some embodiments, described herein is a method of permitting non-ocular perception of electromagnetic radiation, the method comprising contacting a neuron of a subject with a photo-sensitive TrpA1 agonist as described herein and exposing the neuron to electromagnetic radiation. In some embodiments, the electromagnetic radiation can comprise radiation of a wavelength of from about 300 nm to about 700 nm. In some embodiments, the subject has a disease, disorder, or injury of the optic nerve.

In some embodiments relating to non-ocular perception, the neuron is a peripheral neuron. In some embodiments, at least the epidermis near the peripheral neuron is exposed to the electromagnetic radiation. In some embodiments, the electromagnetic radiation forms a pattern when it illuminates the epidermis of the subject. In some embodiments, the electromagnetic radiation forms a series of patterns over the course of time during which it illuminates the epidermis of the subject.

In some embodiments relating to non-ocular perception, the neuron is a neuron in the subject's thalamus. In some embodiments, the exposure of the neuron to electromagnetic radiation is controlled by a device which can detect electromagnetic radiation, of any wavelength and originating from any source, which is present in the environment surrounding the subject.

In some embodiments, a peripheral nerve can be contacted with a photo-sensitive TrpA1 agonist, thus allowing it to function as a photosensor. In some embodiments, the peripheral nerve can be a sensory neuron. In some embodiments, the peripheral nerve can be in the vicinity of the epidermis, e.g. for a given dose of a photo-sensitive TrpA1 agonist and a given intensity of electromagnetic radiation when the radiation encounters the epidermis, the neuron is close enough to the epidermis for the photo-sensitive TrpA1 agonist present in or around that neuron to be activated by the electromagnetic radiation. In some embodiments, a subject in which non-ocular perception of electromagnetic radiation is permitted according to the methods described herein can be a person with impaired vision, e.g. a blind subject. In some embodiments, the electromagnetic radiation can form a pattern when it illuminates the epidermis of the subject. In some embodiments, the electromagnetic radiation can form a series of patterns over the course of time during which it illuminates the epidermis of the subject.

Visual prosthesis devices have also been constructed which bypass the optic pathway, providing direct electrical stimulation of the thalamus, leading to stimulation of the occipital cortex (see, e.g. Pezaris and Eskandar. Neurosurg Focus 2009 27:E6; which is incorporated by reference herein in its entirety). Such devices or equivalents thereof can be adapted to provide electromagnetic radiation and, optionally a photo-sensitive TrpA1 agonist, to the thalamus, resulting in stimulation of a target neuron in the thalamus. In some embodiments, the photo-sensitive TrpA1 agonist can be administered systemically or locally, independent of the visual prosthesis.

Photo-sensitive TrpA1 agonists described herein can be administered by any delivery method known in the art, including but not limited to, injection; parenteral, intravenous, intramuscular, subcutaneous, transdermal, airway (aerosol), pulmonary, direct application, microsurgery, endoscopic surgery, topically, orally, vaginally and/or by contact with the gastro-intestinal lumen. Given the demonstrated ability of optovin to cross the epidermis of humans as well as zebrafish and permit photo-dependent activation of target neurons/muscles, it is specifically contemplated that a photo-sensitive TrpA1 agonist can be administered systemically for any method described herein. This would agonist to all, or at least a variety of tissues, depending e.g. upon design/modification of the agonist to limit or expand systemic bioavailability such that electromagnetic radiation applied to any desired location would be expected to activate neuronal activity at the site of irradiation. In some embodiments, the photo-sensitive TrpA1 agonist can be administered systemically. In some embodiments, the photo-sensitive TrpA1 agonist can be administered locally. It is contemplated that, as optovin has been demonstrated to be able to cross the epidermis of humans as well as zebrafish to reach underlying muscles at an effective concentration, that systemic administration of a photo-sensitive TrpA1 agonist can be considered for any method described herein.

The term "effective amount" as used herein refers to the amount of a photo-sensitive TrpA1 agonist needed to activate a desired channel and/or neuron in conjunction with a given source and intensity of electromagnetic radiation. The term "therapeutically effective amount" refers to an amount of a photo-sensitive TrpA1 agonist that is sufficient to provide a particular effect when administered to a typical subject, e.g. a sufficient amount of a pharmacological composition to provide the desired effect (e.g. pain relief, muscle contraction, sensation, etc.) in conjunction with a given source and intensity of electromagnetic radiation. An effective amount as used herein would also include an amount sufficient to delay the development of a symptom of a condition, alter the course of a symptom of a disease or condition (for example but not limited to, slowing the progression of a symptom of the disease or condition), or reverse a symptom of the disease or condition. Thus, it is not possible to specify the exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, where desired a dose can be formulated in animal models to achieve a circulating plasma concentration range that includes the IC50 (i.e., the concentration of the compound which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, for example, using murine DRG neurons or zebrafish fin motion as described herein. The dosage can be determined by a physician and adjusted, as necessary, to suit observed effects of the treatment.

In some embodiments, the photo-sensitive TrpA1 agonist can be water-soluble. In some embodiments, the photo-sensitive TrpA1 agonist can be water-soluble at concentrations of 100 μM or greater, e.g. 100 μM or greater, 1 mM or greater, 10 mM or greater. In some embodiments, optovin can be water-soluble at concentrations of 100 μM or greater. In some embodiments, the photo-sensitive TrpA1 agonist can be soluble in DMSO. In some embodiments, the photo-sensitive TrpA1 agonist can be soluble in DMSO at concentrations of 100 μM or greater, e.g. 100 μM or greater, 1 mM or greater, 10 mM or greater. In some embodiments, optovin can be soluble in DMSO at concentrations of 100 μM or greater. It is contemplated herein that variants and/or analogs of the photo-sensitive TrpA1 agonists will have modified solubility and availability characterisitics as compared to, e.g. optovin.

In some embodiments, the technology described herein relates to a pharmaceutical composition comprising a photo-sensitive TrpA1 agonist as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin;

(7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. a photo-sensitive TrpA1 agonist as described herein.

In some embodiments, the pharmaceutical composition comprising a photo-sensitive TrpA1 agonist as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration to a patient, including, but not limited to, administration via DUROS®-type dosage forms, and dose-dumping.

Suitable vehicles that can be used to provide parenteral dosage forms of the photo-sensitive TrpA1 agonists as disclosed are well known to those skilled in the art. Examples include, without limitation: sterile water; water for injection USP; saline solution; glucose solution; aqueous vehicles such as but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a photo-sensitive TrpA1 agonist as disclosed herein can also be incorporated into the parenteral dosage forms of the disclosure, including conventional and controlled-release parenteral dosage forms.

Pharmaceutical compositions comprising a photo-sensitive TrpA1 agonist as described herein can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. In some embodiments, a photo-sensitive TrpA1 agonist can be administered via a patch. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the photo-sensitive TrpA1 agonist can be administered in a sustained release formulation.

Controlled-release pharmaceutical products have a common goal of improving drug performance over that achieved by their non-controlled release counterparts. Ideally, the use of an optimally designed controlled-release preparation in medical treatment is characterized by a minimum of drug substance being employed to achieve the desired effect (e.g. neuronal activation and/or pain relief) in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired effect, and gradually and continually release other amounts of drug to maintain this level of effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the compounds and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic delivery systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy. By way of non-limiting example, if a subject is to be treated for pain or inflammation according to the methods described herein, the subject can also be administered a second agent and/or treatment known to be beneficial for subjects suffering from pain or inflammation. Examples of such agents and/or treatments include, but are not limited to, non-steroidal anti-inflammatory drugs (NSAIDs—such as aspirin, ibuprofen, or naproxen); corticosteroids, including glucocorticoids (e.g. cortisol, prednisone, prednisolone, methylprednisolone, dexamethasone, betamethasone, triamcinolone, and beclometasone); methotrexate; sulfasalazine; leflunomide; anti-TNF medications; cyclophosphamide; pro-resolving drugs; mycophenolate; or opiates (e.g. endorphins, enkephalins, and dynorphin), steroids, analgesics, barbiturates, oxycodone, morphine, lidocaine, and the like.

In certain embodiments, a Trp channel and/or a neuron can be activated as described herein once. In certain embodiments, a Trp channel and/or a neuron can be activated as described herein repeatedly. In some embodiments, the photo-sensitive TrpA1 agonist as described herein can be administered repeatedly. In some embodiments, the channel and/or neuron can be exposed to electromagnetic radiation repeatedly.

For systemic administration, subjects can be administered a therapeutic amount of a composition comprising a photo-sensitive TrpA1 agonist as described herein, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more. A composition comprising a photo-sensitive TrpA1 agonist as described herein can be administered over a period of time, such as over a 5 minute, 10 minute, 15 minute, 20 minute, or 25 minute period. The administration can be repeated, for example, on a regular basis, such as hourly for 3 hours, 6 hours, 12 hours or longer or such as biweekly (i.e., every two weeks) for one month, two months, three months, four months or longer.

In some embodiments, administration of a photo-sensitive TrpA1 agonist can be accompanied by the application of, e.g. sunscreen or other radiation-blocking or radiation-deflecting lotions to restrict modulation of neuronal activity to the desired location.

In some embodiments, after an initial treatment regimen, the treatments (e.g. the activation of a Trp channel and/or neuron) can be administered on a less frequent basis. For example, after treatment biweekly for three months, treatment can be repeated once per month, for six months or a year or longer. Treatment according to the methods described herein can reduce levels of a marker or symptom of a condition, e.g. the degree of pain and/or inflammation by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the photo-sensitive TrpA1 agonist and/or activation of a Trp channel and/or neuron. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more.

The dosage ranges for the administration of a photo-sensitive TrpA1 agonist as described herein and electromagnetic radiation, according to the methods described herein depend upon, for example, the form of the photo-sensitive TrpA1 agonist, its potency, and the extent to which symptoms, markers, or indicators of a condition described herein are desired to be reduced, for example the percentage reduction desired for pain and/or inflammation or the extent to which, for example, muscle contractions are desired to be induced. The dosage should not be so large as to cause adverse side effects, such as pain, neuronal damage, or activating of a TrpA1 channel and/or a neuron after the period in which the activation is desired. Generally, the dosage will vary with the age, condition, and sex of the patient and can be determined by one of skill in the art. The dosage can also be adjusted by the individual physician in the event of any complication.

The efficacy of a given combination (i.e. of a given dosage combination) of a particular dose of a photo-sensitive TrpA1 agonist and (including, for example, the identity of the photo-sensitive TrpA1 agonist, the concentration of the photo-sensitive TrpA1 agonist, the frequency of dosing, the route of administration, etc.) and a particular dose of electromagnetic radiation (including, for example, the intensity of radiation, the means of transmitting the radiation, the frequency of the exposure, etc.) in, e.g. the treatment of a condition described herein, or to induce a response as described herein (e.g. the activation of a neuron) can be determined by the skilled clinician. However, a treatment is considered "effective treatment," as the term is used herein, if any one or all of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. neuron activation or muscle contraction. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the disease, e.g., causing regression of symptoms.

An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. muscle contractions or improvement in muscle tone). It is well within the ability of one skilled in the art to monitor efficacy of administration and/or treatment by measuring any one of such parameters, or any combination of parameters. Efficacy can be assessed in animal models of a condition described herein, for example treatment of a zebrafish as described herein to induce muscle contractions. When using an experimental animal model, efficacy of treatment is evidenced when a statistically significant change in a marker is observed, e.g. the extent of muscle contraction.

In vitro and animal model assays are provided herein which allow the assessment of a given dosage combination of photo-sensitive TrpA1 agonist and electromagnetic radiation. By way of non-limiting example, the effects of a given dosage combination can be assessed by measuring the activity of isolated murine dorsal root ganglia (DRG) sensory neurons after being contacted with a photo-sensitive TrpA1 agonist and exposed to electromagnetic radiation according to the methods described herein. A non-limiting example of a protocol for such an assay is as follows: C57Bl/6 male mice (3-4 weeks old) can be decapitated and DRG dissected into 4° C. Hank's Balanced Salt Solution (HBSS; Gibco). Neurons can then be dissociated using collagenase (1 mg/mL; Worthington) and dispase (5 mg/mL; Gibco) dissolved in HBSS. Neurons can be plated in Neurobasal-A medium (Invitrogen), supplemented with B-27 Supplement (Gibco), L-glutamine (Gibco), and penicillin-streptomycin (Gibco). The neurons can be plated onto coverslips coated with 0.1 mg/mL poly-D-lysine (Sigma) and 5 µg/mL laminin (Sigma). After 24 h, neurons can be washed with assay buffer (HBSS, supplemented with 9 mM HEPES, 11 mM D-glucose, 0.1% fatty-acid free BSA, pH 7.3) and incubated for 1 h with 2 µM Fura2-AM (Invitrogen) with 0.2% pluronic (Invitrogen) in assay buffer in the dark at room temperature. The neurons can then be washed with assay buffer and allowed to equilibrate at room temperature for 30 min prior to imaging. After a 120 s baseline perfusion of assay buffer containing 3.3% DMSO, a photo-sensitive TrpA1 agonist as described herein (e.g. 100 µM optovin) dissolved in the DMSO-assay buffer solution, or the DMSO-assay buffer solution alone as a control, can be perfused onto the neurons for a period of 1 min. Fura-2 is activated with UV-light, and the process of imaging Fura-2 can be enough to activate the photo-sensitive TrpA1 agonist. As a no-light control to ensure that the presence of optovin alone did not cause activation, imaging can be stopped for the 1-minute period of photo-sensitive TrpA1 agonist treatment, and resumed once the solution perfuses back onto the neurons. Following this one-minute period, cells can be perfused with DMSO-assay buffer to remove the agonist, which can be followed by addition of 100 µM mustard oil (in DMSO-assay buffer) to determine the total number of TrpA1-expressing neurons present. Images can be acquired on a Nikon ECLIPSE TI™ microscope (Nikon, Melville, N.Y.). Neurons can be counted as activated if they show a response during the 1-minute activation period.

By way of further non-limiting example, current density amplitudes can be analyzed via whole-cell patch clamping in, e.g. HEK293T cells transfected with TrpA1. For example, HEK293 cells can be plated upon poly-lysine coated cover slips and transiently transfected with, e.g., human TRPA1. Voltage clamp recordings can be made in the whole-cell configuration 48 hours after transfection using glass electrodes with 2-4M ohm resistance when filled with (in mM) 140 CsCl, 2 $Mg_2ATP_3$, 2 MgCl, 5 EGTA, and 10 HEPES (pH adjusted to 7.2 with CsOH) and while bathed at room temperature in extracellular solution containing (in mM) 150 NaCl, 5.4 KCl, 1.8 $CaCl_2$, 1 MgCl, and 5 mM HEPES (pH adjusted to 7.4 with NaOH). A voltage ramp protocol from −80 mV to +80 mV over 400 ms can be repeated every 5 seconds during the following conditions: while the cell is dialyzed by the pipette, followed by at least 60 seconds of illumination with 405 nm light, after which a photo-sensitive TrpA1 agonist as described herein, e.g. optovin at 10 µM containing extracellular solution can be perfused into the bath, followed by 1 minute of illumination. Current elicited at holding potentials of +/−70 mV can be used to characterize TRPA1 activation. Effective dosage combinations will result in increased current density amplitudes in response to positive voltage steps. Further, calcium levels will be elevated in such cells following administration of an effective dosage combination.

The efficacy of a given dosage combination can also be assessed in an animal model, e.g. in zebrafish. For example, zebrafish treated according to the methods described herein to cause contraction of the muscles in a particular fin will demonstrate contraction of that fin upon exposure to electromagnetic radiation. Spinalized animals can also be used in such an assay to determine if the response is voluntary or involuntary. An effective reference dosage combination can include optovin (50 µM) for 1-2 min prior to exposing the animals to laser light stimuli (405 nm, 400 µW $mm_2$) Light stimuli can be generated with a 300-watt xenon bulb housed in a Sutter LAMBDA LS ILLUMINATOR™. A cold mirror (reflectance between 300 nm and 700 nm) on the Sutter illuminator can be used to block wavelengths outside of this range.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention is further illustrated by the following examples which in no way should be construed as being further limiting, The contents of all cited references, including literature references, issued patents, published patent applications, and co-pending patent applications, cited throughout this application are hereby expressly incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Moreover, due to biological functional equivalency considerations, some changes can be made in protein structure without affecting the biological or chemical action in kind or amount. All such modifications are intended to be included within the scope of the appended claims.

The technology described herein is further illustrated by the following examples which should not be construed as limiting.

Some embodiments of the technology described herein can be defined as any of the following numbered paragraphs:

1. A method of modulating the activity of a neuron, the method comprising;
   a) contacting the neuron with a compound of formula Ia, Ib, IIa, or IIb:

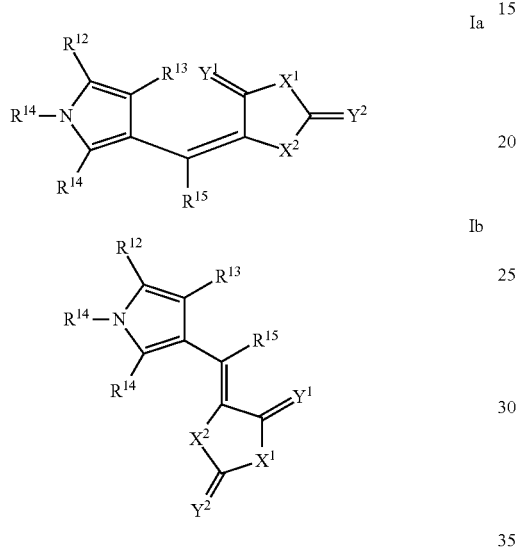

wherein $R^{11}$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$R^{12}$, $R^{13}$, $R^{14}$, and $R^{15}$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; -; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^1$ and $Y^2$ are independently O or S;

$X^1$ is O, NR$^{16}$, or S;

$X^2$ is O, NR$^{17}$, or S; and $R^{16}$ and $R^{17}$ are independently hydrogen; a protecting group; aliphatic; heteroaliphatic; acyl; aryl; alkylhalo; or heteroaryl;

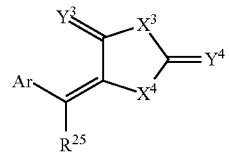

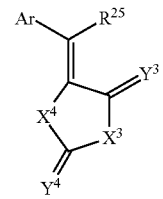

wherein Ar is cyclic substituted or unsubstituted, branched or unbranched aliphatic; cyclic substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $R^{25}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^3$ and $Y^4$ are independently O or S;

$X^3$ is O, NR$^{26}$, or S;

$X^4$ is O, NR$^{27}$, or S;

$R^{26}$ and $R^{27}$ are independently hydrogen; a protecting group; aliphatic; heteroaliphatic; acyl; aryl; alkylhalo; or heteroaryl; and b) exposing the neuron to electromagnetic radiation comprising a wavelength of from about 300 nm to about 700 nm 2. A method of activating a TrpA1 channel, the method comprising;
   a) contacting the channel with a compound of formula Ia, Ib, IIa, or IIb:

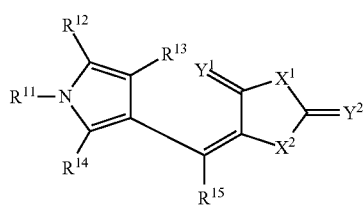

Ia

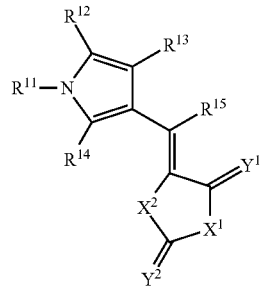

Ib wherein $R^{11}$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2$$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$R^{12}$, $R^{13}$, $R^{14}$ and $R^{15}$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2$$R^B$; -; —CN; —SCN; —SR$^B$; —SOR$^B$; —SO$_2$R$^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^1$ and $Y^2$ are independently O or S;

$X^1$ is O, NR$^{16}$, or S;

$X^2$ is O, NR$^{17}$, or S; and $R^{16}$ and $R^{17}$ are independently hydrogen; a protecting group; aliphatic; heteroaliphatic; acyl; aryl; alkylhalo; or heteroaryl;

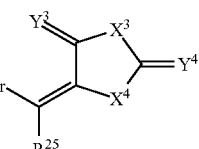

IIa

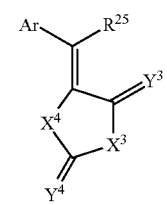

IIb wherein Ar is cyclic substituted or unsubstituted, branched or unbranched aliphatic; cyclic substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $R^{25}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2$$R^B$; —CN; —SCN; —SR$^B$; —SOR$^B$; —SO$_2$R$^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^3$ and $Y^4$ are independently O or S;

$X^3$ is O, NR$^{26}$, or S;

$X^4$ is O, NR$^{27}$, or S;

$R^{26}$ and $R^{27}$ are independently hydrogen; a protecting group; aliphatic; heteroaliphatic; acyl; aryl; alkylhalo; or heteroaryl; and b) exposing the channel to electromagnetic radiation comprising a wavelength of from about 300 nm to about 700 nm 3. A method of modulating the activity of a spatially-restricted subset of neurons in a population of neurons, the method comprising:

a) contacting at least the subset of neurons with a compound of formula Ia, Ib, IIa, or IIb:

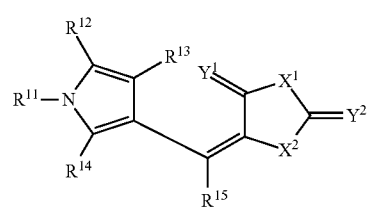

Ia

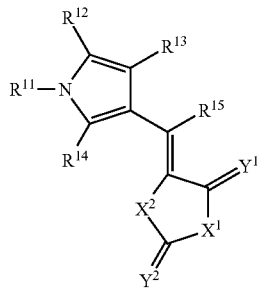

wherein $R^{11}$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$R^{12}$, $R^{13}$, $R^{14}$, and $R^{15}$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; -; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^1$ and $Y^2$ are independently O or S;

$X^1$ is O, NR$^{16}$, or S;

$X^2$ is O, NR$^{17}$, or S; and $R^{16}$ and $R^{17}$ are independently hydrogen; a protecting group; aliphatic; heteroaliphatic; acyl; aryl; alkylhalo; or heteroaryl; and

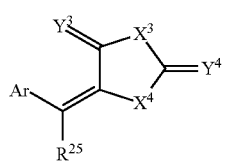

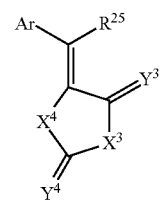

wherein Ar is cyclic substituted or unsubstituted, branched or unbranched aliphatic; cyclic substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $R^{25}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^3$ and $Y^4$ are independently O or S;

$X^3$ is O, NR$^{26}$, or S;

$X^4$ is O, NR$^{27}$, or S;

$R^{26}$ and $R^{27}$ are independently hydrogen; a protecting group; aliphatic; heteroaliphatic; acyl; aryl; alkylhalo; or heteroaryl; and b) exposing at least the subset of neurons to electromagnetic radiation comprising a wavelength of from about 300 nm to about 700 nm 4. The method of paragraph 3, wherein the population of neurons is the neurons present in a subject.
5. The method of paragraph 3, wherein only the subset of neurons is contacted with the compound.
6. The method of paragraph 3, wherein only the subset of neurons is exposed to the electromagnetic radiation.
7. The method of paragraph 3, wherein substantially only neurons contacted with the compound and exposed to the electromagnetic radiation are activated.
8. A method of modulating the activity of a neuron for a selected duration, the method comprising:
   a) contacting the neuron with a compound of formula Ia, Ib, IIa, or IIb:

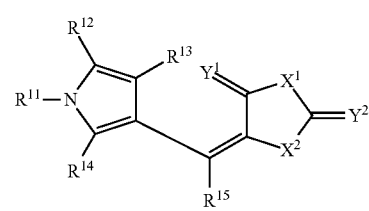

-continued

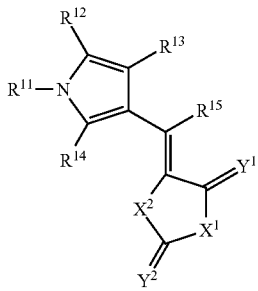

Ib wherein $R^{11}$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$R^{12}$, $R^{13}$, $R^{14}$, and $R^{15}$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; -; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^1$ and $Y^2$ are independently O or S;

$X^1$ is O, $NR^{16}$, or S;

$X^2$ is O, $NR^{17}$, or S; and $R^{16}$ and $R^{17}$ are independently hydrogen; a protecting group; aliphatic; heteroaliphatic; acyl; aryl; alkylhalo; or heteroaryl;

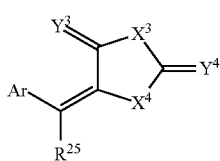

IIa

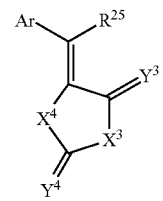

IIb wherein Ar is cyclic substituted or unsubstituted, branched or unbranched aliphatic; cyclic substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $R^{25}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^3$ and $Y^4$ are independently O or S;

$X^3$ is O, $NR^{26}$, or S;

$X^4$ is O, $NR^{27}$, or S;

$R^{26}$ and $R^{27}$ are independently hydrogen; a protecting group; aliphatic; heteroaliphatic; acyl; aryl; alkylhalo; or heteroaryl; and b) exposing the neuron to electromagnetic radiation comprising a wavelength of from about 300 nm to about 700 nm for the selected duration;

wherein the exposing modulates the activity of the neuron; and wherein the modulation ends after termination of the electromagnetic radiation exposure.

9. The method of any of paragraphs 1-8, wherein the activity of the neuron is increased.

10. The method of any of paragraphs 1-8, wherein the functional output of the neuron is decreased.

11. The method of any of paragraphs 1-10, wherein the neuron is functionally ablated.

12. The method of any of paragraphs 1-10, wherein the neuron is ablated.

13. The method of any of paragraphs 1-12, wherein the neuron is a neuron of a subject in need of treatment for pain or inflammation.

14. The method of paragraph 13, wherein the neuron is exposed to electromagnetic radiation while the area comprising the neuron is anesthetized.

15. The method of paragraph 13, wherein the neuron is contacted with the compound while the area comprising the neuron is anesthetized.

16. The method of any of paragraphs 13-15, wherein the pain is neuropathic.

17. The method of any of paragraphs 1-12, wherein the neuron is a neuron of a subject in need of treatment for spinal cord injury.

18. The method of any of paragraphs 1-9 and 17, wherein neuronal healing is induced.

19. The method of any of paragraphs 1-12, wherein the neuron is a neuron of a subject in need of treatment for spasticity.

20. The method of any of paragraphs 1-19, wherein the neuron is the neuron of a subject in need of treatment for a condition selected from the group consisting of: chronic pain; back pain; lower back pain; pain resulting from trauma; phantom limb pain; diabetes; brachial plexus injury; neurovascular compression; herniated disc; herniated lumbar disc; herniated lumbar disc with radicular pain; Guillain-Barre syndrome; Charcot-Marie-Tooth disease; amytrophic lateral sclerosis; autoimmune peripheral neuropathies; brachial plexus injury; cervical root avulsion injury; neurovascular compression syndromes; trigmeninal neuralgia; hemifacial spasm; maladaptive CNS plasticity; epilepsy; seizure; dysautonomia; autonomic instability; hyperhidrosis; obsessive compulsive disorder; spinal cord injury; chronic spinal cord injury; acute spinal cord injury; a neurodegenerative disorder; Parkinson's disease; progressive supranuclear plasy; and dysfunction of the micturition reflex.

21. A method of causing muscle contraction in a target muscle, the method comprising:
a) contacting a neuron controlling a target muscle with a compound of formula Ia, Ib, IIa, or IIb:

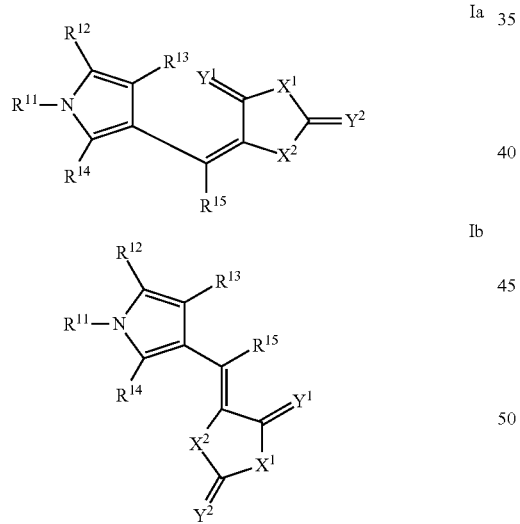

wherein $R^{11}$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$R^{12}$, $R^{13}$, $R^{14}$, and $R^{15}$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; -; —CN; —SCN; —SR$^B$; —SOR$^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^1$ and $Y^2$ are independently O or S;
$X^1$ is O, $NR^{16}$, or S;
$X^2$ is O, $NR^{17}$, or S; and
$R^{16}$ and $R^{17}$ are independently hydrogen; a protecting group; aliphatic; heteroaliphatic; acyl; aryl; alkylhalo; or heteroaryl;

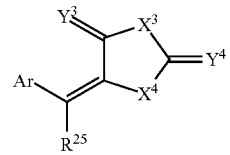

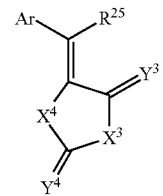

wherein Ar is cyclic substituted or unsubstituted, branched or unbranched aliphatic; cyclic substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $R^{25}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —CN; —SCN; —SR$^B$; —SOR$^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

Y³ and Y⁴ are independently O or S;
X³ is O, NR²⁶, or S;
X⁴ is O, NR²⁷, or S;
R²⁶ and R²⁷ are independently hydrogen; a protecting group; aliphatic; heteroaliphatic; acyl; aryl; alkylhalo; or heteroaryl; and
b) exposing the neuron to electromagnetic radiation comprising a wavelength of from about 300 nm to about 700 nm 22. The method of paragraph 21, wherein the neuron innervates the target muscle.
23. The method of paragraph 21, wherein the neuron is a motor neuron.
24. The method of any of paragraphs 21-23, wherein the target muscle is a muscle selected from the group consisting of:
smooth muscle; skeletal muscle; and cardiac muscle.
25. The method of any of paragraphs 21-24, wherein the muscle contraction enhances muscle tone.
26. The method of any of paragraphs 21-24, wherein the muscle contraction is caused to induce compliance in the subject.
27. The method of any of paragraph 21-24, wherein the muscle contraction is caused to treat anorgasmia.
28. The method of any of paragraphs 21-24, wherein the muscle contraction is caused to treat urinary retention or a dysfunction of the micturition reflex.
29. A method of performing deep brain stimulation, the method comprising:
a) contacting a neuron in the brain with a compound of formula Ia, Ib, IIa, or IIb:

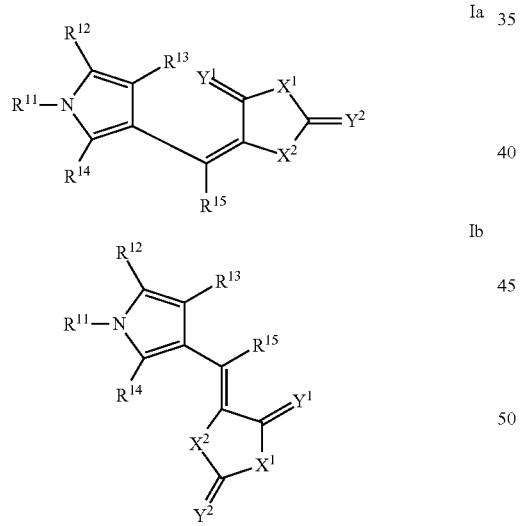

wherein R¹¹ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(═O)R$^B$; —CO₂R$^B$; or —C(R$^B$)₃; wherein each occurrence of R$^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

R¹², R¹³, R¹⁴, and R¹⁵ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(═O)R$^B$; —CO₂R$^B$; -; —CN; —SCN; —SR$^B$; —SOR$^B$; —SO₂R$^B$; —NO₂; —N(R$^B$)₂; —NHC(O)R$^B$; or —C(R$^B$)₃; wherein each occurrence of R$^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;
Y¹ and Y² are independently O or S;
X¹ is O, NR¹⁶, or S;
X² is O, NR¹⁷, or S; and
R¹⁶ and R¹⁷ are independently hydrogen; a protecting group; aliphatic; heteroaliphatic; acyl; aryl; alkylhalo; or heteroaryl;

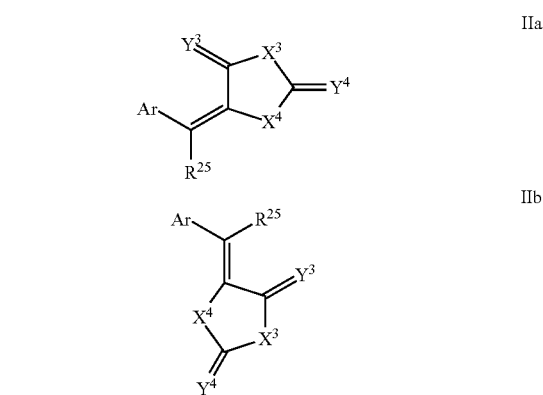

wherein Ar is cyclic substituted or unsubstituted, branched or unbranched aliphatic; cyclic substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; R²⁵ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(═O)R$^B$; —CO₂R$^B$; —CN; —SCN; —SR$^B$; —SOR$^B$; —SO₂R$^B$; —NO₂; —N(R$^B$)₂; —NHC(O)R$^B$; or —C(R$^B$)₃; wherein each occurrence of R$^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^3$ and $Y^4$ are independently O or S;
$X^3$ is O, $NR^{26}$, or S;
$X^4$ is O, $NR^{27}$, or S;
$R^{26}$ and $R^{27}$ are independently hydrogen; a protecting group; aliphatic; heteroaliphatic; acyl; aryl; alkylhalo; or heteroaryl; and b) exposing the neuron to electromagnetic radiation comprising a wavelength of from about 300 nm to about 700 nm 30. The method of paragraph 29, wherein the deep brain stimulation is performed on a subject having a condition selected from the group consisting of:

Parkinson's disease; depression; major depression; chronic pain; tremor; dystonia; obsessive-compulsive disorder; bipolar disorder; Tourette syndrome; Lesch-Nyhan syndrome; epilepsy; phantom limb pain; unconsciousness or reduced consciousness; Alzheimer's disease; stroke; traumatic brain injury; impaired gastrointestinal motility; anorexia nervosa; addiction; obesity; and headache.

31. A method of permitting non-ocular perception of electromagnetic radiation, the method comprising;
a) contacting a neuron of a subject with a compound of formula Ia, Ib, IIa, or IIb:

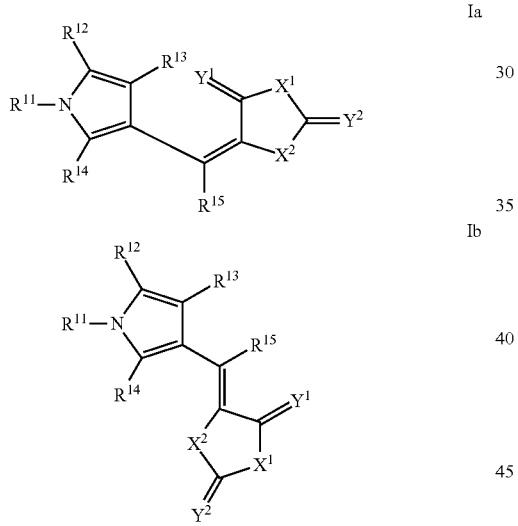

wherein $R^{11}$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$R^{12}$, $R^{13}$, $R^{14}$, and $R^{15}$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; -; —CN; —SCN; —SR$^B$; —SOR$^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^1$ and $Y^2$ are independently O or S;
$X^1$ is O, $NR^{16}$, or S;
$X^2$ is O, $NR^{17}$, or S; and
$R^{16}$ and $R^{17}$ are independently hydrogen; a protecting group; aliphatic; heteroaliphatic; acyl; aryl; alkylhalo; or heteroaryl;

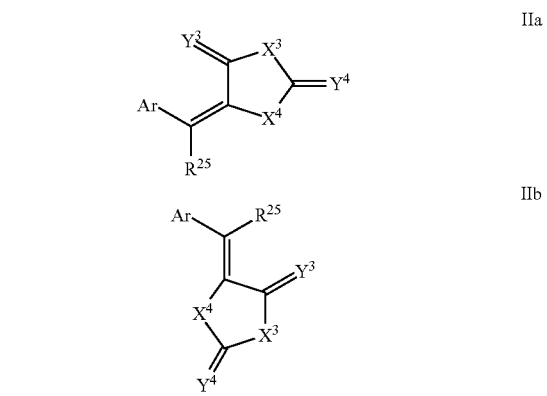

wherein Ar is cyclic substituted or unsubstituted, branched or unbranched aliphatic; cyclic substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $R^{25}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —CN; —SCN; —SR$^B$; —SOR$^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^3$ and $Y^4$ are independently O or S;
$X^3$ is O, $NR^{26}$, or S;
$X^4$ is O, $NR^{27}$, or S;
$R^{26}$ and $R^{27}$ are independently hydrogen; a protecting group; aliphatic; heteroaliphatic; acyl; aryl; alkylhalo; or heteroaryl; and b) exposing the neuron to electromagnetic radiation comprising a wavelength of from about 300 nm to about 700 nm;

whereby said contacting and exposing activate the neuron, generating a sensation perceptible by the subject, whereby electromagnetic radiation is perceived by the subject in a non-ocular manner.

32. The method of paragraph 31, wherein the neuron is a peripheral neuron.

33. The method of paragraph 31, wherein the neuron is a sensory neuron.

34. The method of any of paragraphs 31-33, wherein at least the epidermis near the peripheral neuron is exposed to the electromagnetic radiation.

35. The method of any of paragraphs 31-33, wherein the electromagnetic radiation forms a pattern when it illuminates the epidermis of the subject.

36. The method of any of paragraphs 31-35, wherein the electromagnetic radiation forms a series of patterns over the course of time during which it illuminates the epidermis of the subject.

37. The method of paragraph 31, wherein the neuron is a neuron in the subject's thalamus.

38. The method of any of paragraphs 31 and 37, wherein the exposure of the neuron to electromagnetic radiation is controlled by a device which can detect electromagnetic radiation of any wavelength which is present in the environment surrounding the subject.

39. The method of any of paragraphs 31-38, wherein the subject has a disease, disorder, or injury of the optic nerve.

40. A method of providing a subject with voluntary control of a target neuron, the method comprising:
  a) contacting a target neuron with a compound of formula Ia, Ib, IIa, or IIb:

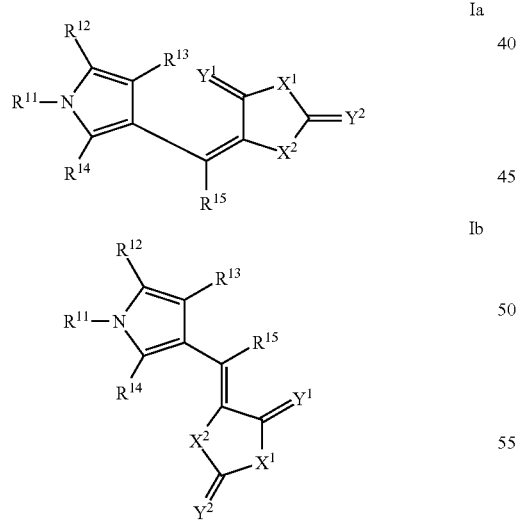

wherein $R^{11}$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$R^{12}$, $R^{13}$, $R^{14}$, and $R^{15}$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; -; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^1$ and $Y^2$ are independently O or S;
$X^1$ is O, NR$^{16}$, or S;
$X^2$ is O, NR$^{17}$, or S; and
$R^{16}$ and $R^{17}$ are independently hydrogen; a protecting group; aliphatic; heteroaliphatic; acyl; aryl; alkylhalo; or heteroaryl;

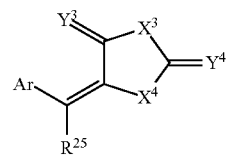

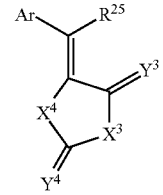

wherein Ar is cyclic substituted or unsubstituted, branched or unbranched aliphatic; cyclic substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $R^{25}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^3$ and $Y^4$ are independently O or S;

$X^3$ is O, $NR^{26}$, or S;

$X^4$ is O, $NR^{27}$, or S;

$R^{26}$ and $R^{27}$ are independently hydrogen; a protecting group; aliphatic; heteroaliphatic; acyl; aryl; alkylhalo; or heteroaryl; and b) exposing the target neuron to electromagnetic radiation comprising a wavelength of from about 300 nm to about 700 nm;

wherein the electromagnetic radiation exposure is controlled by an input signal controlled by the subject.

41. The method of paragraph 40, wherein the input signal is the signaling activity of one or more of the subject's central nervous system neurons.

42. The method of any of paragraphs 40-41, wherein the target neuron is a motor neuron.

43. The method of any of paragraphs 40-42, wherein, prior to administration of the compound, the subject does not have the ability to voluntarily activate the motor neuron.

44. The method of paragraph 43, wherein the subject has a spinal cord injury.

45. The method of any of paragraphs 1-44, wherein the neuron comprises at least one TrpA1 channel.

46. The method of any of paragraphs 1-45, wherein the neuron is a non-retinal neuron.

47. The method of any of paragraphs 1-46, wherein the neuron is a sensory neuron.

48. The method of any of paragraphs 1-47, wherein the neuron is a motor neuron.

49. The method of any of paragraphs 1-48, wherein the subject is not transgenic.

50. The method of any of paragraphs 1-49, wherein the subject is a mammal.

51. The method of any of paragraphs 1-50, wherein the compound is selected from the group consisting of:

Formula III

Formula IV

Formula V

Formula VI

Formula VII

Formula VIII

52. The method of any of paragraphs 1-51, wherein the electromagnetic radiation comprises a wavelength of from about 360 nm to about 450 nm 53. The method of any of paragraphs 1-52, wherein the electromagnetic radiation comprises a wavelength of from about 400 nm to about 440 nm 54. The method of any of paragraphs 1-53, wherein the electromagnetic radiation comprises a wavelength of from about 400 nm to about 420 nm 55. The method of any of paragraphs 1-54, wherein the electromagnetic radiation is provided by a source selected from the group consisting of:

a laser; an electromagnetic radiation-emitting diode; a fluorescent or incandescent bulb; and the sun.

56. The method of any of paragraphs 1-55, wherein the electromagnetic radiation passes through a filter prior to contacting the neuron or the subject.

57. The method of any of paragraphs 1-56, wherein the compound is administered to a subject by a route selected from the group consisting of:

injection; direct application; microsurgery; endoscopic surgery; topically; orally, vaginally, and via contact with the gastro-intestinal lumen.

58. The method of any of paragraphs 1-57, wherein the compound is administered systemically.

59. The method of any of paragraphs 1-57, wherein the compound is administered locally.

60. The method of any of paragraphs 1-59, wherein the compound is administered in a sustained release formulation.

61. The method of any of paragraphs 1-60, wherein the electromagnetic radiation exposure is localized.

62. The method of any of paragraphs 1-61, wherein the electromagnetic radiation exposure is accomplished by illuminating the subject's epidermis.

63. The method of any of paragraphs 1-62, wherein the electromagnetic radiation exposure is accomplished by illuminating a tissue of the subject by directing the electromagnetic radiation through the epidermis.

64. The method of any of paragraphs 1-63, wherein the electromagnetic radiation exposure is accomplished by providing an electromagnetic radiation source to the vicinity of the neuron by a method selected from the group consisting of:

illumination of tissue exposed by a surgical incision; fiber optics; implanted fiber optics; microsurgery;

endoscope; endoscopic surgery; catheter; and an internalized or implanted light.

65. A compound having the structure of formula III:

Formula III

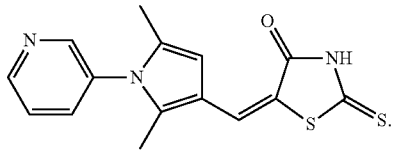

66. A compound having the structure of formula IV:

Formula IV

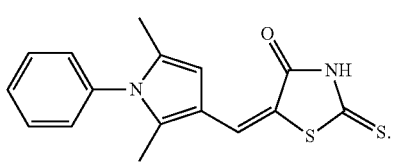

67. A compound having the structure of formula V:

Formula V

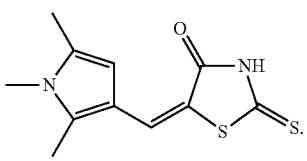

68. A compound having the structure of formula VI:

Formula VI

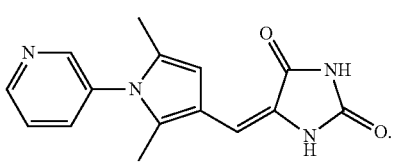

69. A compound having the structure of formula VII:

Formula VII

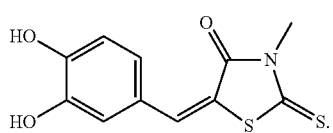

70. A compound having the structure of formula VIII:

Formula VIII

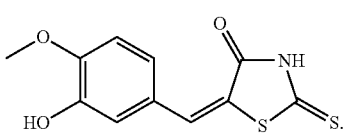

71. A use of a compound of formula Ia, Ib, IIa, or IIb:

Ia

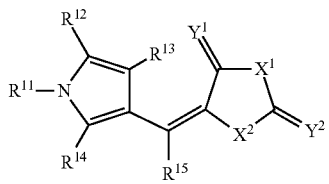

Ib

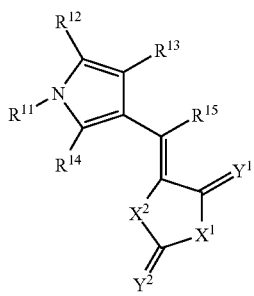

wherein $R^{11}$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$R^{12}$, $R^{13}$, $R^{14}$, and $R^{15}$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; -; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^1$ and $Y^2$ are independently O or S;

$X^1$ is O, N$R^{16}$, or S;

$X^2$ is O, N$R^{17}$, or S; and $R^{16}$ and $R^{17}$ are independently hydrogen; a protecting group; aliphatic; heteroaliphatic; acyl; aryl; alkylhalo; or heteroaryl;

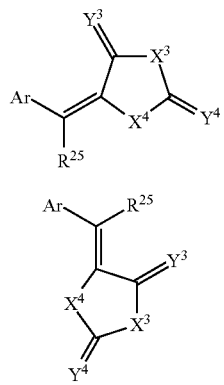

IIa

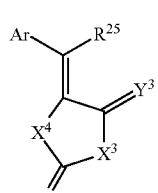

IIb wherein Ar is cyclic substituted or unsubstituted, branched or unbranched aliphatic; cyclic substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $R^{25}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^3$ and $Y^4$ are independently O or S;

$X^3$ is O, $NR^{26}$, or S;

$X^4$ is O, $NR^{27}$, or S;

$R^{26}$ and $R^{27}$ are independently hydrogen; a protecting group; aliphatic; heteroaliphatic; acyl; aryl; alkylhalo; or heteroaryl;

to modulate the activity of a neuron, the use comprising;

a) contacting the neuron with the compound; and b) exposing the neuron to electromagnetic radiation comprising a wavelength of from about 300 nm to about 700 nm 72. The use of a compound of formula Ia, Ib, IIa, or IIb:

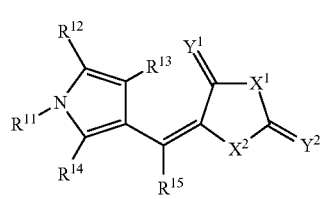

Ia

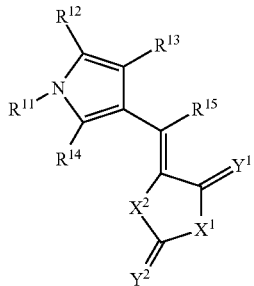

Ib wherein $R^{11}$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$R^{12}$, $R^{13}$, $R^{14}$, and $R^{15}$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; -; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^1$ and $Y^2$ are independently O or S;

$X^1$ is O, $NR^{16}$, or S;

$X^2$ is O, $NR^{17}$, or S; and $R^{16}$ and $R^{17}$ are independently hydrogen; a protecting group; aliphatic; heteroaliphatic; acyl; aryl; alkylhalo; or heteroaryl;

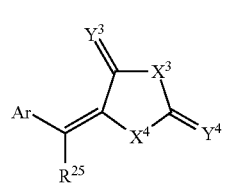

IIa

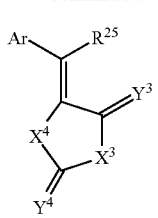

wherein Ar is cyclic substituted or unsubstituted, branched or unbranched aliphatic; cyclic substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $R^{25}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^3$ and $Y^4$ are independently O or S;

$X^3$ is O, NR$^{26}$, or S;

$X^4$ is O, NR$^{27}$, or S;

$R^{26}$ and $R^{27}$ are independently hydrogen; a protecting group; aliphatic; heteroaliphatic; acyl; aryl; alkylhalo; or heteroaryl;

to activate a TrpA1 channel, the use comprising;
a) contacting the channel with the compound; and
b) exposing the channel to electromagnetic radiation comprising a wavelength of from about 300 nm to about 700 nm 73. The use of a compound of formula Ia, Ib, IIa, or IIb:

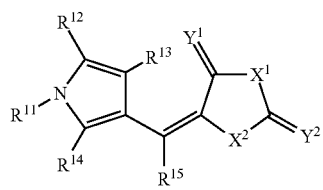

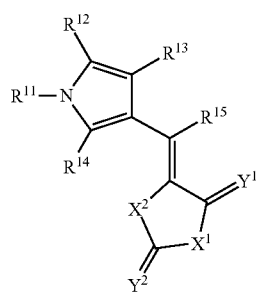

wherein $R^{11}$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$R^{12}$, $R^{13}$, $R^{14}$, and $R^{15}$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; -; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^1$ and $Y^2$ are independently O or S;

$X^1$ is O, NR$^{16}$, or S;

$X^2$ is O, NR$^{17}$, or S; and $R^{16}$ and $R^{17}$ are independently hydrogen; a protecting group; aliphatic; heteroaliphatic; acyl; aryl; alkylhalo; or heteroaryl; and

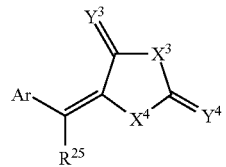

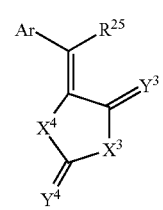

wherein Ar is cyclic substituted or unsubstituted, branched or unbranched aliphatic; cyclic substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $R^{25}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^3$ and $Y^4$ are independently O or S;

$X^3$ is O, $NR^{26}$, or S;

$X^4$ is O, $NR^{27}$, or S;

$R^{26}$ and $R^{27}$ are independently hydrogen; a protecting group; aliphatic; heteroaliphatic; acyl; aryl; alkylhalo; or heteroaryl;

to modulate the activity of a spatially-restricted subset of neurons in a population of neurons, the use comprising:

a) contacting at least the subset of neurons with the compound; and b) exposing at least the subset of neurons to electromagnetic radiation comprising a wavelength of from about 300 nm to about 700 nm 74. The use of paragraph 73, wherein the population of neurons is the neurons present in a subject.

75. The use of paragraph 73, wherein only the subset of neurons is contacted with the compound.

76. The use of paragraph 73, wherein only the subset of neurons is exposed to the electromagnetic radiation.

77. The use of paragraph 73, wherein substantially only neurons contacted with the compound and exposed to the electromagnetic radiation are activated.

78. The use of a compound of formula Ia, Ib, IIa, or IIb:

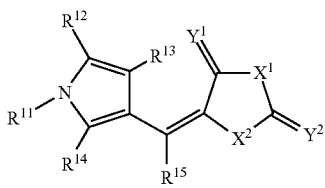

Ia

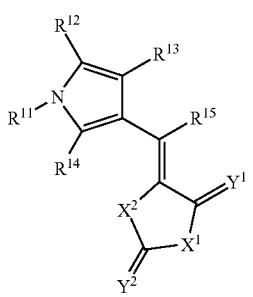

Ib wherein $R^{11}$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$R^{12}$, $R^{13}$, $R^{14}$, and $R^{15}$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; -; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^1$ and $Y^2$ are independently O or S;

$X^1$ is O, $NR^{16}$, or S;

$X^2$ is O, $NR^{17}$, or S; and $R^{16}$ and $R^{17}$ are independently hydrogen; a protecting group; aliphatic; heteroaliphatic; acyl; aryl; alkylhalo; or heteroaryl;

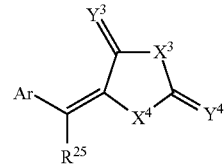

IIa

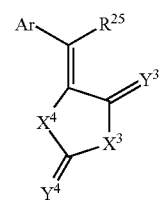

IIb wherein Ar is cyclic substituted or unsubstituted, branched or unbranched aliphatic; cyclic substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $R^{25}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^3$ and $Y^4$ are independently O or S;

$X^3$ is O, $NR^{26}$, or S;

$X^4$ is O, $NR^{27}$, or S;

$R^{26}$ and $R^{27}$ are independently hydrogen; a protecting group; aliphatic; heteroaliphatic; acyl; aryl; alkylhalo; or heteroaryl;

to modulate the activity of a neuron for a selected duration, the use comprising:

a) contacting the neuron with the compound; and b) exposing the neuron to electromagnetic radiation comprising a wavelength of from about 300 nm to about 700 nm for the selected duration;

wherein the exposing modulates the activity of the neuron; and wherein the modulation ends after termination of the electromagnetic radiation exposure.

79. The use of any of paragraphs 71-78, wherein the activity of the neuron is increased.

80. The use of any of paragraphs 71-78, wherein the functional output of the neuron is decreased.

81. The use of any of paragraphs 71-80, wherein the neuron is functionally ablated.

82. The use of any of paragraphs 71-80, wherein the neuron is ablated.

83. The use of any of paragraphs 71-82, wherein the neuron is a neuron of a subject suffering from pain or inflammation.

84. The use of paragraph 83, wherein the neuron is exposed to electromagnetic radiation while the area comprising the neuron is anesthetized.

85. The use of paragraph 83, wherein the neuron is contacted with the compound while the area comprising the neuron is anesthetized.

86. The use of any of paragraphs 83-85, wherein the pain is neuropathic.

87. The use of any of paragraphs 71-82, wherein the neuron is a neuron of a subject has a spinal cord injury.

88. The use of any of paragraphs 71-79 and 87, wherein neuronal healing is induced.

89. The use of any of paragraphs 71-82, wherein the neuron is a neuron of a subject in need of treatment for spasticity.

90. The use of any of paragraphs 71-89, wherein the neuron is the neuron of a subject has a condition selected from the group consisting of:

chronic pain; back pain; lower back pain; pain resulting from trauma; phantom limb pain; diabetes; brachial plexus injury; neurovascular compression; herniated disc; herniated lumbar disc; herniated lumbar disc with radicular pain; Guillain-Barre syndrome; Charcot-Marie-Tooth disease; amytrophic lateral sclerosis; autoimmune peripheral neuropathies; brachial plexus injury; cervical root avulsion injury; neurovascular compression syndromes; trigmeninal neuralgia; hemifacial spasm; maladaptive CNS plasticity; epilepsy; seizure; dysautonomia; autonomic instability; hyperhidrosis; obsessive compulsive disorder; spinal cord injury; chronic spinal cord injury; acute spinal cord injury; a neurodegenerative disorder; Parkinson's disease; progressive supranuclear plasy; and dysfunction of the micturition reflex.

91. The use of a compound of formula Ia, Ib, IIa, or IIb:

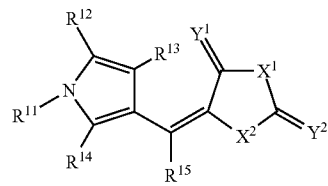

Ia

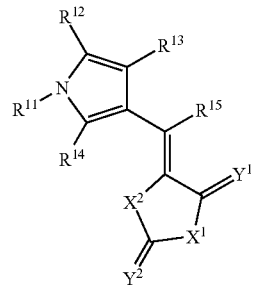

Ib wherein $R^{11}$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$R^{12}$, $R^{13}$, $R^{14}$, and $R^{15}$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; -; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^1$ and $Y^2$ are independently O or S;

$X^1$ is O, $NR^{16}$, or S;

$X^2$ is O, $NR^{17}$, or S; and $R^{16}$ and $R^{17}$ are independently hydrogen; a protecting group; aliphatic; heteroaliphatic; acyl; aryl; alkylhalo; or heteroaryl;

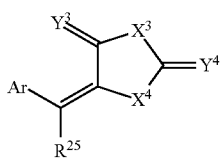

IIa

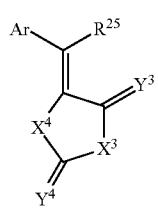

IIb wherein Ar is cyclic substituted or unsubstituted, branched or unbranched aliphatic; cyclic substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $R^{25}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^3$ and $Y^4$ are independently O or S;

$X^3$ is O, N$R^{26}$, or S;

$X^4$ is O, N$R^{27}$, or S;

$R^{26}$ and $R^{27}$ are independently hydrogen; a protecting group; aliphatic; heteroaliphatic; acyl; aryl; alkylhalo; or heteroaryl;

to cause muscle contraction in a target muscle, the use comprising:

a) contacting a neuron controlling a target muscle with the compound; and c) exposing the neuron to electromagnetic radiation comprising a wavelength of from about 300 nm to about 700 nm 92. The use of paragraph 91, wherein the neuron innervates the target muscle.

93. The use of paragraph 91, wherein the neuron is a motor neuron.

94. The use of any of paragraphs 91-93, wherein the target muscle is a muscle selected from the group consisting of:
smooth muscle; skeletal muscle; and cardiac muscle.

95. The use of any of paragraphs 91-294, wherein the muscle contraction enhances muscle tone.

96. The use of any of paragraphs 91-94, wherein the muscle contraction is caused to induce compliance in the subject.

97. The use of any of paragraph 91-94, wherein the muscle contraction is caused to treat anorgasmia.

98. The use of any of paragraphs 91-94, wherein the subject is in need of treatment of urinary retention or a dysfunction of the micturition reflex.

99. The use of a compound of formula Ia, Ib, IIa, or IIb:

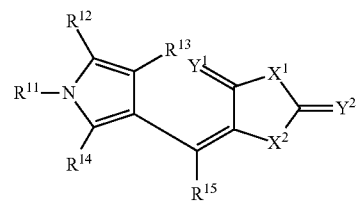

Ia

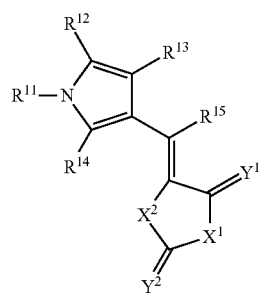

Ia wherein $R^{11}$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$R^{12}$, $R^{13}$, $R^{14}$, and $R^{15}$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; -; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^1$ and $Y^2$ are independently O or S;

$X^1$ is O, N$R^{16}$, or S;

$X^2$ is O, N$R^{17}$, or S; and $R^{16}$ and $R^{17}$ are independently hydrogen; a protecting group; aliphatic; heteroaliphatic; acyl; aryl; alkylhalo; or heteroaryl;

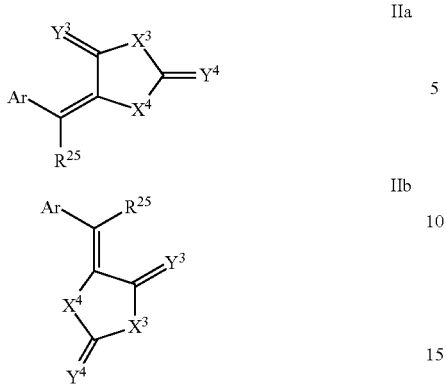

IIa

IIb wherein Ar is cyclic substituted or unsubstituted, branched or unbranched aliphatic; cyclic substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $R^{25}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2$$R^B$; —CN; —SCN; —S$R^B$; —SO$R^B$; —SO$_2$$R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^3$ and $Y^4$ are independently O or S;

$X^3$ is O, $NR^{26}$, or S;

$X^4$ is O, $NR^{27}$, or S;

$R^{26}$ and $R^{27}$ are independently hydrogen; a protecting group; aliphatic; heteroaliphatic; acyl; aryl; alkylhalo; or heteroaryl;

to perform deep brain stimulation, the use comprising:

a) contacting a neuron in the brain with the compound; and b) exposing the neuron to electromagnetic radiation comprising a wavelength of from about 300 nm to about 700 nm 100. The use of paragraph 99, wherein the deep brain stimulation is performed on a subject having a condition selected from the group consisting of:

Parkinson's disease; depression; major depression; chronic pain; tremor; dystonia; obsessive-compulsive disorder; bipolar disorder; Tourette syndrome; Lesch-Nyhan syndrome; epilepsy; phantom limb pain; unconsciousness or reduced consciousness; Alzheimer's disease; stroke; traumatic brain injury; impaired gastrointestinal motility; anorexia nervosa; addiction; obesity; and headache.

101. The use of a compound of formula Ia, Ib, IIa, or IIb:

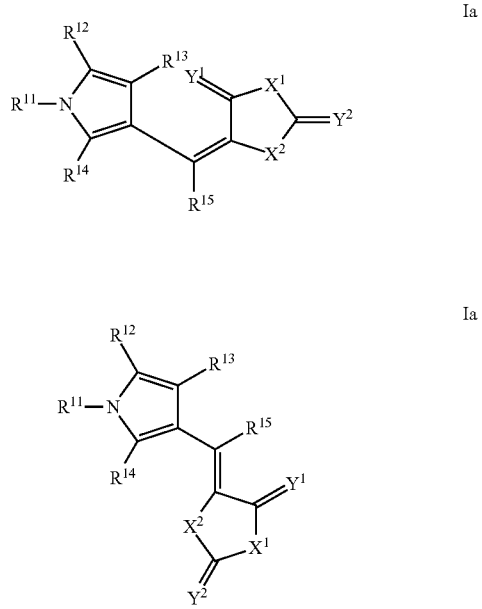

Ia

Ia wherein $R^{11}$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2$$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$R^{12}$, $R^{13}$, $R^{14}$, and $R^{15}$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2$$R^B$; -; —CN; —SCN; —S$R^B$; —SO$R^B$; —SO$_2$$R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^1$ and $Y^2$ are independently O or S;

$X^1$ is O, $NR^{16}$, or S;

$X^2$ is O, $NR^{17}$, or S; and $R^{16}$ and $R^{17}$ are independently hydrogen; a protecting group; aliphatic; heteroaliphatic; acyl; aryl; alkylhalo; or heteroaryl;

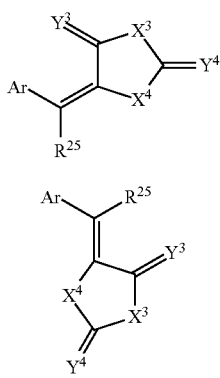

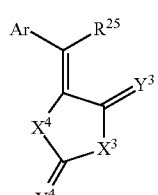

wherein Ar is cyclic substituted or unsubstituted, branched or unbranched aliphatic; cyclic substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $R^{25}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2$$R^B$; —CN; —SCN; —S$R^B$; —SO$R^B$; —SO$_2$$R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$Y^3$ and $Y^4$ are independently O or S;

$X^3$ is O, N$R^{26}$, or S;

$X^4$ is O, N$R^{27}$, or S;

$R^{26}$ and $R^{27}$ are independently hydrogen; a protecting group; aliphatic; heteroaliphatic; acyl; aryl; alkylhalo; or heteroaryl;

to permit non-ocular perception of electromagnetic radiation, the use comprising;

a) contacting a neuron of a subject with the compound; and b) exposing the neuron to electromagnetic radiation comprising a wavelength of from about 300 nm to about 700 nm;

whereby said contacting and exposing activate the neuron, generating a sensation perceptible by the subject, whereby electromagnetic radiation is perceived by the subject in a non-ocular manner.

102. The use of paragraph 101, wherein the neuron is a peripheral neuron.

103. The use of paragraph 101, wherein the neuron is a sensory neuron.

104. The use of any of paragraphs 101-103, wherein at least the epidermis near the peripheral neuron is exposed to the electromagnetic radiation.

105. The use of any of paragraphs 101-103, wherein the electromagnetic radiation forms a pattern when it illuminates the epidermis of the subject.

106. The use of any of paragraphs 101-105, wherein the electromagnetic radiation forms a series of patterns over the course of time during which it illuminates the epidermis of the subject.

107. The use of paragraph 101, wherein the neuron is a neuron in the subject's thalamus.

108. The use of any of paragraphs 101 and 1077, wherein the exposure of the neuron to electromagnetic radiation is controlled by a device which can detect electromagnetic radiation of any wavelength which is present in the environment surrounding the subject.

109. The use of any of paragraphs 101-108, wherein the subject has a disease, disorder, or injury of the optic nerve.

110. The use of a compound of formula Ia, Ib, IIa, or IIb:

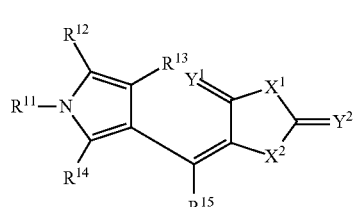

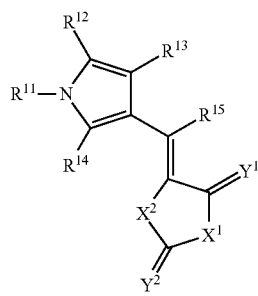

wherein $R^{11}$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2$$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$R^{12}$, $R^{13}$, $R^{14}$, and $R^{15}$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2$$R^B$; -; —CN; —SCN; —S$R^B$; —SO$R^B$; —SO$_2$$R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy;

alkylthioxy; arylthioxy; amino; alkylamino; dialkylamino; heteroaryloxy; heteroarylthioxy; or alkylhalo;
$Y^1$ and $Y^2$ are independently O or S;
$X^1$ is O, $NR^{16}$, or S;
$X^2$ is O, $NR^{17}$, or S; and
$R^{16}$ and $R^{17}$ are independently hydrogen; a protecting group; aliphatic; heteroaliphatic; acyl; aryl; alkylhalo; or heteroaryl;

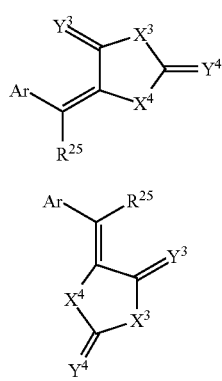

wherein Ar is cyclic substituted or unsubstituted, branched or unbranched aliphatic; cyclic substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $R^{25}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;
$Y^3$ and $Y^4$ are independently O or S;
$X^3$ is O, $NR^{26}$, or S;
$X^4$ is O, $NR^{27}$, or S;
$R^{26}$ and $R^{27}$ are independently hydrogen; a protecting group; aliphatic; heteroaliphatic; acyl; aryl; alkylhalo; or heteroaryl;
to provide a subject with voluntary control of a target neuron, the use comprising:
a) contacting a target neuron with the compound; and
b) exposing the target neuron to electromagnetic radiation comprising a wavelength of from about 300 nm to about 700 nm;
wherein the electromagnetic radiation exposure is controlled by an input signal controlled by the subject.
111. The use of paragraph 110, wherein the input signal is the signaling activity of one or more of the subject's central nervous system neurons.

112. The use of any of paragraphs 110-111, wherein the target neuron is a motor neuron.
113. The use of any of paragraphs 110-112, wherein, prior to administration of the compound, the subject does not have the ability to voluntarily activate the motor neuron.
114. The use of paragraph 113, wherein the subject has a spinal cord injury.
115. The use of any of paragraphs 71-114, wherein the neuron comprises at least one TrpA1 channel.
116. The use of any of paragraphs 71-115, wherein the neuron is a non-retinal neuron.
117. The use of any of paragraphs 71-116, wherein the neuron is a sensory neuron.
118. The use of any of paragraphs 71-117, wherein the neuron is a motor neuron.
119. The use of any of paragraphs 71-118, wherein the subject is not transgenic.
120. The use of any of paragraphs 71-119, wherein the subject is a mammal.
121. The use of any of paragraphs 71-120, wherein the compound is selected from the group consisting of:

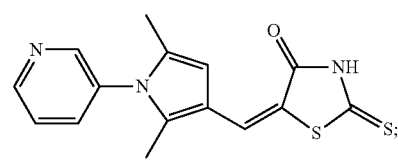

Formula III

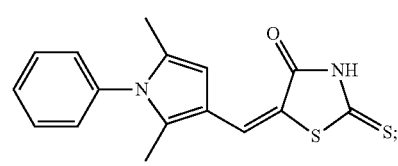

Formula IV

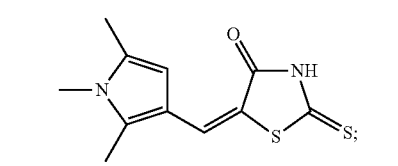

Formula V

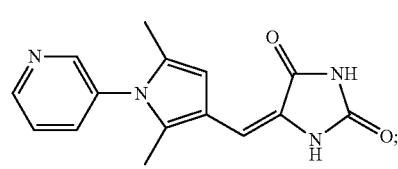

Formula VI

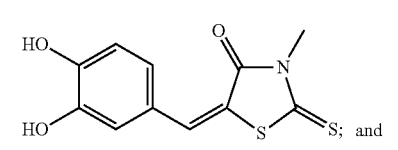

Formula VII

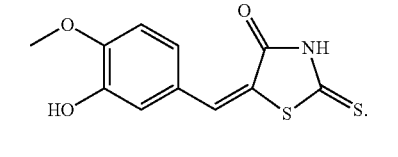

Formula VIII

122. The use of any of paragraphs 71-121, wherein the electromagnetic radiation comprises a wavelength of from about 360 nm to about 450 nm 123. The use of any of paragraphs 71-122, wherein the electromagnetic radiation comprises a wavelength of from about 400 nm to about 440 nm
124. The use of any of paragraphs 71-123, wherein the electromagnetic radiation comprises a wavelength of from about 400 nm to about 420 nm
125. The use of any of paragraphs 71-124, wherein the electromagnetic radiation is provided by a source selected from the group consisting of:
a laser; an electromagnetic radiation-emitting diode; a fluorescent or incandescent bulb; and the sun.
126. The use of any of paragraphs 71-125, wherein the electromagnetic radiation passes through a filter prior to contacting the neuron or the subject.
127. The use of any of paragraphs 71-126, wherein the compound is administered to a subject by a route selected from the group consisting of:
injection; direct application; microsurgery; endoscopic surgery; topically; orally, vaginally, and via contact with the gastro-intestinal lumen.
128. The use of any of paragraphs 71-127, wherein the compound is administered systemically.
129. The use of any of paragraphs 71-127, wherein the compound is administered locally.
130. The use of any of paragraphs 71-129, wherein the compound is administered in a sustained release formulation.
131. The use of any of paragraphs 71-130, wherein the electromagnetic radiation exposure is localized.
132. The use of any of paragraphs 71-131, wherein the electromagnetic radiation exposure is accomplished by illuminating the subject's epidermis.
133. The use of any of paragraphs 71-132, wherein the electromagnetic radiation exposure is accomplished by illuminating a tissue of the subject by directing the electromagnetic radiation through the epidermis.
134. The use of any of paragraphs 71-133, wherein the electromagnetic radiation exposure is accomplished by providing an electromagnetic radiation source to the vicinity of the neuron by a method selected from the group consisting of:
illumination of tissue exposed by a surgical incision; fiber optics; implanted fiber optics; microsurgery; endoscope; endoscopic surgery; catheter; and an internalized or implanted light.

EXAMPLES

Example 1

Identification and Characterization of Optovin

Optogenetics is a powerful research tool because it enables high-resolution optical control of neuronal activity[1-14]. However, current optogenetic approaches are limited to transgenic systems expressing microbial opsins and other exogenous photoreceptors. Identified herein are small molecules, including optovin, that enable repeated photoactivation of motor behaviors in wild type animals. Surprisingly, optovin's behavioral effects are not visually mediated. Rather, photodetection is performed by sensory neurons expressing the cation channel TRPA1. TRPA1 is both necessary and sufficient for the optovin response. Optovin activates human TRPA1 via structure-dependent photochemical reactions with redox-sensitive cysteine residues. In animals with severed spinal cords, optovin treatment enables control of motor activity in the paralyzed extremities by localized illumination. Described herein is the identification of a light-based strategy for controlling endogenous TRPA1 receptors in vivo, with clinical and research applications in non-transgenic animals, including humans.

Results

Figure 1B:
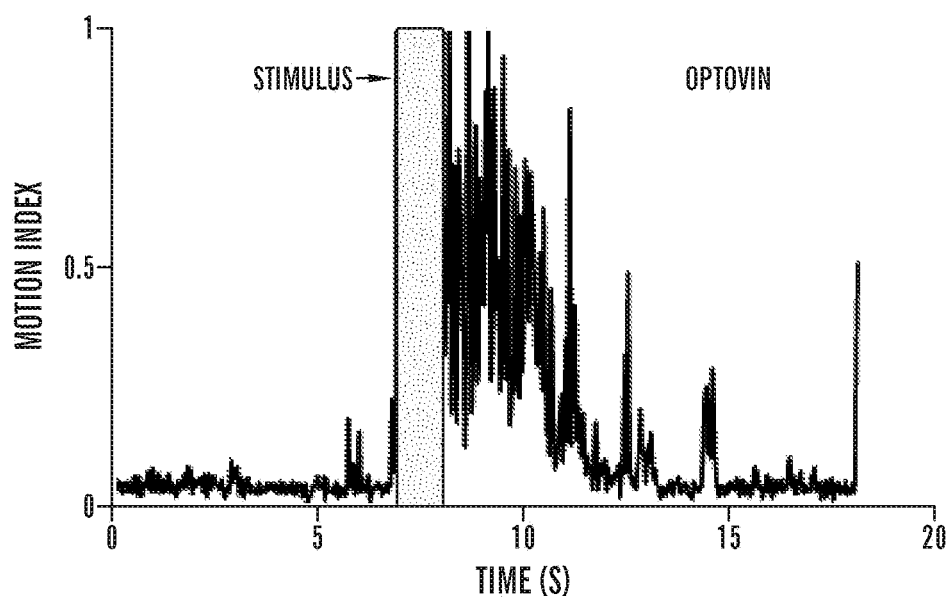
Figure 1C:
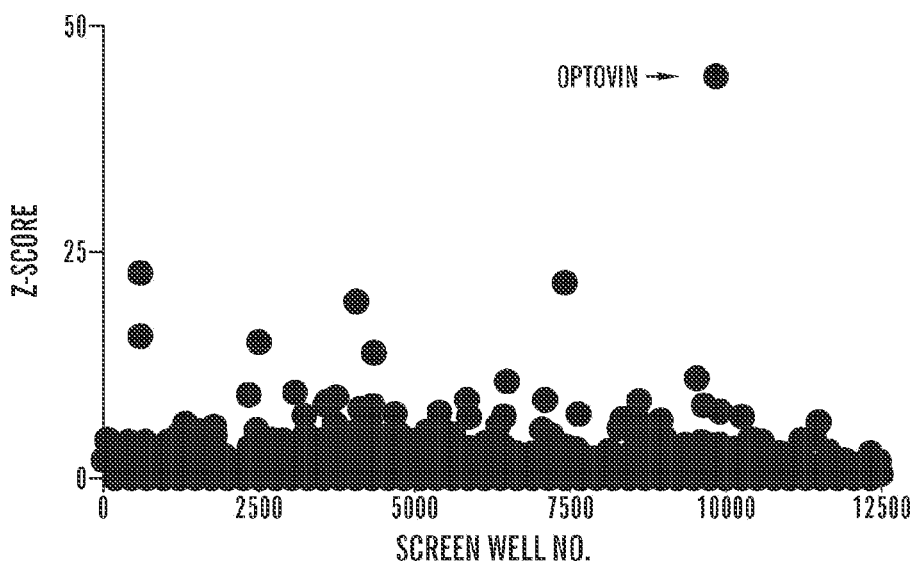

To identify small molecules for the optical control of endogenous channels, a screen was conducted for compounds that could drive light-dependent motor behaviors in wild-type zebrafish. Zebrafish embryos are particularly well suited for phenotype based chemical screens[28,29]. They are blind for the first 3 days of development and other than a one-time motor response to the first light exposure in dark-adapted animals (the photomotor response, PMR), zebrafish embryos are unresponsive to light[31,30] (FIG. 1A). A library of 10,000 structurally diverse synthetic small molecules was screened for compounds that render zebrafish embryos responsive to light. Behavioral responses were measured for each well in comparison to a set of 2,500 DMSO treated controls. This screen identified a single compound, optovin, that increased motor activity greater than 40 standard deviations above the control mean (FIGS. 1A-1C).

Figure 1D:
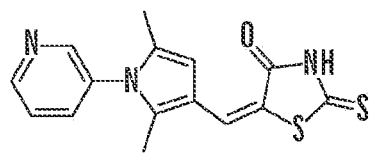
Figure 1E:
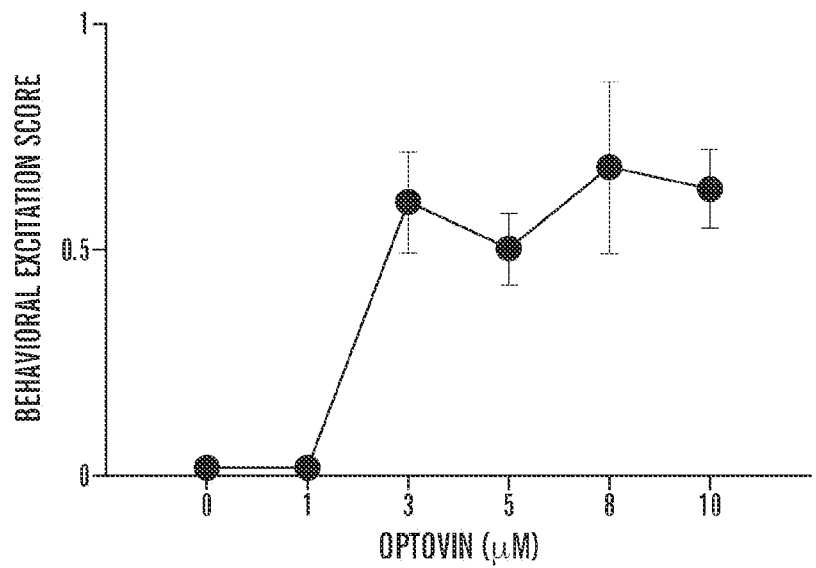
Figure 1F:
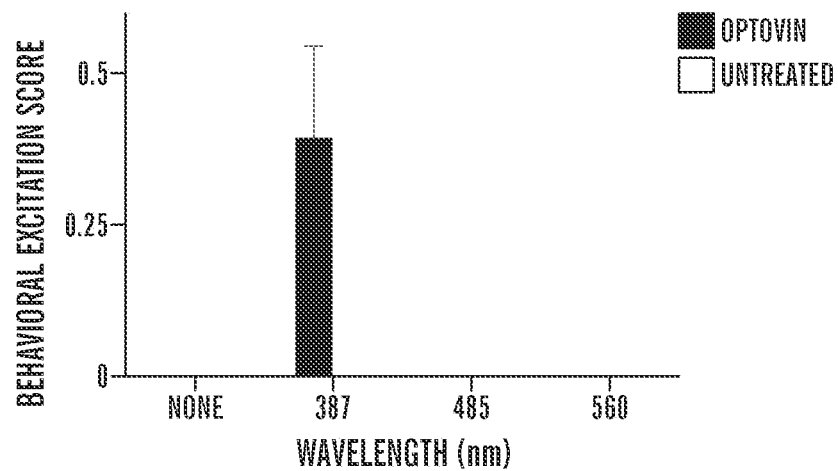
Figure 1G:
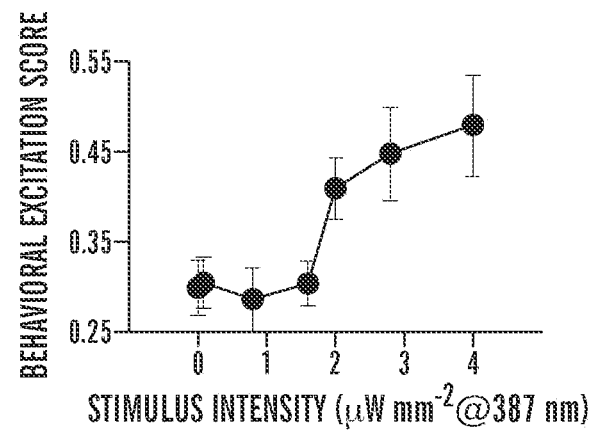
Figure 1H:
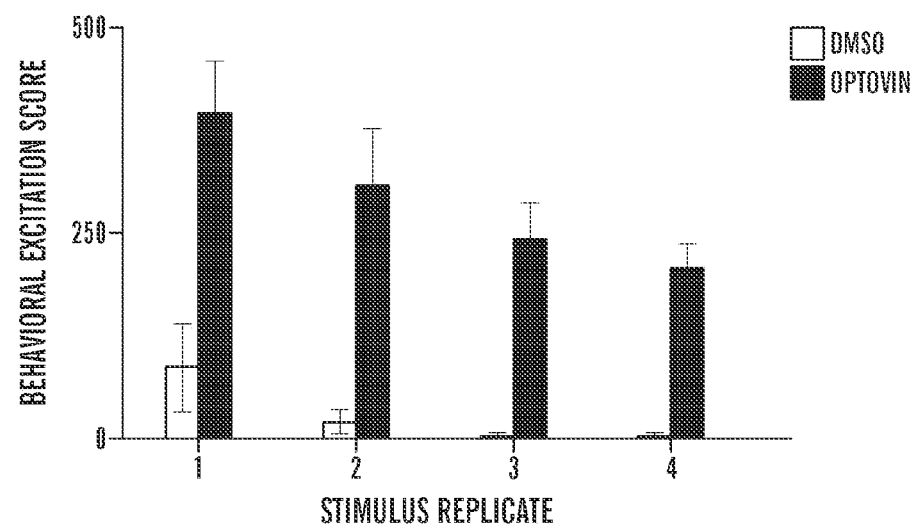
Figure 9A:
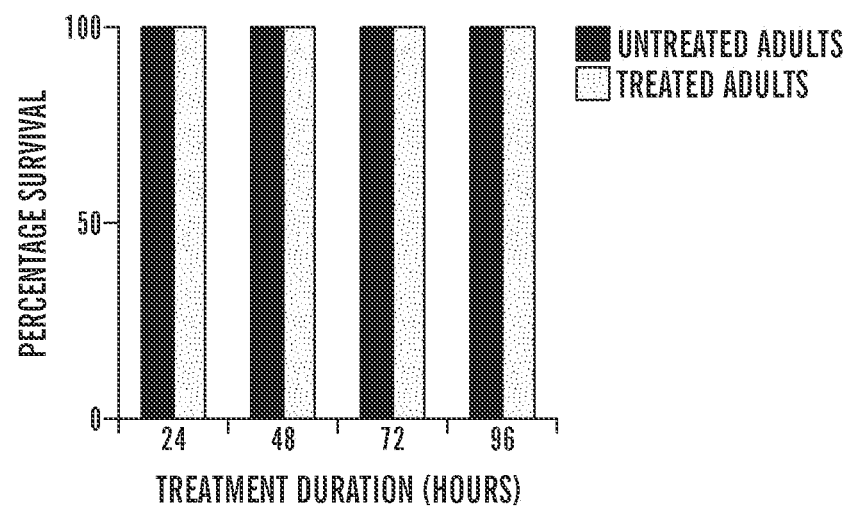
FIGS. 9A-9B demonstrate that Optovin treatment does not affect survival rates in larval or adult zebra fish. Barplots showing the percentage survival of adult (n=2) (FIG. 9A) and larval (n=150) (FIG. 9B) zebrafish after the indicated duration of optovin treatment (10 μM). Differences between groups were not significant, p=0.7.
Figure 9B:
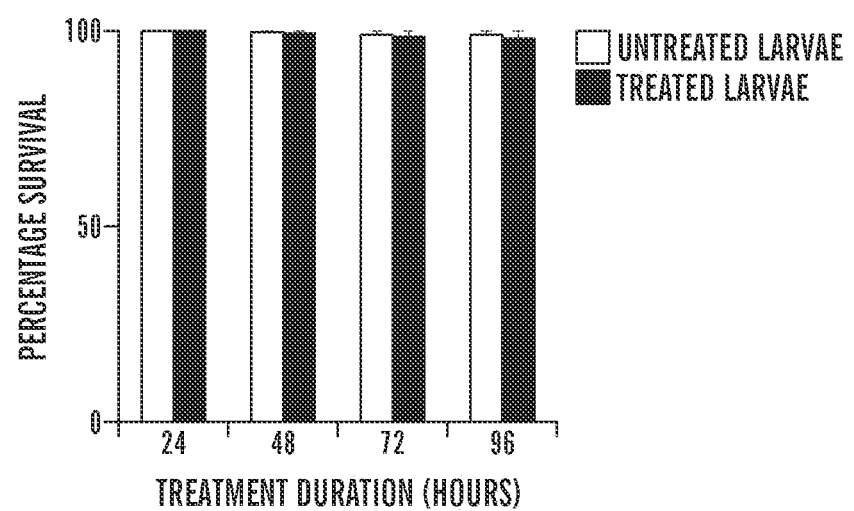

Optovin is a rhodanine-containing small molecule with no previously annotated biological activity (FIG. 1D). Whereas DMSO-treated animals do not respond to photic stimuli, optovin-treated animals respond to light with vigorous motor excitation at an EC50 of 2 µM (FIG. 1E). Optovin-treated animals respond to 387 nm (violet) stimuli, but not to 485 nm (blue), 560 nm (green) or longer wavelengths (FIG. 1F). Motor behavior in optovin-treated animals is elicited by radiation stimulus intensitites greater than 1.6 $\mu W/mm^2$ (FIG. 1G). For radiation stimuli lasting between 5 and 20 seconds, stimulus and response duration are proportional. In treated animals, multiple responses can be triggered with repeated light pulses (FIG. 1H). No signs of toxicity were observed in optovin treated animals, even after 48 hours of treatment. To determine the long-term effects of optovin exposure on development, behavior and survival, the development, behavior and survival of larvae and adult zebrafish exposed to optovin (10 µM) for 96 hours were analyzed. No differences were identified in the appearance, touch response, heart rate, fin movements, morphology or percentage survival between the treated and untreated groups (FIGS. 9A-9B). Thus, optovin is a novel behavior-modifying compound that causes rapid and reversible motor excitation in response to violet light stimuli.

Figure 1I:
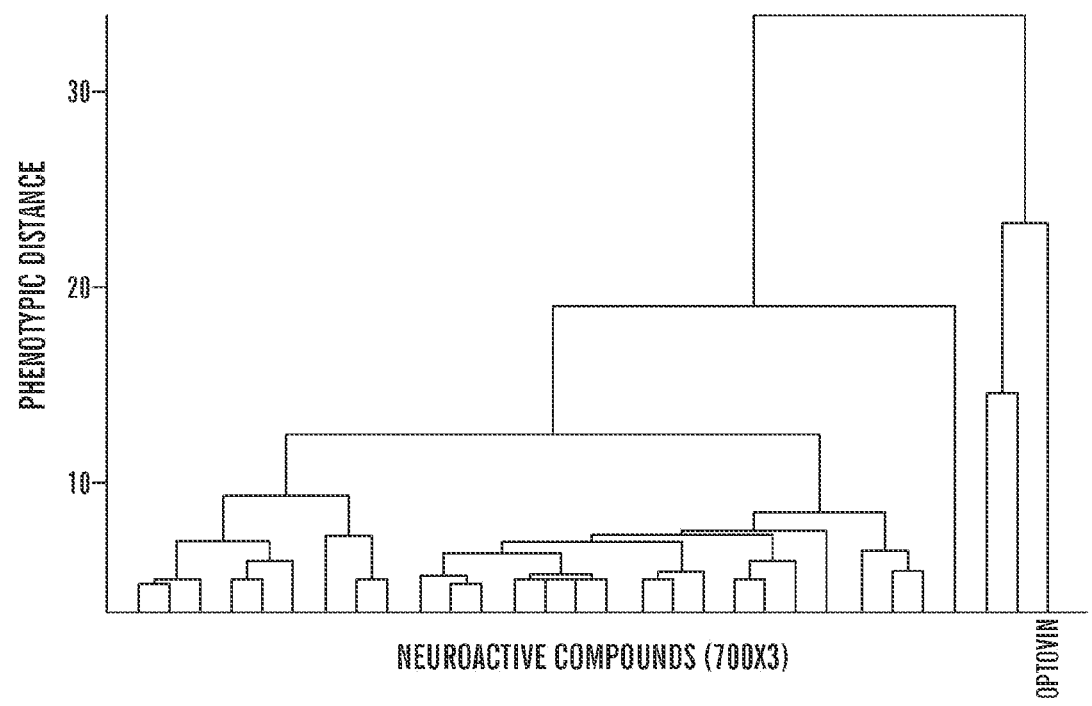

To determine if optovin's mechanism of action could be predicted via behavioral profiling[30,32], optovin's behavioral profile was compared to the behavioral profiles of 700 annotated neuroactive compounds tested in triplicate. These compounds include ligands targeting the adrenergic, serotonergic, histaminergic, dopaminergic, cholinergic and glutamatergic pathways. Hierarchical clustering shows that the optovin phenotype is dissimilar to phenotypes caused by the annotated compounds, and clusters on a separate branch of the dendrogram (FIG. 1I). These data indicate that optovin is functionally distinct from the known neuroactive compounds tested. To gain insight into optovin's mechanism of action, optovin and two active optovin analogs were profiled using the National Institutes of Mental Health Psychoactive Drug Screening Program (NIMH PDSP) to determine their activities against a panel of human and rodent CNS receptors, channels and transporters. No sub-micromolar binding targets were identified for these compounds (Tables 1 and 2), suggesting that optovin may act through a mechanism of action not represented in the extensive NIMH-PDSP collection.

Figure 2A:
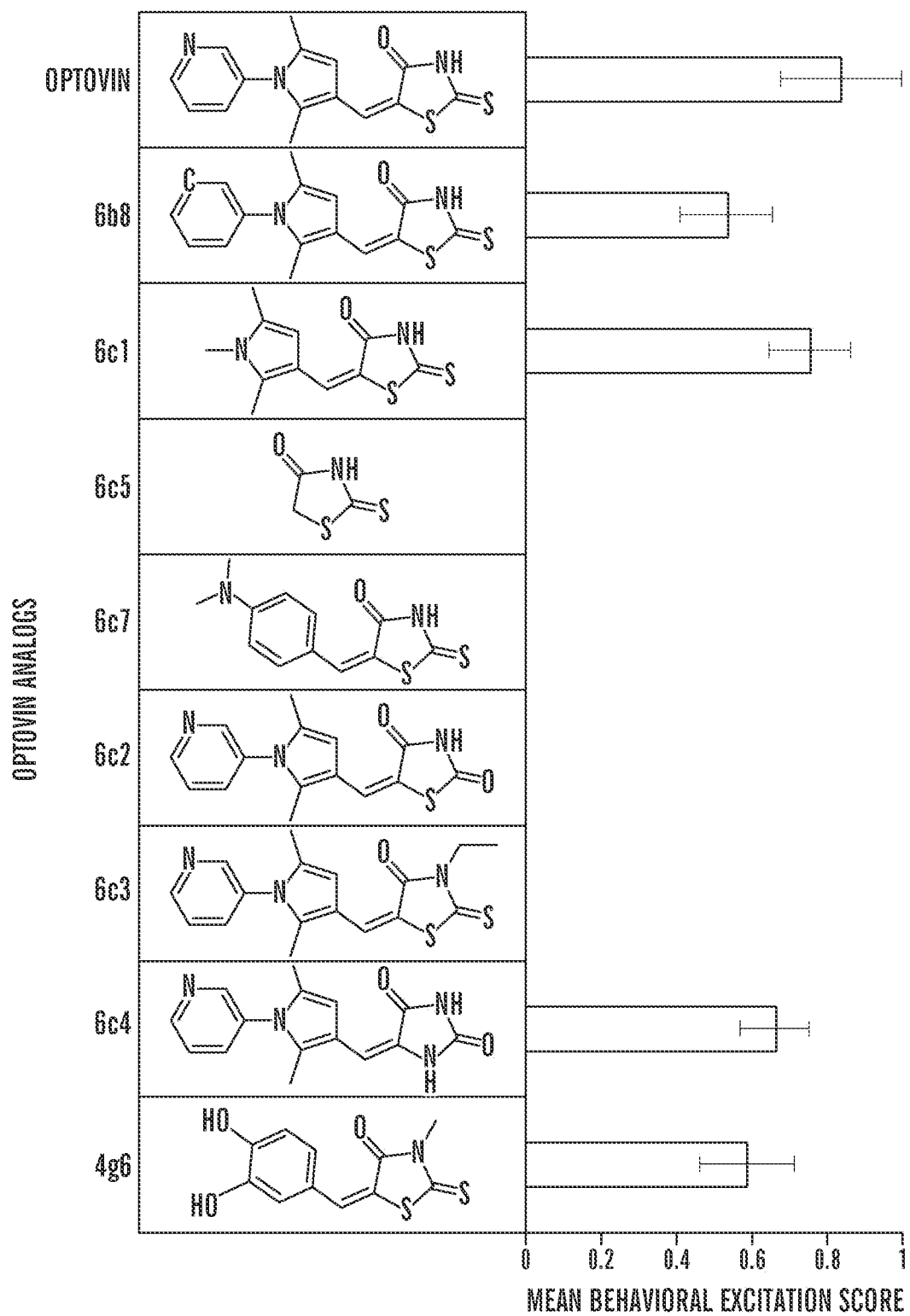
FIGS. 2A-2C portray the results of optovin structure activity relationship analysis.
Figure 2B:
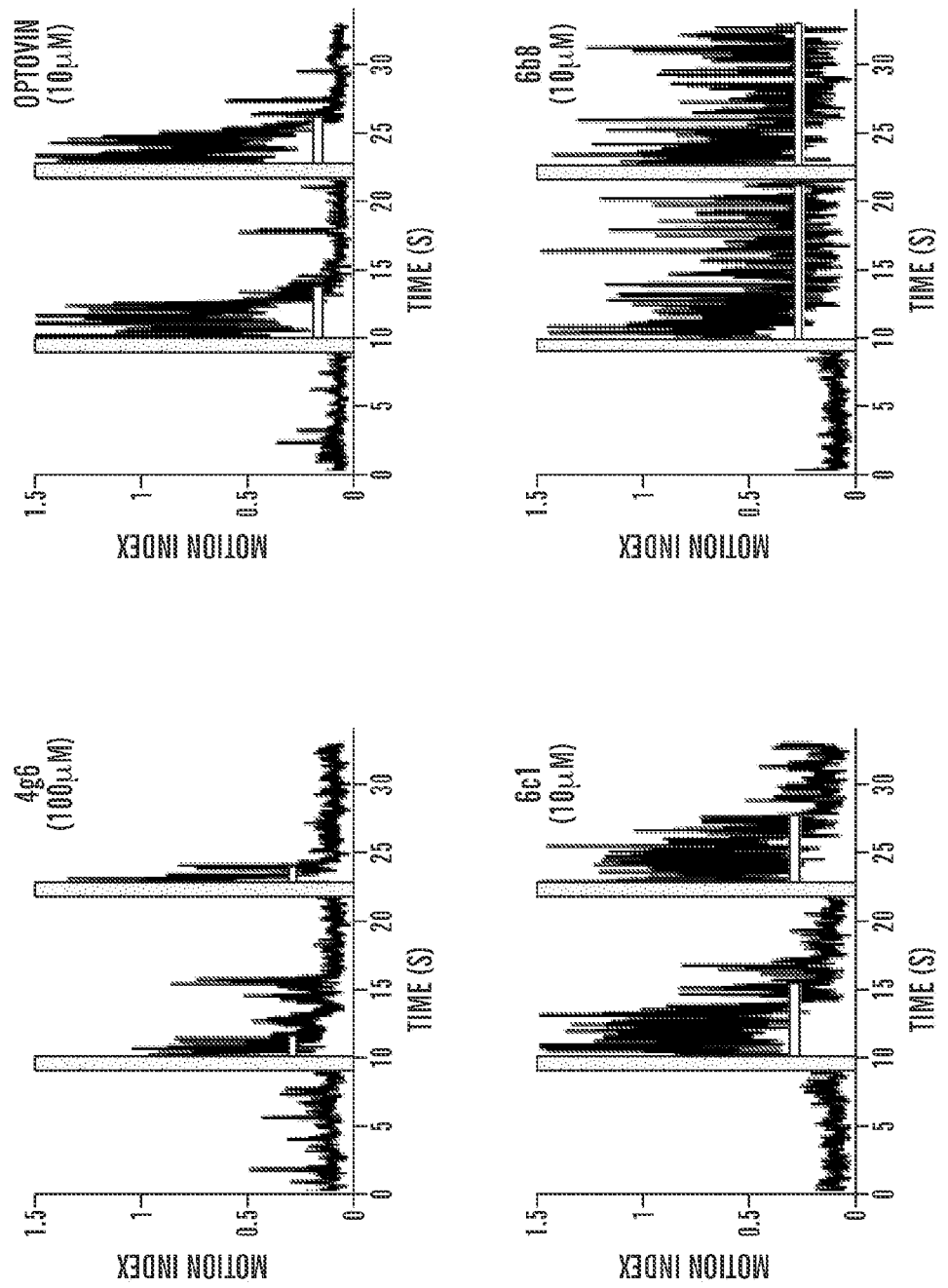
Figure 2C:
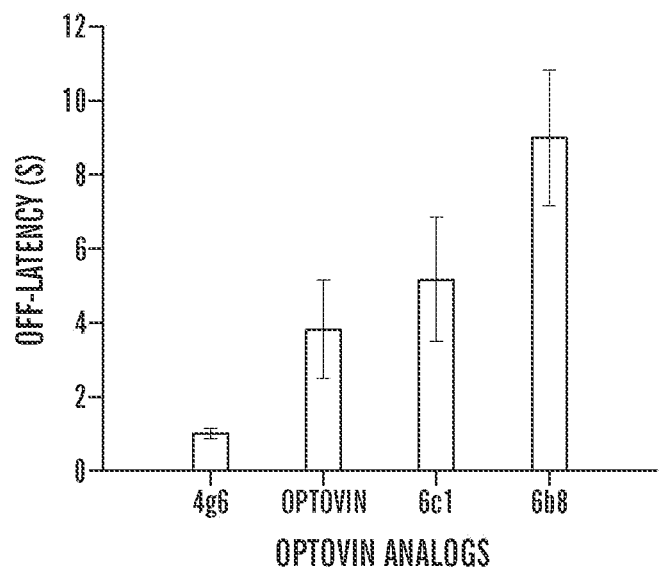

To determine the chemical features responsible for optovin's biological activity, the structure activity relationships of various optovin analogs were analyzed. The optovin chemical structure contains three rings—a pyridine, a pyrrole, and a rhodanine ring (FIG. 2A). To determine if the pyridine ring is necessary for optovin activity, two compounds were tested in which this ring is replaced by either a benzene ring or a methyl group (6b8 (Formula IV) and 6c1 (Formula V) respectively). Both compounds are bioactive, indicating that the pyridine ring is not required for optovin activity (FIG. 2A). To determine the importance of the pyrrole ring, two compounds in which this ring is either removed entirely or replaced with a dimethylaniline ring (compounds 6c5 and 6c7 respectively) were tested. Neither analog retains activity, indicating that the pyrrole ring, or a close structural analog (as in compound 4g6), is necessary for the optovin response (FIG. 2A). Finally, to determine if the rhodanine ring is necessary, the effects of four additional compounds were analyzed. Two out of four rhodanine modifications tested abrogate the optovin response (compounds 6c2 and 6c3). By contrast, nitrogen methylation or replacing the rhodanine ring with hydantoin retains optovin activity (compound 6c4 (Formula VI)) (FIG. 2A). Interestingly, the duration of effect varies considerably among these different analogs, from 1.5 s to 9 s (FIG. 2B-C). Together these observations suggest that optovin's biological activity depends on specific structural features that can be fine-tuned for shorter- or longer lasting effects. Without wishing to be bound by theory, the differing biological activities of the compounds described herein can be due to the compounds being more or less stable in their photo-excited states.

Figure 3A:
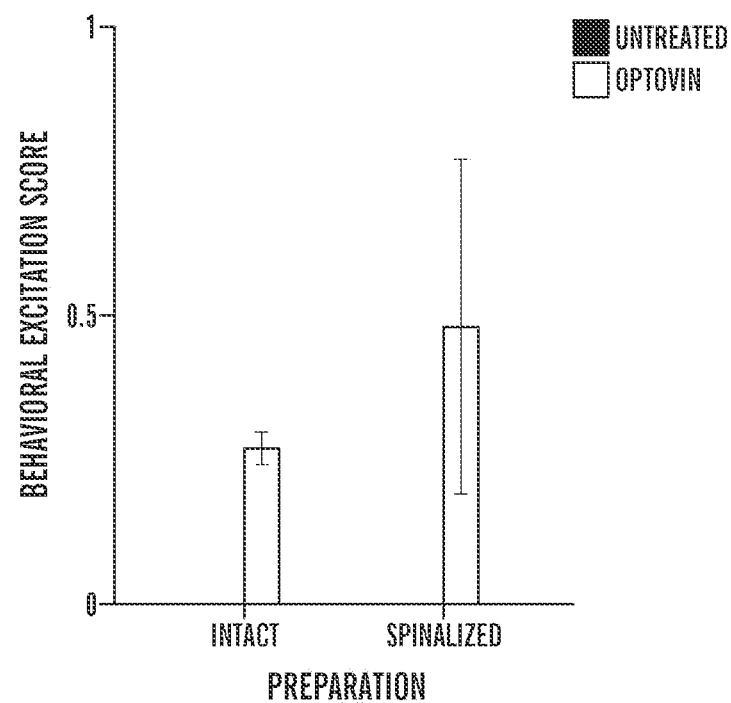
FIGS. 3A-3J demonstrate that TrpA1b is necessary and sufficient for the optovin response.

Optovin-treated zebrafish embryos respond to light at very early stages of development—before the eye and vision develops. This suggests that the optovin response is a non-visual behavior, and that optovin acts on tissues other than the eye. To determine if the eyes are necessary for the optovin response, the responses of intact zebrafish embryos and the trunks of age-matched spinalized preparations transected posterior to the hindbrain were compared. Sensory neurons in the trunk normally respond to various kinds of touch, stretch, temperature and pain, but not to light. Surprisingly, optovin-treated spinalized preparations also respond to light (FIGS. 3A; 10A-10D). Using a 405 nm laser beam, optovin-dependent motor responses of the trunk, tail, and fins were observed—all sites innervated by sensory neurons. These data indicate that visual pathways are not necessary for the optovin-induced light response, and suggest that optovin may act on sensory neurons.

Figure 3B:
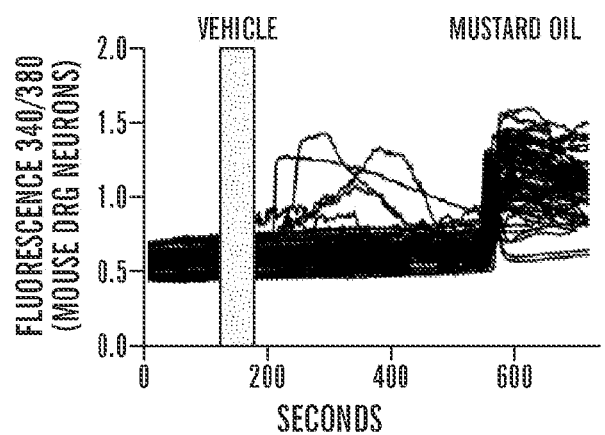
Figure 3C:
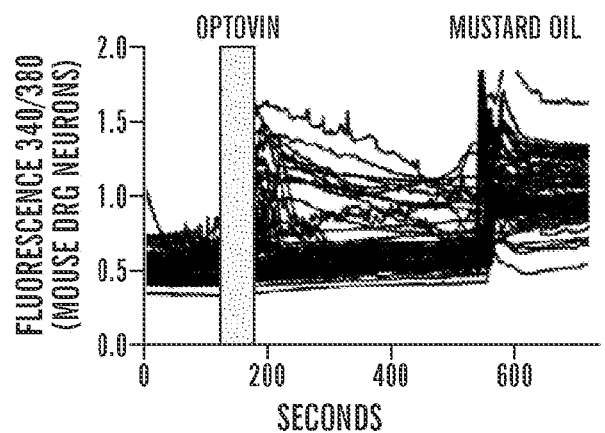
Figure 3D:
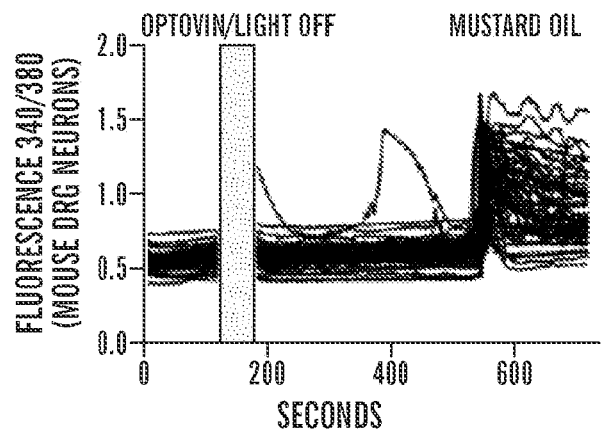
Figure 3E:
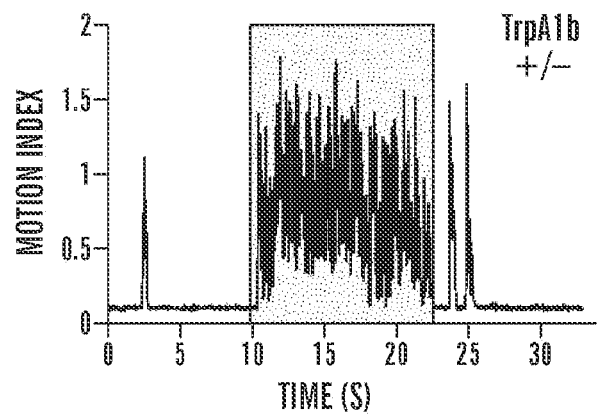

To determine if optovin acts on sensory neurons, the activity of treated and untreated dorsal root ganglia (DRG) sensory neurons isolated from wild type mice were compared. Mouse DRG neurons showed a low amount of random activity when treated with vehicle control and illuminated with light (FIG. 3B). By contrast, DRG neurons were strongly activated by optovin-treatment (FIG. 3C). This activation did not occur when optovin treatment occurred in the dark (FIG. 3E). All optovin responsive DRG sensory neurons also responded to mustard oil (FIGS. 3B-3D), a ligand of TRPA1 ion channels, which are normally expressed in DRG sensory neurons[33]. These data suggest that optovin acts on a molecular target expressed in mammalian DRG sensory neurons; perhaps on TRPA1 itself. TRPA1 channels play important roles in detecting chemical, thermal, and mechanical stimuli in a variety of organisms[34,35].

Figure 3F:
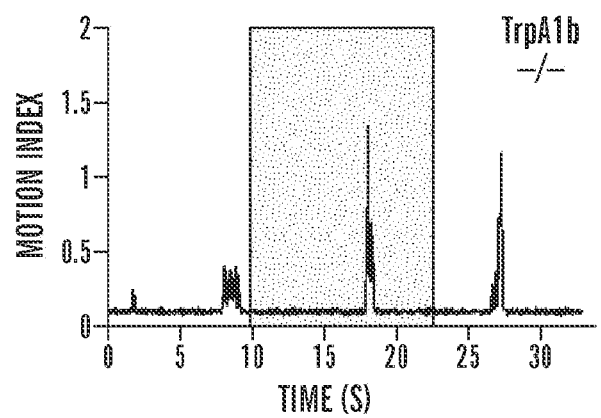
Figure 3G:
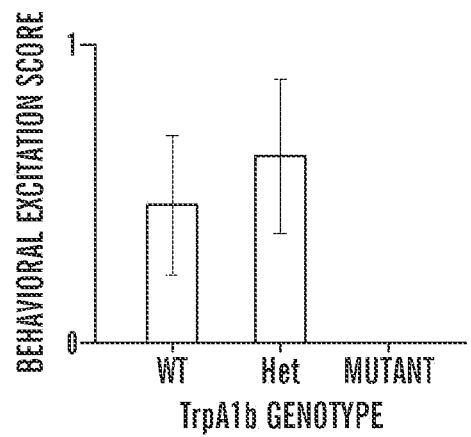
Figure 11:
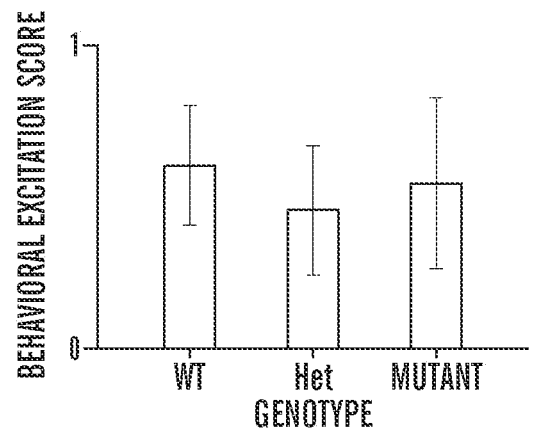
FIG. 11 is a bar chart demonstrating TrpA1a is not necessary for the optovin response. Behavioral excitation scores are shown for the indicated genotypes. Scores were calculated after the second stimulus for individual WT, heterozygous and homozygous mutant animals treated with optovin (n=14, 22 and 20, respectively) Values are means+/− the standard deviation. The differences between group means are not statistically significant, p=0.18. All genotypes respond to the stimulus, indicating that TrpA1a is not necessary for the response.
Figure 12:
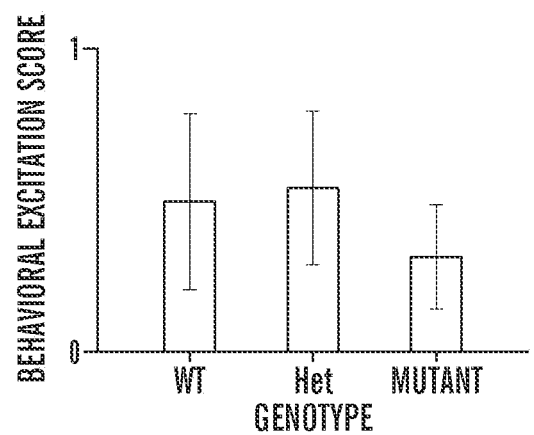
FIG. 12 is a bar chart demonstrating that TrpA1b mutant animals are not generally defective in photo-sensation or motor activity. The behavioral excitation score was calculated during the PMR excitation phase (after the first stimulus) for individual WT, heterozygous and homozygous mutant animals (n=21, 23 and 16 respectively). Mean behavioral excitation scores are shown for the indicated genotypes. Values are means+/−the standard deviation. The differences between group means are not statistically significant, p=0.02. All animals respond to the first pulse of light, indicating that TrpA1b mutant animals are not generally defective for photosensation or motor activity. Optovin affects the normal photomotor response in WT animals, but not in homozygous mutant animals.
Figure 13A:
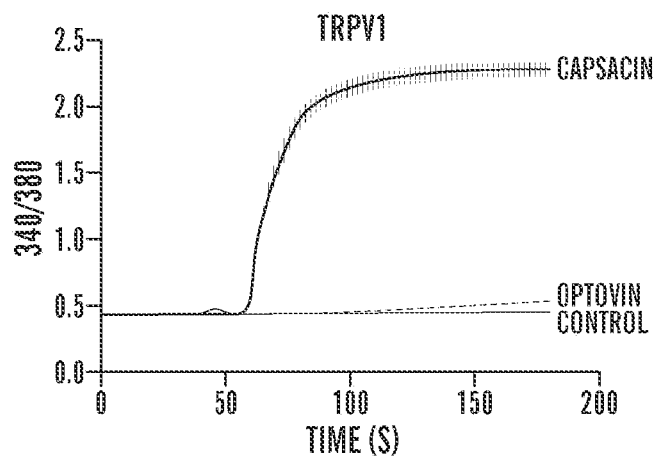
FIGS. 13A-13F are charts demonstrating that optovin specifically activates TRPA1, but not TRPV1 or TRPM8.
Figure 13B:
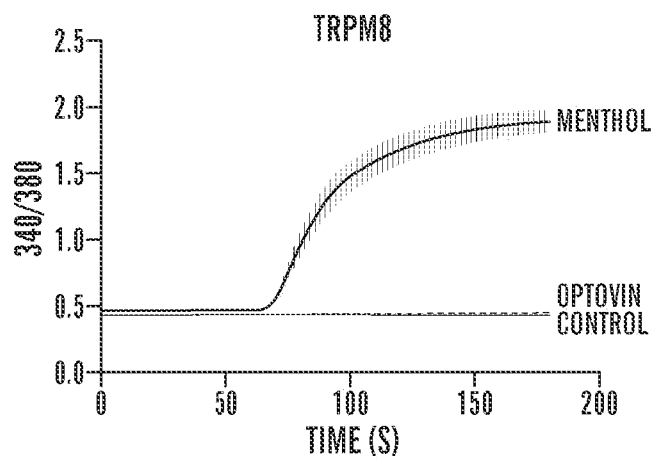
Figure 13C:
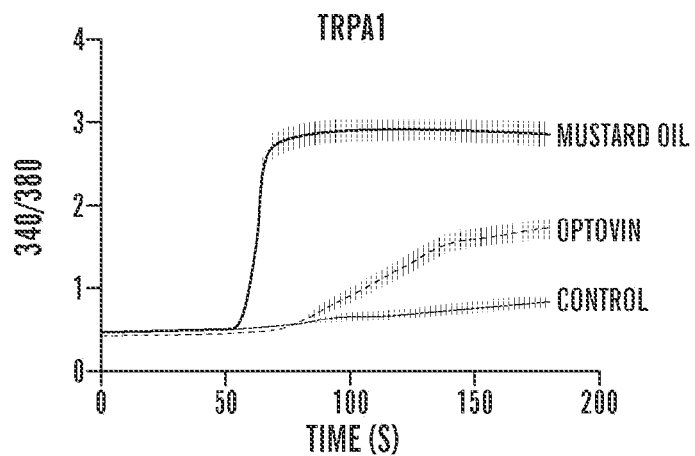
Figure 13D:
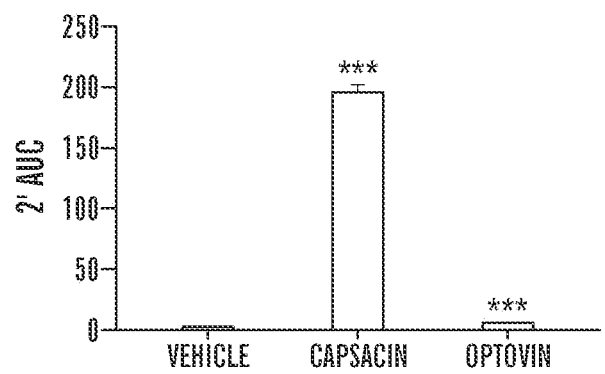
Figure 13E:
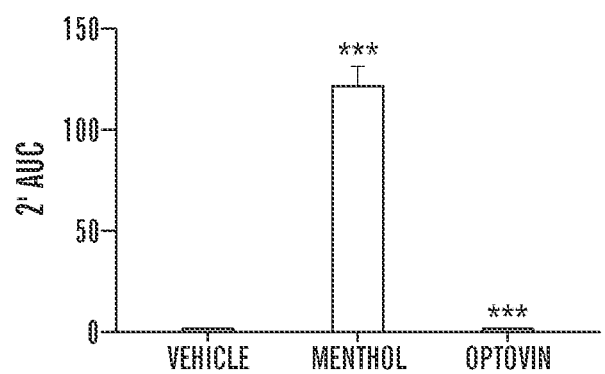
Figure 13F:
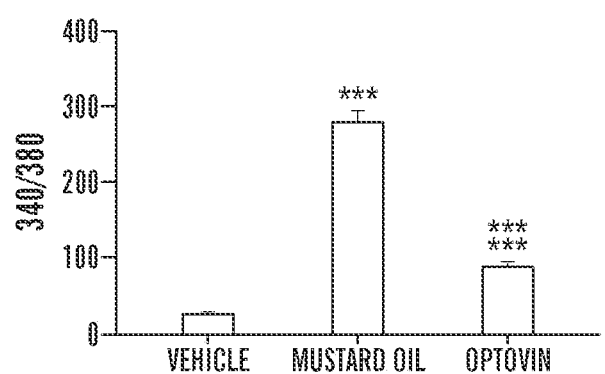
Figure 14B:
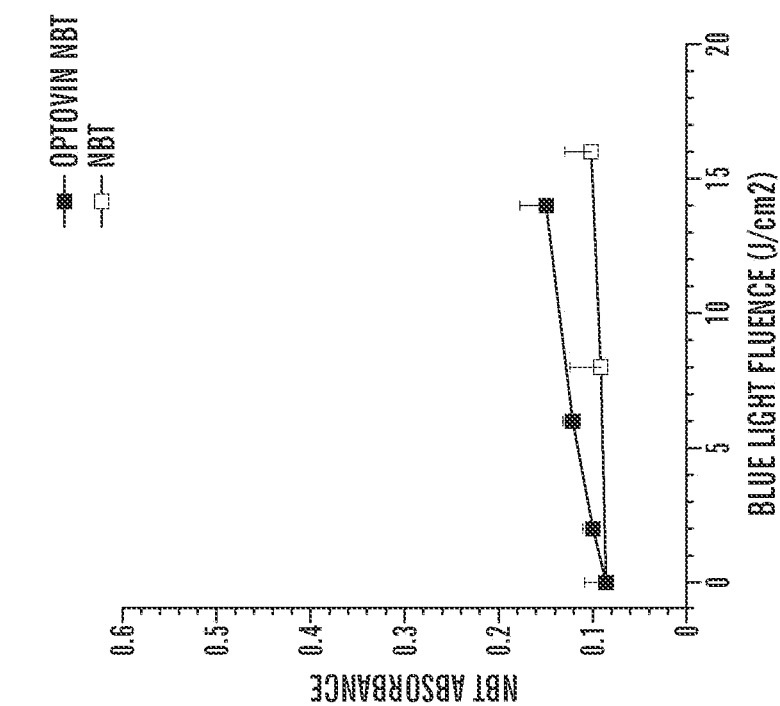
Figure 14A:
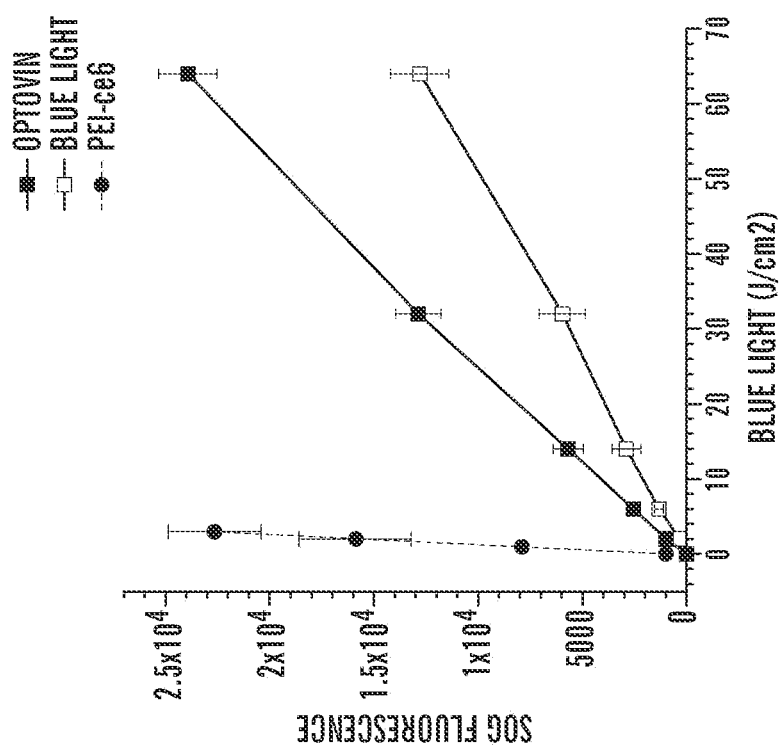

To test the hypothesis that optovin acts on TRPA1, the behavior of TrpA1 mutant animals was analyzed. The zebrafish genome encodes two orthologs of mammalian TrpA1 gene, designated TrpA1a and TrpA1b, with different expression patterns and functions[36]. It was found that optovin-treated wild-type, TrpA1a heterozygous and TrpA1a homozygous mutant animals respond to the 387 nm light stimulus with the typical prolonged motor excitation (FIG. 11). By contrast, TrpA1b homozygous mutant animals failed to respond (FIG. 3E-3G). Importantly, dark-adapted TrpA1b mutant animals still exhibit the PMR behavior and the touch response, indicating that the mutation does not affect movement or light sensation via other pathways (FIG. 12). These data indicate that TrpA1b is necessary for the optovin response in zebrafish.

Figure 3H:
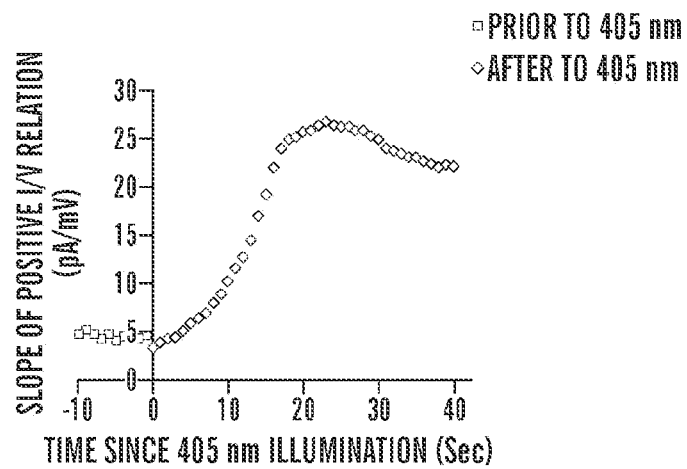
Figure 3I:
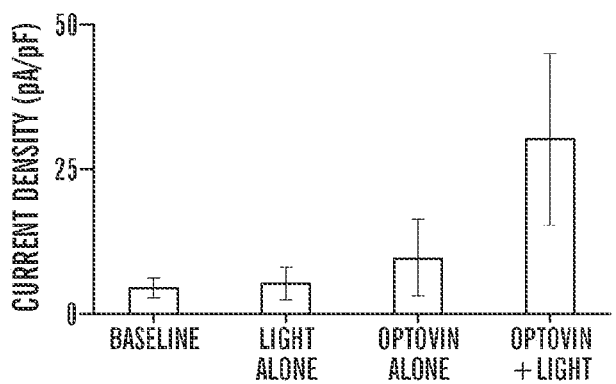
Figure 3J:
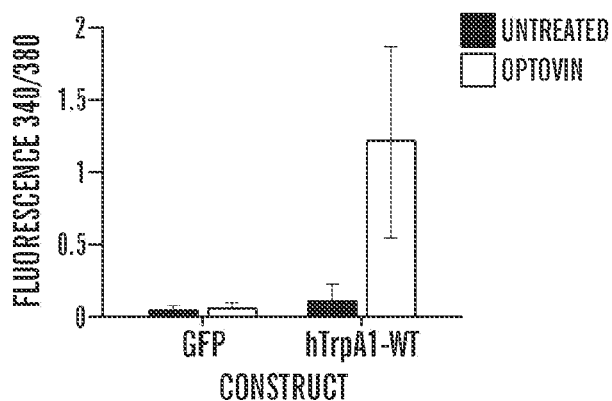
Figure 15:
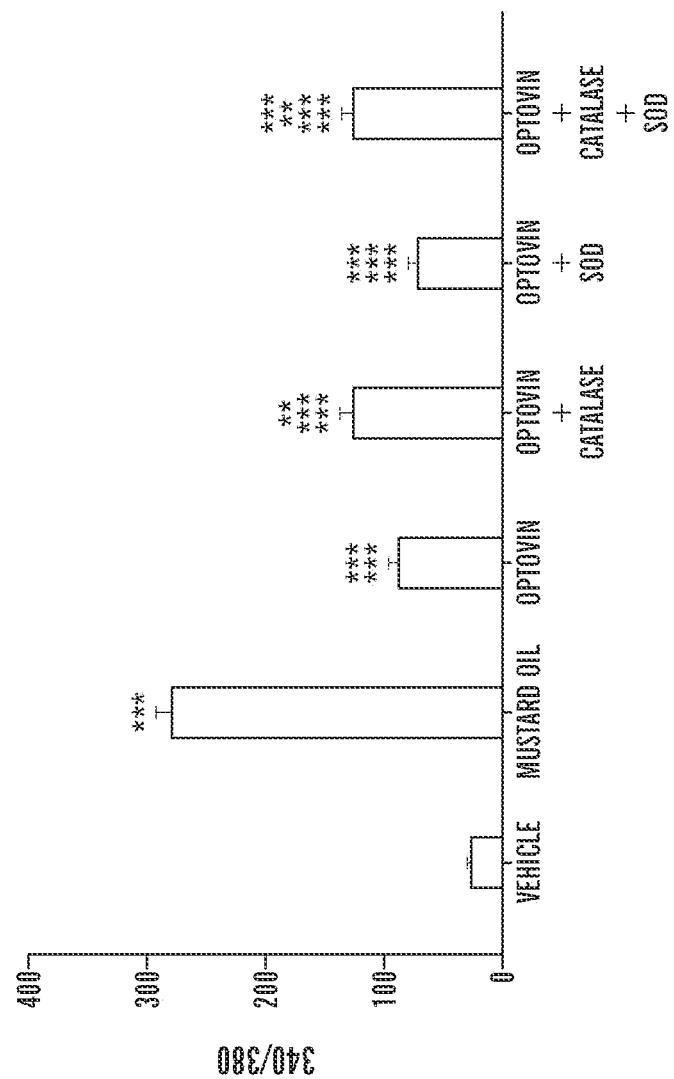
FIG. 15 depicts a bar plot demonstrating that catalase and superoxide dismutase do not significantly reduce optovin activity in HEK cells transfected with hTRPA1. (a) Calcium imaging was performed on HEK cells transfected with hTRPA1 and exposed to the indicated treatments. (p<0.01, *p<0.0001).

To determine if TRPA1 is sufficient for optovin activity, current density amplitudes were analyzed via whole-cell patch clamping in HEK293T cells transfected with the human TrpA1 (hTrpA1) gene. Current density amplitudes in response to positive voltage steps were significantly increased in optovin-treated transfected cells following photo-stimulation, but not in cells lacking optovin, hTrpA1, or light (FIGS. 3H-3I). Similarly, elevated calcium levels were observed in optovin-treated cells transfected with hTrpA1 but not GFP, TRPV1 or TRPM8 (FIGS. 3J and 15). Together, these data suggest that the hTrpA1 gene is sufficient to confer optovin activity on cultured HEK cells.

Figure 4A:
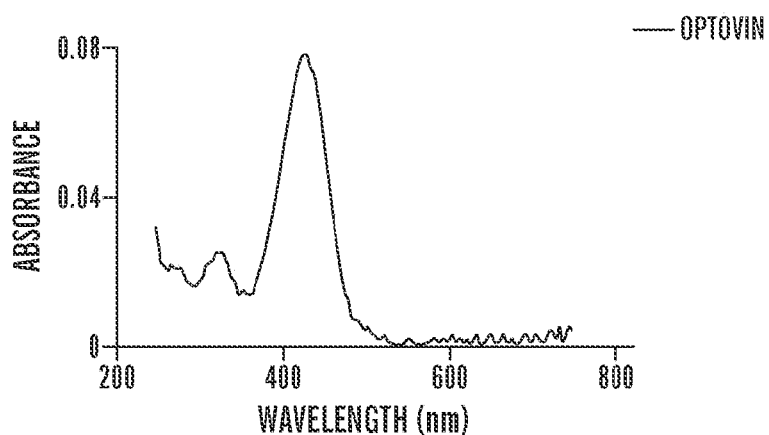
FIGS. 4A-4H demonstrate that optovin activates TRPA1 via structure dependent photochemical reactions.
Figure 4B:
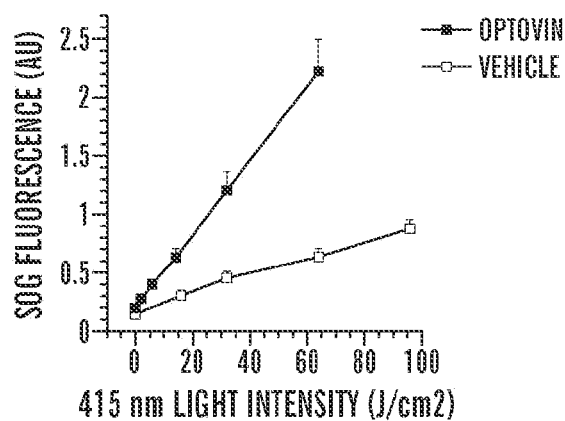

How might optovin activate TRPA1? When molecules absorb light, photons can excite electrons from their ground state to a triplet excited state via intersystem crossing[37]. These photoactivated compounds can then undergo reactions by transferring energy or electrons to target molecules, including aqueous molecular oxygen. Optovin is a yellow-colored compound with peak absorbance at 415 nm (FIG. 4A). To determine if optovin is photochemically reactive, it was exposed to increasing intensities of 415 nm light and assayed for reactive oxygen species (ROS) generation. Under these conditions, optovin generates singlet oxygen (1 $O_2$), but neither hydroxyl radicals nor superoxide (FIGS. 4B and 14A-14D). Without wishing to be bound by theory, these data indicate that light excites optovin to a photochemically reactive state that can activate TRPA1 either directly or via singlet oxygen. Neither catalase nor superoxide dismutase reduce optovin's effects on hTRPA1 transfected HEK cells (FIG. 15), further indicating that hydroxyl radicals and superoxide do not contribute to optovin's activity.

Figure 4C:
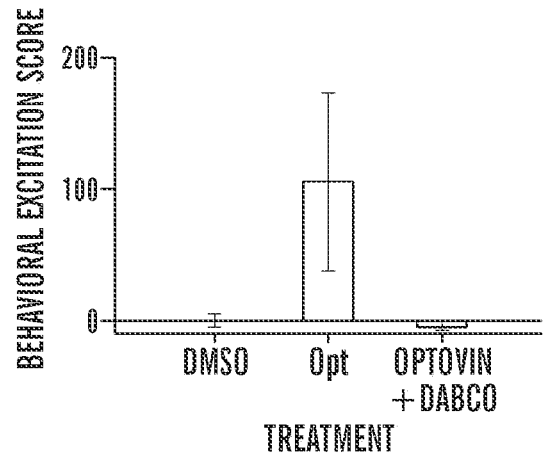

To determine if photochemical reactions are necessary for optovin's behavioral phenotype, the behavior of animals co-treated with DABCO, a singlet oxygen quencher and triplet energy acceptor[38] was analyzed. DABCO was observed to completely suppress the optovin response in vivo, but not affect other light elicited behaviors, like the PMR (FIG. 4C). Two light pulses were presented in each assay. All animals were dark adapted for >10 min prior to the assay. DMSO treated animals respond to only the first pulse of light. This motor response to the first pulse is the PMR excitation phase. In optovin treated animals, animals respond to both pulses of light. The response to the first pulse can be interpreted as a combination of the PMR excitation phases and the response to optovin. The response to the second pulse is due to optovin. In animals treated with optovin and DABCO, the PMR excitation phase can still be seen, but the response to optovin is completely suppressed (data not shown). These data suggest that photochemical energy transfer is necessary for optovin's behavioral effects.

Figure 4D:
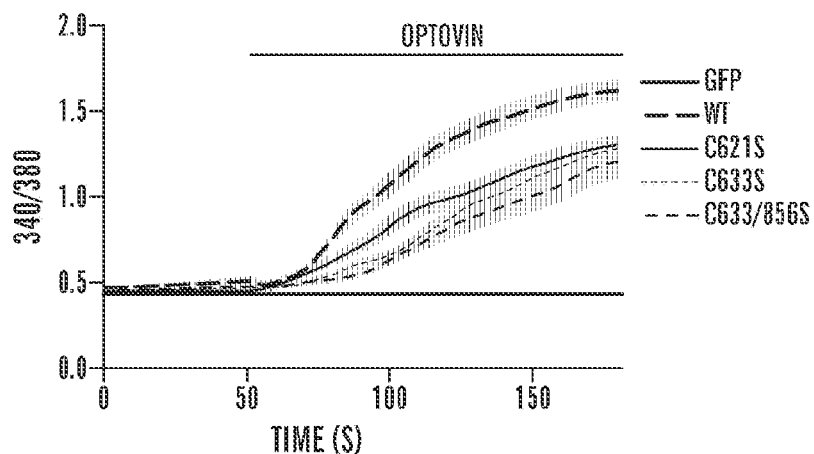
Figure 4E:
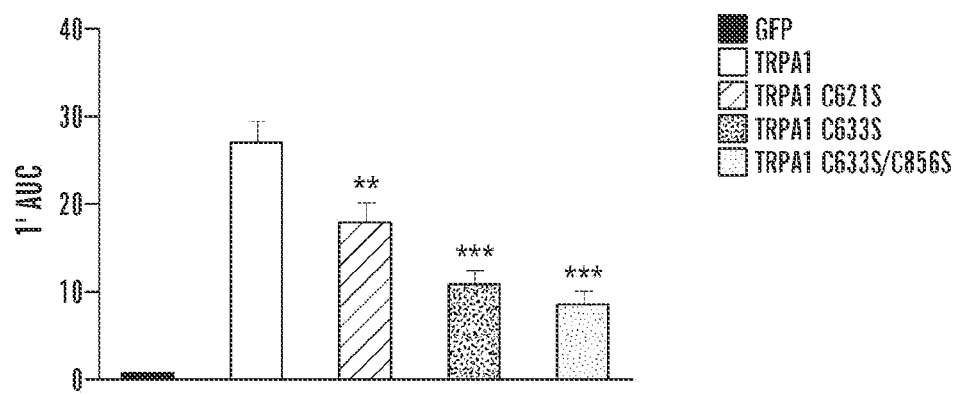
Figure 4F:
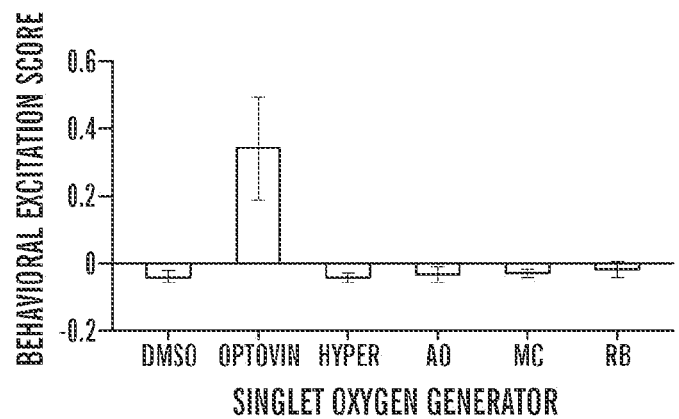

Reactive electrophilic compounds activate TRPA1 channels through the covalent modification of specific cysteine residues including those at amino acid positions 621, 633, and 856. Point mutations in these cysteines can reduce hTRPA1 activation by specific ligands without disrupting overall channel function[39,40]. To determine if these cysteine residues are also important for TRPA1 activation by optovin, intracellular calcium levels were measured in cells transfected with wildtype and mutant hTRPA1 channels. Cells transfected with WT channels show a strong change in fluorescence in response to light and optovin. By contrast, cells transfected with the C621S, C633S or C633S/C856S double mutant channels show a significantly decreased response (FIG. 4D). Together, these data suggest that optovin activates TrpA1 channels via a photoactivated intermediate that reacts with key redox-sensitive cysteine residues in the channel. Rhodanine and hydantoin are photoelectric moieties used in photovoltaic panels and other photochemical applications[41,42]. Nevertheless, photosensitization alone is insufficient to grant optovin its unusual biological activity. For example, optovin is phenotypically unique compared to 171 additional rhodanine-containing compounds contained in the screening library (data not shown). In addition, described herein are experiments indicating that only optovin causes behavioral excitation, while other photosensitizers that also generate singlet oxygen do not (FIG. 4F). These data suggest that generation of singlet oxygen alone is insufficient for optovin's behavioral effects, and that structure-dependent interactions are important for optovin to activate TRPA1 in vivo.

Figure 4G:
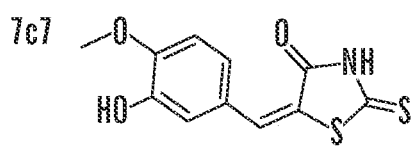
Figure 4G:
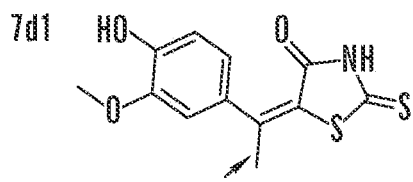
Figure 4H:
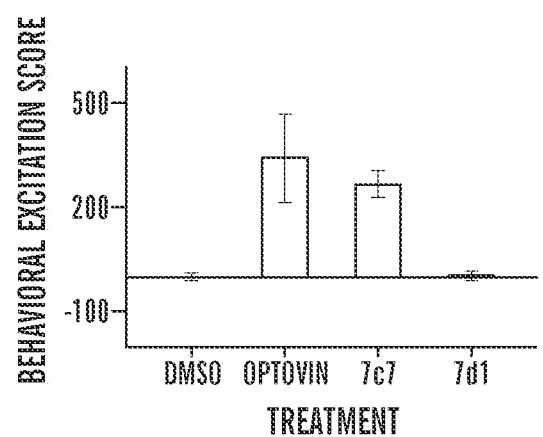
Figure 5A:
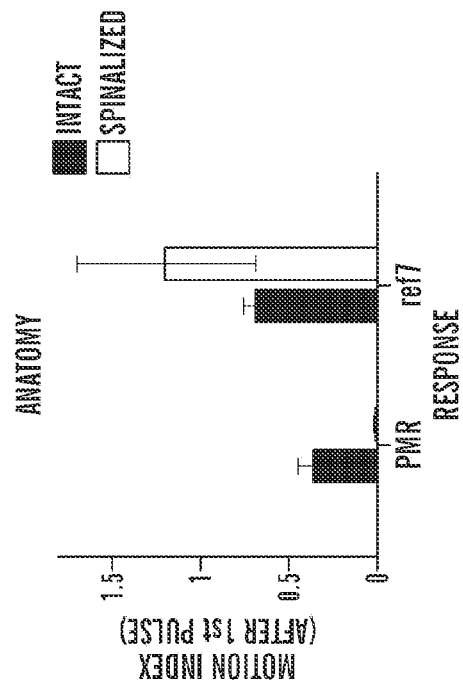
FIGS. 5A-5D demonstrate that the photomotor response (PMR) and optovin responses are mechanistically independent. "Ref7" refers to optovin.
Figure 5B:
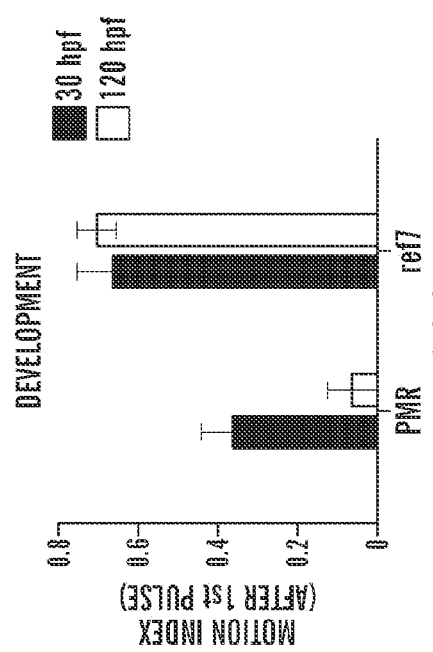
Figure 5C:
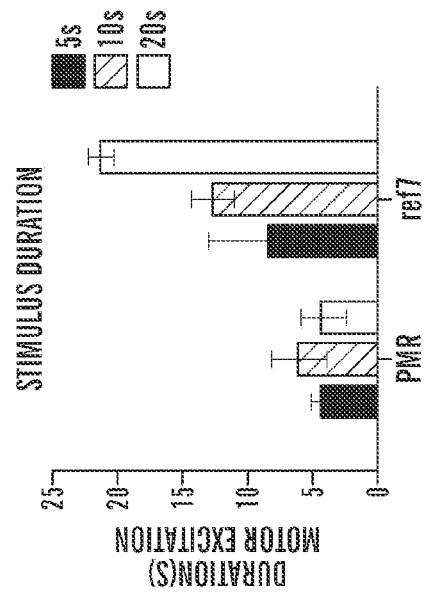
Figure 5D:
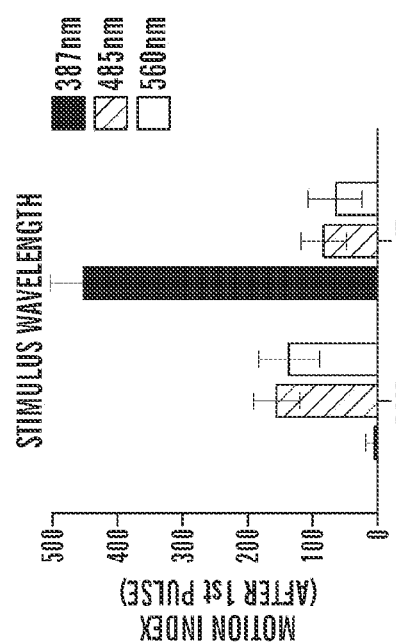
Figure 6:
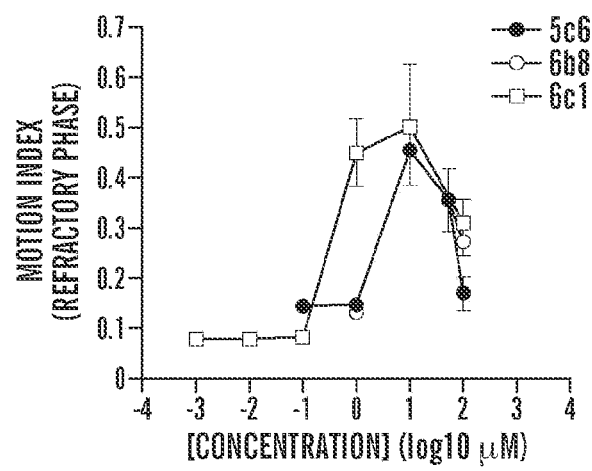
FIG. 6 depicts graphs of the response of zebrafish to optovin analogs at varying concentrations.
Figure 6:
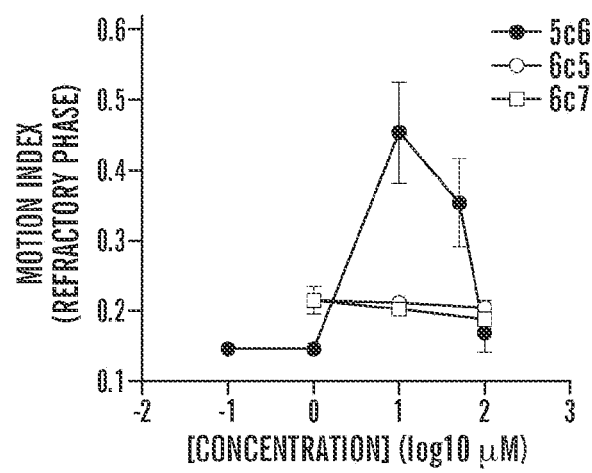
Figure 6:
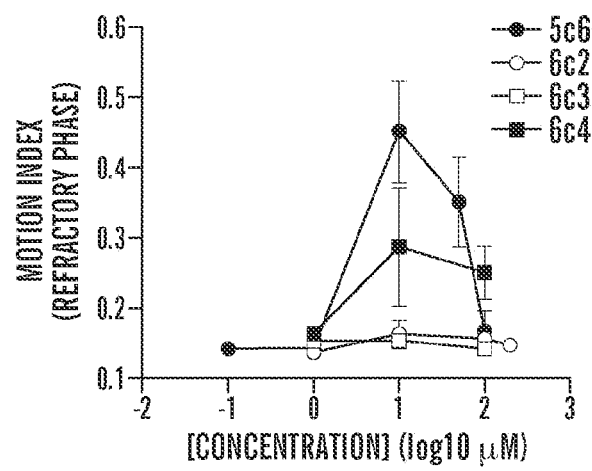
Figure 7A:
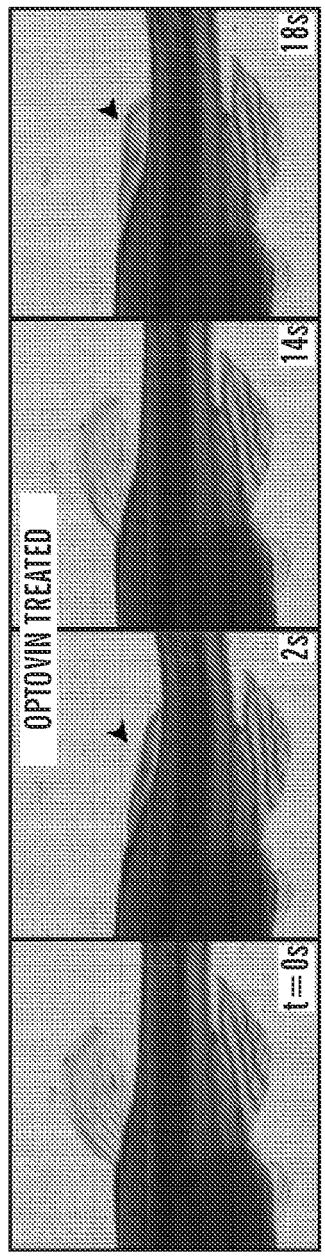
FIGS. 7A-7B depict photographs of experiments demonstrating the remote control of optovin treated animals.
Figure 7B:
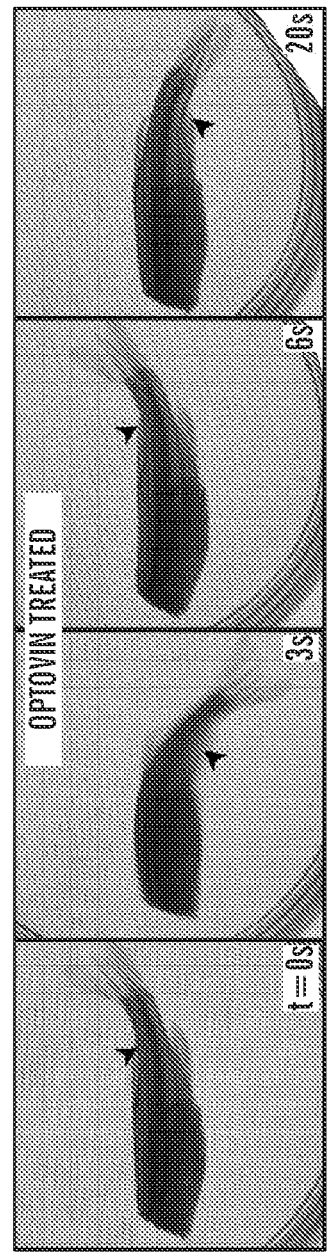
Figure 8:
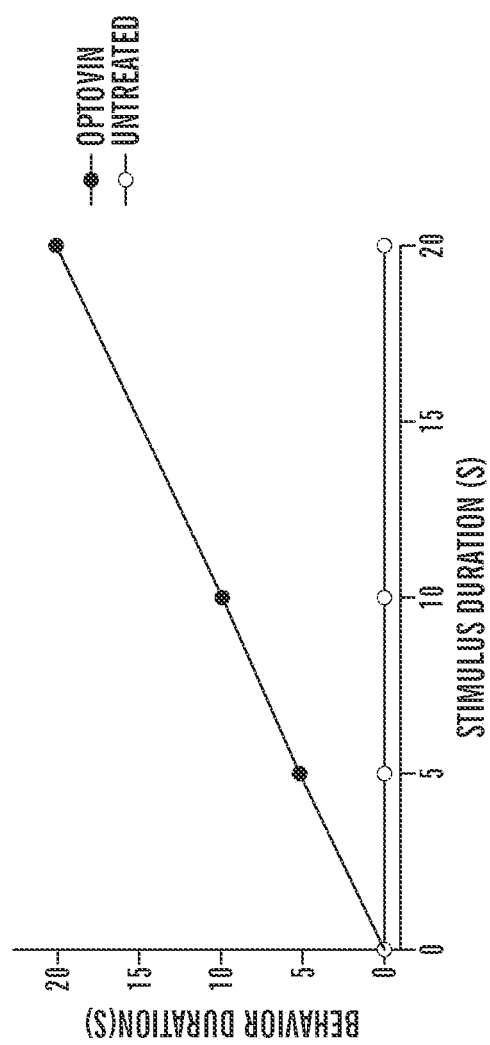
FIG. 8 depicts a line plot demonstrating the duration of motor excitation relative to stimulus duration (n=5). Differences between treated and untreated groups are significant, p<0.001.

Without wishing to be bound by theory, one possible explanation for optovin's activity is that photo-excited optovin directly alkylates cysteine residues in TRPA1 via rapid and reversible covalent bonding. By analogy, previous work has shown that a reversible thioether bond forms between Cys325 of the ERRα receptor and the α,β-unsaturated alkene group of a rhodanine-like small molecule[43]. To determine if a similar reaction may occur between optovin and TRPA1, the activity of a methylated optovin analog in which the methyl group is predicted to hinder thioether bond formation was measured. Optovin and the unmethylated analog 7c7 both cause light-dependent motor excitation in vivo (FIG. 4G-4H). By contrast, the methylated analog 7d1 does not cause light dependent motor activity (FIG. 4G-4H). These data indicate that thioether bond formation may be important for optovin to activate TRPA1, although the possibility that methylation alters other properties of the molecule besides thioether bond formation cannot be excluded.

Optovin's capacity to function in intact adult animals will impact its suitability for future clinical and research applications. Thus, the effects of 405 nm laser illumination on optovin-treated adult zebrafish were analyzed. Illuminating the dorsal fin elicited rapid and reversible contraction of the fin, but did not appear to otherwise disturb the treated animal (data not shown). To determine if fin contraction was voluntary or involuntary, the experiment was repeated using spinalized preparations. Optical control of dorsal fin contraction was preserved in spinalized animals treated with optovin (data not shown). Furthermore, carefully controlled laser illumination of specific regions along the body of spinalized zebrafish produced specific dorsal, ventral, and lateral tail movements reminiscent of those used by intact fish during swimming (data not shown). Because zebrafish TRPA1 is primarily expressed in sensory neurons, these contractions and swimming behaviors likely occur via activation of spinal reflex arcs. These data indicate that optovin enables real-time optical control of neurons in adult wild-type vertebrate animals.

Discussion

These studies have identified optovin, a small molecule that enables optical control of endogenous channels and neuronal signaling in wild-type non-transgenic animals. Optovin differs from previously identified photochemical switch compounds in several significant ways. Optovin acts on TRPA1 channels, which were previously inaccessible via optical techniques. Unlike reversibly caged glutamate and photoswitchable affinity label compounds, optovin is not based on azobenzene photoreactivity. Perhaps most important, optovin functions in intact, living animals.

Optovin was discovered in a behavior-based chemical screen. As with most compounds discovered in phenotype-based screens, determining optovin's mechanism of action has been a central focus of the subsequent studies. Through genetic, molecular, and electrophysiological experiments, identified herein is optovin's cellular target (sensory neurons). Further, it is demonstrated herein that optovin acts on the cation channel TRPA1 in these cells. Several lines of evidence indicate that TRPA1 channels are both necessary and sufficient for optovin function. 1) Genetic mutation of TrpA1b in zebrafish completely eliminates optovin's activity. 2) In a heterogeneous population of mouse DRG neurons, all optovin-responsive neurons also respond to the TRPA1 agonist mustard oil. 3) Nonexcitable cultured cells can be rendered light-sensitive by transfection of the hTrpA1 gene. Therefore, TRPA1 appears to be central to optovin's mechanism of action. Together, these data indicate that optovin specifically targets TRPA1 to permit the light based control of sensory neurons.

Figure 16:
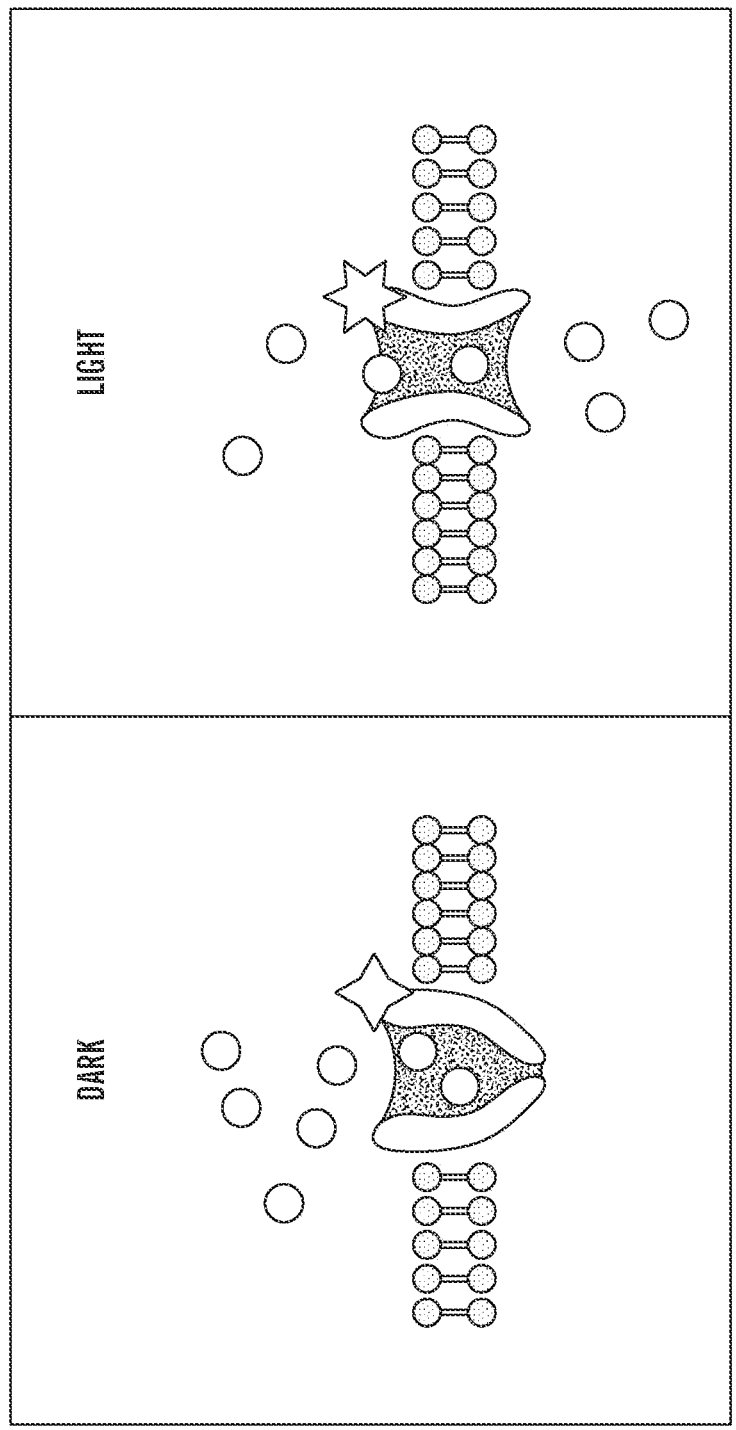
FIG. 16 depicts a schematic model in which optovin is rapidly and reversibly photo-converted into a potent TrpA1 agonist. In the dark, optovin (gray star) does not activate TRPA1 channels (black shape) which remain closed to calcium ions (spheres). In the light, optovin (star) is photo-activated to an excited form that activates TRPA1 causing it to open and allow calcium ions to enter the cell.
Figure 17:
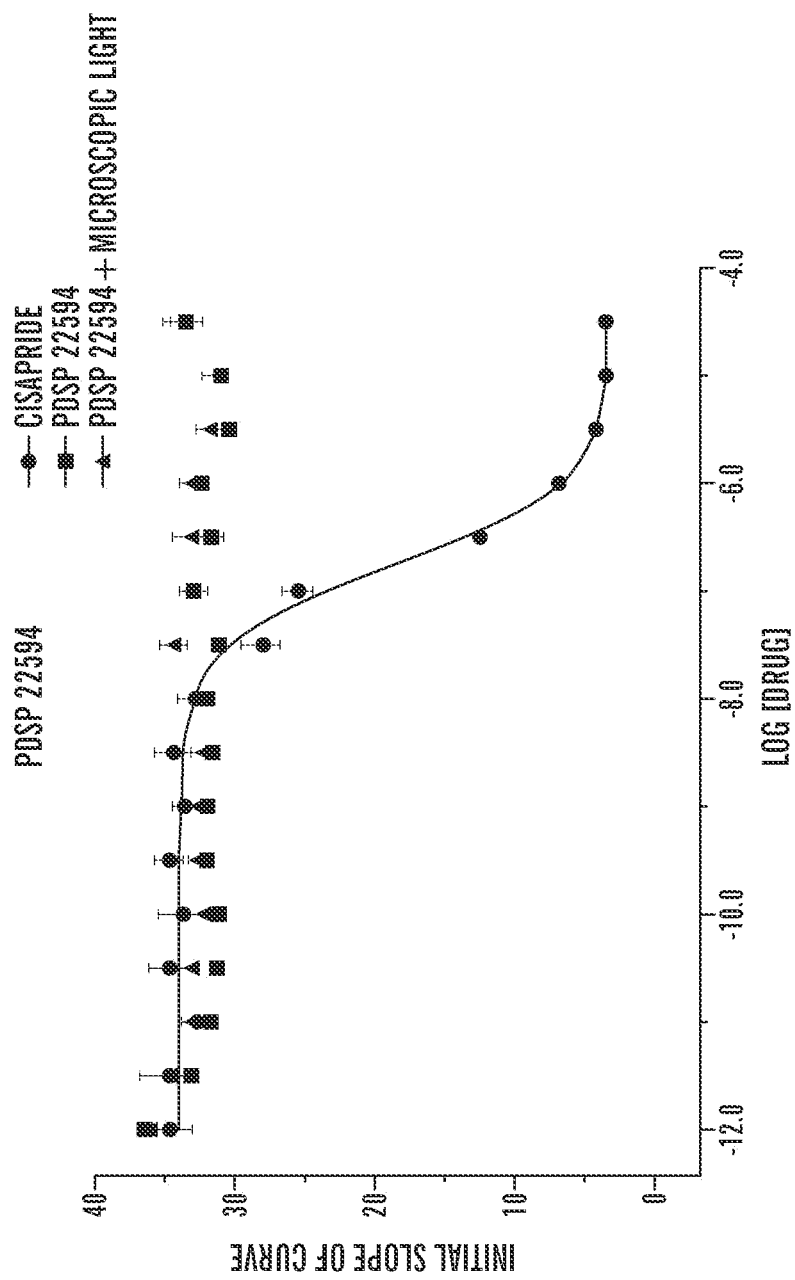
FIG. 17 depicts a graph demonstrating that optovin does not affect the activity of the hERG potassium channel. Optovin (PDSP 22594) was tested for hERG inhibition using the FluxOR system with cisapride as a positive control. Optovin showed no effect on hERG activity with or without prior exposure to light (microscope light source, maximum illumination, 30 seconds).

The data presented herein suggest that optovin activates TRPA1 via structure-dependent photochemical reactions with redox-sensitive cysteine residues. The precise photochemical mechanisms remain unclear, including whether optovin activates TRPA1 directly or through a reactive intermediate, such as singlet oxygen. However, it is clear that singlet oxygen alone is insufficient to cause the phenotype because none of the efficient singlet oxygen-generating compounds tested caused any behavioral excitation in zebrafish. Furthermore, methylation of the α,β-unsaturated rhodanine system, which is predicted to hinder thioether bond formation, significantly reduces bioactivity of an optovin analog in vivo. Without wishing to be bound by theory, these data areas consistent with a model in which optovin can bind to the channel to activate it directly, or can generate singlet oxygen in very close proximity to the target (FIG. 16).

Optovin is at least moderately potent, with a lowest effective dose of 3 uM. Movement in optovin-treated animals begins with a latency of 100-300 msec, depending on developmental stage. The optovin response is selective for stimulation with violet light, and optovin-treated animals do not respond to green or blue light.

It has been demonstrated therein that optovin activates TRPA1 from zebrafish, mouse and humans. The ability to control endogenous TRPA1 channels in vivo opens a number of therapeutic avenues ranging from pain relief to spinal trauma therapy and beyond. Such tools can have applications ranging from basic neuroscience research to clinical interventions.

Methods

Aquaculture.

A large number of fertilized eggs (up to 5,000 embryos per day) were collected from group mating of Ekkwill or TuAB zebrafish. Embryos were raised in HEPES (10 mM) buffered E3 media in a dark incubator at 28° C. until 30 hpf.

Groups of ~8 embryos (28 hpf) were distributed into the wells of flat bottom black-walled 96 well plates filled with E3 media (360 μl). Embryos were then incubated in a dark incubator 25° C. for chemical treatment and subsequent experiments.

Chemical Libraries and Treatments.

The Tim Tec ACTIPROBEβ library contains 10,000 compounds dissolved in DMSO at a stock concentration of 1 mg/ml (~3 mM). The Tim Tec library was screened at a 1:300 dilution in E3 buffer for a final concentration of ~10 μM. Negative controls were treated with an equal volume of DMSO. Stock solutions were added directly to zebrafish in the wells of a 96 well plate, mixed, and allowed to incubate for 2-10 hours in the dark prior to behavioral evaluation in the PMR assay. The Tim Tec library (10,000 compounds) was purchased from the Tim Tec corporation (Newark, Del.). The Neurotransmitter Library (700 compounds; cat #2810) was purchased from Biomol International. Reordered hit compounds were dissolved in DMSO and added to wells as described above.

Behavioral Assay.

Animals were exposed to a two pulse stimulus train with a 10 s inter-stimulus interval. Exposure to the first pulse was used to trigger the photomotor response, which has a refractory phase of approximately 10 minutes. Untreated animals do not respond to the second pulse of light, so motor activity after the second pulse was used to assay for optovin activity. In a typical assay, 1000 frames of digital video were recorded at 33 fps using a Hamamatsu ORCA-ER camera mounted on a Nikon TE200 microscope with a 1× objective. Instrument control and data measurement were performed using custom scripts for Metamorph Software (Molecular Devices). Each video was saved for review. Light stimuli were generated with a 300-watt xenon bulb housed in a Sutter Lambda LS illuminator and delivered to the well 10 s and 20 s after the start of each video. A cold mirror (reflectance between 300 nm and 700 nm) on the Sutter illuminator was used to block wavelengths outside of this range. Light intensity was measured using a PM100D power meter attached to a S120VC photodiode power sensor (Thorlabs). Where indicated, filters were used to restrict the excitation light to the indicated wavelengths.

Spinalized Preparations.

Adult zebrafish (0.5-1.5 years) were briefly anesthetized in ice water and quickly decapitated with a sharp razor blade. Spinalized preparations were incubated in optovin (50 μM) for 1-2 min prior to testing with laser light stimuli (405 nm, 400 μW mm$_{-2}$).

Behavioral Data Analysis.

To analyze digital video recordings, custom software scripts were used to automatically draw six evenly spaced line segments across each well such that each embryo is likely to be crossed by one of the lines. The software then tracks the average intensity of the pixels for each segment over time. As the embryos move, the light intensity at some of the pixels changes. The motion index was calculated by taking the total absolute difference in pixel intensity between frames. This motion index correlates with the overall amount of motion in the well, both in terms of contraction frequency and number of animals in motion. Behavioral features are quantified by 'excitation scores' that are calculated by taking the 75th percentile of the motion index for 3-5 s following the light stimulus. The behavioral profiles were clustered using Euclidean distance and average linkage clustering. All computations and figures were carried out with the Matlab statistical programming environment.

Statistical Analysis.

One-way ANOVA and the Tukey HSD post hoc test were used to test for significant differences between groups, generate 95% confidence intervals and identify groups with significantly different means. For groups with significant differences, the two-tailed t-test was used to test the null hypothesis and calculate the p value. Statistical analyses were performed using the anoval, multcompare and ttest2 functions provided by the MATLAB statistics toolbox.

Electrophysiology.

HEK293 cells were plated upon poly-lysine coated cover slips and transiently transfected with human TRPA1. Voltage clamp recordings were made in the whole-cell configuration 48 hours after transfection using glass electrodes with 2-4M ohm resistance when filled with (in mM) 140 CsCl, 2 Mg$_2$ATP$_3$, 2 MgCl, 5 EGTA, and 10 HEPES (pH adjusted to 7.2 with CsOH) and while bathed at room temperature in extracellular solution containing (in mM) 150 NaCl, 5.4 KCl, 1.8 CaCl$_2$, 1 MgCl, and 5 mM HEPES (pH adjusted to 7.4 with NaOH). A voltage ramp protocol from −80 mV to +80 mV over 400 ms was repeated every 5 seconds during the following conditions: while the cell was dialyzed by the pipette, followed by at least 60 seconds of illumination with 405 nm light, after which optovin (10 μM) containing extracellular solution was perfused into the bath, followed by 1 minute of illumination. Current elicited at holding potentials of +/−70 mV were used to characterize TRPA1 activation.

PDSP Binding Assays.

Activity determinations were generously provided by the National Institute of Mental Health's Psychoactive Drug Screening Program, Contract # HHSN-271-2008-00025-C (NIMH PDSP). Complete assay details are found on-line at: http://pdsp.med.unc.edu/UNC-CH %20Protocol %20Book-.pdf Calcium Imaging Methods.

C57Bl/6 male mice (3-4 weeks old) were decapitated and DRG were dissected into 4° C. Hank's Balanced Salt Solution (HBSS; Gibco), then neurons were dissociated using collagenase (1 mg/mL; Worthington) and dispase (5 mg/mL; Gibco) dissolved in HBSS. Neurons were plated in Neurobasal-A medium (Invitrogen), supplemented with B-27 Supplement (Gibco), L-glutamine (Gibco), and penicillin-streptomycin (Gibco). The neurons were plated onto coverslips coated with 0.1 mg/mL poly-D-lysine (Sigma) and 5 μg/mL laminin (Sigma). After 24 h, neurons were washed with assay buffer (HBSS, supplemented with 9 mM HEPES, 11 mM D-glucose, 0.1% fatty-acid free BSA, pH 7.3) and incubated for 1 h with 2 μM Fura2-AM (Invitrogen) with 0.2% pluronic (Invitrogen) in assay buffer in the dark at room temperature. The neurons were then washed with assay buffer and allowed to equilibrate at room temperature for 30 min prior to imaging. After a 120 s baseline perfusion of assay buffer containing 3.3% DMSO, 100 μM optovin dissolved in the DMSO-assay buffer solution, or the DMSO-assay buffer solution alone as a control, was perfused onto the neurons for a period of 1 min. Fura-2 is activated with UV-light, and the process of imaging Fura-2 was enough to activate the optovin. As a no-light control to ensure that the presence of optovin alone did not cause activation, imaging was stopped for the 1-minute period of optovin treatment, and resumed once the solution perfused back onto the neurons. Following this one-minute period, cells were perfused with DMSO-assay buffer to remove the agonist, which was followed by addition of 100 μM mustard oil (in DMSO-assay buffer) to determine the total number of TrpA1-expressing neurons present. Images were acquired on a Nikon Eclipse Ti microscope (Nikon, Melville, N.Y.). Neurons were counted as activated if they showed a response during the 1-minute activation period.

HEK293 cells were plated onto poly-lysine-coated glass bottom culture dishes (MatTek Corp), and grown in Dulbecco's Modified Eagle's Medium (DMEM, Sigma) supplemented with 10% fetal bovine serum and 100 U/mL penicillin and 100 µg/ml streptomycin. After 24 hrs, cells were transfected, according to manufacturer's instructions, in Opti-MEM media, using 4 µl lipofectamine 2000 (Invitrogen), 0.5 ug EGFP in pcDNA, and 0.3 µg TrpA1 DNA per dish. Media was replaced after 2 hours, and cells were cultured for an additional 17 hours. As previously described for neurons, HEK cells were washed with assay buffer (HBSS Gibco 14025, supplemented with 9 mM HEPES, 11 mM D-glucose, 0.1% fatty-acid free BSA, pH 7.3) and incubated for 1 h with 2 µM Fura2-AM (Invitrogen) with 0.2% pluronic (Invitrogen) in assay buffer in the dark at room temperature. The cells were then washed with assay buffer and allowed to equilibrate at room temperature for 30 min prior to imaging. At the start of the imaging session for each dish, cells were replaced with DMSO-assay buffer. After 50 seconds of imaging, assay buffer was aspirated by hand, and replaced with 100 µM optovin dissolved in the DMSO-assay buffer solution. Each dish of HEK cells was imaged for a total of 3 minutes.

Cells were transfected with the hTRPA1[44], TRPA1 C621S[44], hTRPA1 C633S[45] and hTRPA1 C633S, C856S[45] plasmids as described.

Assay for singlet oxygen generation using singlet oxygen sensor green (SOSG) UV-vis absorption spectra were recorded at 20 uM in methanol using an Evolution 300 UV-Vis Spectrophotometer (Thermo Fisher Scientific Inc., Waltham, Mass.). 96-well black-sided plates were used for fluorescent probe experiments. SOSG (Molecular Probes Invitrogen, Eugene, Oreg.) as a 1 mM stock solution in DMF was added to give final concentration of 5 µM SOSG, to optovin and analogues dissolved as 5 µM solutions in 200 µL 50% H2O/CH3CN preloaded in 96-well plates. An Omnilux Clear-U LED light source (Photo Therapeutics Inc), Carlsbad, Calif.) that emits blue light 415-nm+15-nm as a homogeneous spot with an irradiance of 50 mW/cm$^2$ measured with a power meter (model DMM 199 with 201 standard head; Coherent, Santa Clara, Calif.) that covers an area of one half of a 96-well plate.

Fluorescence spectrophotometry was carried out with SpectraMax M5 plate reader (Molecular Devices, Sunnyvale, Calif.) using excitation and emission at 504 and 525-nm Fluorescence was read after each successive increment of blue light was delivered. As a positive control for a known photosensitizer that absorbs 415-nm light with a quantum yield of singlet oxygen of approximately 0.6 we used a conjugate between polyethylenimine and chlorin(e6) (PEI-ce6)[46].

Long-Term Toxicity Testing.

To determine the long-term effects of optovin exposure on development, behavior and survival, the development, behavior and survival of larvae (n=150) and adult zebrafish (n=2) exposed to 10 µM optovin for 96 hours was analyzed. No differences between the appearance, touch response, heart rate, fin movements, or morphology between the treated and untreated groups were observed.

References

1. Alexander, G. M. et al. Remote control of neuronal activity in transgenic mice expressing evolved G protein-coupled receptors. *Neuron* 63, 27-39, doi:10.1016/j.neuron.2009.06.014 (2009).
2. Armbruster, B. N., Li, X., Pausch, M. H., Herlitze, S. & Roth, B. L. Evolving the lock to fit the key to create a family of G protein-coupled receptors potently activated by an inert ligand. *Proc Natl Acad Sci USA* 104, 5163-5168, doi:10.1073/pnas.0700293104 (2007).
3. Banghart, M., Borges, K., Isacoff, E., Trauner, D. & Kramer, R. H. Light-activated ion channels for remote control of neuronal firing. *Nat Neurosci* 7, 1381-1386, doi:10.1038/nn1356 (2004).
4. Boyden, E. S., Zhang, F., Bamberg, E., Nagel, G. & Deisseroth, K. Millisecond-timescale, genetically targeted optical control of neural activity. *Nat Neurosci* 8, 1263-1268, doi:10.1038/nn1525 (2005).
5. Deisseroth, K. Optogenetics. *Nat Methods* 8, 26-29, doi:10.1038/nmeth.f.324 (2011).
6. Ferguson, S. M. et al. Transient neuronal inhibition reveals opposing roles of indirect and direct pathways in sensitization. *Nat Neurosci* 14, 22-24, doi:10.1038/nn.2703 (2011).
7. Gorostiza, P. et al. Mechanisms of photoswitch conjugation and light activation of an ionotropic glutamate receptor. *Proc Natl Acad Sci USA* 104, 10865-10870, doi:10.1073/pnas.0701274104 (2007).
8. Janovjak, H., Szobota, S., Wyart, C., Trauner, D. & Isacoff, E. Y. A light-gated, potassium-selective glutamate receptor for the optical inhibition of neuronal firing. *Nat Neurosci* 13, 1027-1032, doi:10.1038/nn.2589 (2010).
9. Szobota, S. et al. Remote control of neuronal activity with a light-gated glutamate receptor. *Neuron* 54, 535-545, doi:10.1016/j.neuron.2007.05.010 (2007).
10. Szobota, S. & Isacoff, E. Y. Optical control of neuronal activity. *Annu Rev Biophys* 39, 329-348, doi:10.1146/annurev.biophys.093008.131400 (2010).
11. Volgraf, M. et al. Reversibly caged glutamate: a photochromic agonist of ionotropic glutamate receptors. *J Am Chem Soc* 129, 260-261, doi:10.1021/ja0672690 (2007).
12. Zhang, F., Wang, L. P., Boyden, E. S. & Deisseroth, K. Channelrhodopsin-2 and optical control of excitable cells. *Nat Methods* 3, 785-792, doi:10.1038/nmeth936 (2006).
13. Zhang, F. et al. Multimodal fast optical interrogation of neural circuitry. *Nature* 446, 633-639, doi:10.1038/nature05744 (2007).
14. Wang, S. et al. All optical interface for parallel, remote, and spatiotemporal control of neuronal activity. *Nano Lett* 7, 3859-3863, doi:10.1021/nl072783t (2007).
15. Kramer, R. H., Fortin, D. L. & Trauner, D. New photochemical tools for controlling neuronal activity. *Curr Opin Neurobiol* 19, 544-552, doi:10.1016/j.conb.2009.09.004 (2009).
16. Callaway, E. M. & Katz, L. C. Photostimulation using caged glutamate reveals functional circuitry in living brain slices. *Proc Natl Acad Sci USA* 90, 7661-7665 (1993).
17. Dalva, M. B. & Katz, L. C. Rearrangements of synaptic connections in visual cortex revealed by laser photostimulation. *Science* 265, 255-258 (1994).
18. Fortin, D. L. et al. Photochemical control of endogenous ion channels and cellular excitability. *Nat Methods* 5, 331-338, doi:10.1038/nmeth.1187 (2008).
19. Fortin, D. L. et al. Optogenetic photochemical control of designer K+ channels in mammalian neurons. *J Neurophysiol* 106, 488-496, doi:10.1152/jn.00251.2011 (2011).
20. Noguchi, J. et al. In vivo two-photon uncaging of glutamate revealing the structure-function relationships of dendritic spines in the neocortex of adult mice. *J Physiol* 589, 2447-2457, doi:10.1113/jphysiol.2011.207100 (2011).

21. Volgraf, M. et al. Allosteric control of an ionotropic glutamate receptor with an optical switch. *Nat Chem Biol* 2, 47-52, doi:10.1038/nchembio756 (2006).
22. Wieboldt, R. et al. Photolabile precursors of glutamate: synthesis, photochemical properties, and activation of glutamate receptors on a microsecond time scale. *Proc Natl Acad Sci USA* 91, 8752-8756 (1994).
23. Mourot, A. et al. Rapid optical control of nociception with an ion-channel photoswitch. *Nat Methods* 9, 396-402, doi:10.1038/nmeth.1897 (2012).
24. Brain, S. D. TRPV1 and TRPA1 channels in inflammatory pain: elucidating mechanisms. *Ann N Y Acad Sci* 1245, 36-37, doi:10.1111/j.1749-6632.2011.06326.x (2011).
25. Jordt, S. E. & Ehrlich, B. E. TRP channels in disease. *Subcell Biochem* 45, 253-271 (2007).
26. Kremeyer, B. et al. A gain-of-function mutation in TRPA1 causes familial episodic pain syndrome. *Neuron* 66, 671-680, doi:10.1016/j.neuron.2010.04.030 (2010).
27. Schwartz, E. S. et al. Synergistic role of TRPV1 and TRPA1 in pancreatic pain and inflammation. *Gastroenterology* 140, 1283-1291 e1281-1282, doi:10.1053/j.gastro.2010.12.033 (2011).
28. MacRae, C. A. & Peterson, R. T. Zebrafish-based small molecule discovery. *Chem Biol* 10, 901-908 (2003).
29. Zon, L. I. & Peterson, R. T. In vivo drug discovery in the zebrafish. *Nat Rev Drug Discov* 4, 35-44, doi:10.1038/nrd1606 (2005).
30. Kokel, D. et al. Rapid behavior-based identification of neuroactive small molecules in the zebrafish. *Nat Chem Biol* 6, 231-237, doi:10.1038/nchembio.307 (2010).
31. Schmitt, E. A. & Dowling, J. E. Early retinal development in the zebrafish, Danio rerio: light and electron microscopic analyses. *J Comp Neurol* 404, 515-536 (1999).
32. Rihel, J. et al. Zebrafish behavioral profiling links drugs to biological targets and rest/wake regulation. *Science* 327, 348-351, doi:10.1126/science.1183090 (2010).
33. Dhaka, A., Viswanath, V. & Patapoutian, A. Trp ion channels and temperature sensation. *Annu Rev Neurosci* 29, 135-161, doi:10.1146/annurev.neuro.29.051605.112958 (2006).
34. Bandell, M. et al. Noxious cold ion channel TRPA1 is activated by pungent compounds and bradykinin. *Neuron* 41, 849-857 (2004).
35. Moran, M. M., Xu, H. & Clapham, D. E. TRP ion channels in the nervous system. *Curr Opin Neurobiol* 14, 362-369, doi:10.1016/j.conb.2004.05.003 (2004).
36. Prober, D. A. et al. Zebrafish TRPA1 channels are required for chemosensation but not for thermosensation or mechanosensory hair cell function. *J Neurosci* 28, 10102-10110, doi:10.1523/JNEUROSCI.2740-08.2008 (2008).
37. Laustriat, G. Molecular mechanisms of photosensitization. *Biochimie* 68, 771-778 (1986).
38. Ouannes, C. W., T. Quenching of singlet oxygen by tertiary aliphatic amines Effect of DABCO (1,4-diazabicyclo[2.2.2]octane). *Journal of the American Chemical Society* 90, 6527-6528 (1968).
39. Macpherson, L. J. et al. Noxious compounds activate TRPA1 ion channels through covalent modification of cysteines. *Nature* 445, 541-545, doi:10.1038/nature05544 (2007).
40. Takahashi, N. et al. TRPA1 underlies a sensing mechanism for 02. *Nat Chem Biol* 7, 701-711, doi:10.1038/nchembio.640 (2011).
41. Barton, H., Bojarski, J., Zurowska, A. & Ekiert, L. Photoinduced stereospecific formation of substituted hydantoin from hexobarbital. *Journal of Photochemistry and Photobiology A: Chemistry* 54, 187-196 (1990).
42. Marinado, T. et al. Rhodanine dyes for dye-sensitized solar cells: spectroscopy, energy levels and photovoltaic performance. *Phys Chem Chem Phys* 11, 133-141, doi: 10.1039/b812154k (2009).
43. Patch, R. J. et al. Identification of Diaryl Ether-Based Ligands for Estrogen-Related Receptor alpha as Potential Antidiabetic Agents. *J Med Chem*, doi:10.1021/jm101063h (2011).
44. Macpherson, L. J. et al. Noxious compounds activate TRPA1 ion channels through covalent modification of cysteines. *Nature* 445, 541-545, doi:10.1038/nature05544 (2007).
45. Takahashi, N. et al. TRPA1 underlies a sensing mechanism for O2. *Nature chemical biology* 7, 701-711, doi: 10.1038/nchembio.640 (2011).
46. Tegos, G. P. et al. Protease-stable polycationic photosensitizer conjugates between polyethyleneimine and chlorin(e6) for broad-spectrum antimicrobial photoinactivation. *Antimicrob Agents Chemother* 50, 1402-1410, doi:10.1128/AAC.50.4.1402-1410.2006 (2006).

Example 2

Photo-Sensitive TRPA1 Agonist Treatment

Dosage combinations of a photo-sensitive TrpA1 agonist as described herein and electromagnetic radiation can be used to induce muscle contractions in mice. Mice can be administered a dose of a photo-sensitive TrpA1 agonist systemically, e.g. orally or via injection, or locally, e.g. by topical application. The photo-sensitive TrpA1 agonist can cross the epidermis and enter muscle tissues or be transported to the muscle tissue systemically. The target muscle can then be exposed to electromagnetic radiation of the appropriate wavelength, i.e. a wavelength that will activate that particular photo-sensitive TrpA1 agonist. The electromagnetic radiation can be directed through the epidermis to reach the neurons in the muscle tissue. Alternatively, the radiation can be generated in or near the muscle tissue, e.g. by an implanted, wirelessly controlled LED. Alternatively, the radiation can be generated by an external or implanted radiation source and directed to the target neuron(s) by an implanted fiber optic device.

Depending on the doses of agonist and radiation, the muscle controlled by the target neuron can be induced to contract. The strength and duration can be altered by changing the characteristics of the dosage combination of a photo-sensitive TrpA1 agonist and the electromagnetic radiation.

Example 3

Development of Optovin-Class Compounds

To optimize optovin for photochemical control of TrpA1, medicinal chemistry can be used to create a panel of optimized optovin derivatives that permit flexible manipulation of TrpA1 activity. Optimization can focus on developing compounds that are more potent than optovin and compounds that have desirable physicochemical properties, including altered wavelength sensitivity and rapid photoswitching kinetics. Compounds can also be optimized for low in vivo toxicity and tested for conservation across species.

Additionally, photo-dependent ligands can be developed for additional TRP channels. Compounds can be tested in a panel of cell-based calcium assays to identify compounds that cause photochemical gating of four other TRP channels, TrpC1, TrpV1, TrpC6, and TrpM8. Compounds with activity beyond TrpA1 can be further optimized to generate selective, photoswitchable probes for each of the target TRP channels.

Iterative cycles of medicinal chemistry and biological testing can be used to generate compounds with the desired properties. The methods described herein can deliver a unique chemical toolset for applications ranging from fundamental studies in neuroscience to treatment of diverse nervous system disorders.

Applications of the compounds described herein or identified according to the methods described herein include, but are not limited to: (a) use as a replacement for electric shock in deep brain stimulation for the treatment of depression, epilepsy, and Parkinson's disease[20, 21]; (b) use in pain relief, for example as replacement for TENS (Transcutaneous Electrical Nerve Stimulation); (c) use for light-based control of motor activity, for example controlling extremity movement following spinal cord injury, (for example, as described above herein, zebrafish with severed spines can be induced to swim with optovin treatment and light); (d) use for non-ocular vision (light and perhaps even Braille letters or low-resolution images could be discerned by the blind through photosensitization of neurons in a patch of skin).

Compound design can focus on three distinct regions of the optovin structure: (1) the pyridine, (2) the pyrrole, and (3) the rhodanine. The results described in Example 1 suggest that Region (1) is relatively tolerant of modifications and can in fact be eliminated entirely. The flexibility afforded by this region provides an opportunity to make fairly major modifications in an effort to alter potency, kinetics, and wavelength selectivity, not to mention, attachment of moieties that facilitate or permit, for example, targing to specific tissues or exclusion from others, or that modify biological half-life or retention. The chemical space can be explored fairly broadly when making modifications to this region.

Without wishing to be bound by theory, the results described in Example 1 suggest that Region (2) drives much of the activity of optovin and is fairly intolerant of modification. When designing modifications of Region (2), more subtle changes, such as modifying the two methyl groups in the ring and replacing the pyrrole ring with furan or similar structures can be utilized. Without wishing to be bound by theory, Region (3) appears to be the photo-reactive moiety in optovin. Modifications of Region (3) are likely to have major effects on the wavelength and kinetics of photoreactivity. Both subtle changes in the rhodanine structure and wholesale replacement of the rhodanine with other photoreactive groups, such as hydantoins and cyanines are contemplated.

The method can begin by modifying each region individually, for example by making changes in region (1) while keeping regions (2) and (3) constant. Beneficial modifications from multiple regions can then be combined with the expectation of identifying additive or synergistic effects. In designing modifications of individual regions, attention can also be paid to overall compound structure, with a particular eye to conjugation of double bonds from region to region, as this is likely to influence the absorbance of the molecules and their photo-reactivity.

Potency. The lowest effective dose can be defined as the lowest dose at which the animals give a statistically significant response. For example, compound 6c1 (Formula V) has a lowest effective dose of 300 nM, 10× lower than optovin.

Kinetics. "On rate" can be defined as the latency between the start of the light stimulus and the start of embryo movement. "Off rate" can be defined as the time between the end of the light stimulus and the return of the animals to rest. Shorter "On" and "Off" rates are desirable as they provide tighter temporal control of neuronal activity. Currently, optovin exhibits an "On rate" of ~150 msec and an "Off rate" of 2 sec.

Optovin is selectively activated by violet light and is not activated by other wavelengths. Derivatives that respond to blue, green, red, and infrared light can be selected.

Photo-sensitive TrpA1 agonists can be screened for toxicity and/or unacceptable levels of toxicity. For example, optovin analogs can be deemed to have acceptable toxicity if minimal toxicity is observed at doses 5-10 fold higher than the lowest effective dose. Analog compounds can be examined for toxic effects, e.g. on zebrafish embryos and larvae. Embryos can be treated with each compound at doses ranging from 16 nM to 8 uM and examined carefully by dissecting microscope for developmental phenotypes including morphological changes, necrosis, developmental delay, behavioral defects, and other signs of toxicity that can be observed by light microscopy[24]. In addition, compounds can be tested using the Tg:secA5-YFP line, in which apoptotic cells collect secreted annexin5-YFP and become brightly fluorescent[25]. This line can enable the detection of apoptosis in any tissue type. Particular attention can be applied to detecting neurotoxicity, hepatotoxicity, and renal toxicity.

References

1. Boyden E S, Zhang F, Bamberg E, Nagel G, Deisseroth K. Millisecond-timescale, genetically targeted optical control of neural activity. *Nat Neurosci.* 2005; 8(9)1263-1268.
2. Zemelman B V, Lee G A, Ng M, Miesenbock G. Selective photostimulation of genetically charged neurons. *Neuron.* 2002; 33(1)15-22.
3. Miesenbock G. The optogenetic catechism. *Science.* 2009; 326(5951):395-399.
4. Henderson J M, Federici T, Boulis N. Optogenetic neuromodulation. *Neurosurgery.* 2009; 64(5):796-804.
5. Jordt S E, Bautista D M, Chuang H H, McKemy D D, Zygmunt P M, Hogestatt E D, Meng I D, Julius D. Mustard oils and cannabinoids excite sensory nerve fibres through the TRP channel ANKTM1. *Nature.* 2004; 427 (6971):260-265.
6. Corey D P, Garcia-Anoveros J, Holt J R, Kwan K Y, Lin S Y, Vollrath M A, Amalfitano A, Cheung E L, Derfier B H, Duggan A, Geleoc G S, Gray P A, Hoffman M P, Rehm H L, Tamasauskas D, Zhang D S. TRPA1 is a candidate for the mechanosensitive transduction channel of vertebrate hair cells. *Nature.* 2004; 432(7014723-730.
7. Negate K, Duggan A, Kumar G, Garcia-Anoveros J. Nociceptor and hair cell transducer properties of TRPA1, a channel for pain and hearing. *J Neurosci.* 2005; 25(16): 4052-4061.
8. Story G M, Peler A M, Reeve A J, Eld S R, Mosbacher J, Hricik T R, Earley T J, Hergarden A C, Andersson D A, Hwang S W, McIntyre P, Jegla T, Bevan S, Patapoutian A.

ANKTM1, a TRP-like channel expressed in nociceptive neurons, is activated by cold temperatures. *Cell.* 2003; 112(6):819-829.
9. Bautista D M, Jordt S E, Nikai T, Tsuruda P R, Read A J, Poblete J, Yamoah E N, Basbaum Al, Julius D. TRPA1 mediates the inflammatory actions of environmental irritants and proalgesic agents. *Cell.* 2006; 124(41269-1282.
10. Kwan K Y, Allchorne A J, Vollrath M A, Christensen A P, Zhang D S, Woolf C J, Corey D P. TRPA1 contributes to cold, mechanical, and chemical nociception but is not essential for hair-cell transduction. *Neuron.* 2006; 50(2): 277-289.
11. Obata K, Katsura H, Mizushima T, Yamanaka H, Kobayashi K, Dai Y, Fukuoka T, Tokunaga A, Tominaga M, Noguchi K. TRPA1 induced in sensory neurons contributes to cold hyperalgesia after inflammation and nerve injury. *J Clin Invest.* 2005; 115(9):2393-2401.
12. Winn M P, Conlon P J, Lynn K L, Farrington M K, Creazzo T, Hawkins A F, Daskalakis N, Kwan S Y, Ebersviller 8, Burchette J L, Pericak-Vance M A, Howell D N, Vance J M, Rosenberg P B. A mutation in the TRPC6 cation channel causes familial focal segmental glomerulosclerosis. *Science.* 2005; 308(57241801-1804.
13. Reiser J, Polu K R, Moller C C, Kenlan P, Altintas M M, Wei C, Faul C, Herbert S, Villegas I, Avila-Casado C, McGee M, Sugimoto H, Brown D, Kaliuri R, Mundel P, Smith P L, Clapham D E, Pollak M R. TRPC6 is a glomerular slit diaphragm-associated channel required for normal renal function. *Nat Genet.* 2005; 37(7):739-744.
14. Corteling R L, Li S, Giddings J, Westwick J, Poll C, Hall I P. Expression of transient receptor potential C6 and related transient receptor potential family members in human airway smooth muscle and lung tissue. *Am J Respir Cell Mot Biol.* 2004; 30(2):145-154.
15. Li S, Westwick J, Cox B, Poll C T. TRP channels as drug targets. *Novartis Found Symp.* 2004; 258:204-213; discussion 213-221, 263-206.
16. Li S, Westwick J, Poll C. Transient receptor potential (TRP) channels as potential drug targets in respiratory disease. *Cell Calcium.* 2003; 33(5-6):551-558.
17. Caterina M J, Schumacher M A, Tominaga M, Rosen T A, Levine J D, Julius D. The capsaicin receptor: a heat-activated ion channel in the pain pathway. *Nature.* 1997; 389(6653):816-824.
18. Bidaux G, Flourakis M, Thebault S, Zholos A, Beck B, Gkika D, Roudbaraki M, Bonnet J L, Mauroy B, Shuba Y, Skryma R, Prevarskaya N. Prostate cell differentiation status determines transient receptor potential melastatin member 8 channel subcellular localization and function. *J Clin Invest.* 2007; 117(6)1647-1657.
19. Tsavaler L, Shapero M H, Morkowski S, Laus R. Trp-p8, a novel prostate-specific gene, is up-regulated in prostate cancer and other malignancies and shares high homology with transient receptor potential calcium channel proteins. *Cancer Res.* 2001; 61(9):3760-3769.
20. Weaver F M, Follett K, Stern M, Hur K, Harris C, Marks W J, Jr., Rothlind J, Sagher O, Reda O, Moy C S, Pahwa R, Burchiel K, Hogarth I D, Lai E C, Duda J E, Holloway K, Samii A, Horn S, Bronstein J, Stoner G, Heemskerk J, Huang G D. Bilateral deep brain stimulation vs best medical therapy for patients with advanced Parkinson disease: a randomized controlled trial. *JAMA.* 2009; 301 (0:63-73.
21. Krack P, Hariz M I, Baunez C, Guridi J, Obeso J A. Deep brain stimulation: from neurology to psychiatry? *Trends Neurosci.* 2010; 33(10):474-484.
22. Kokel D, Bryan J, Laggner C, White R, Cheung C Y, Mateus R, Healey D, Kim S, Werdich A A, Haggarty S J, Macrae C A, Shoichet B, Peterson R T. Rapid behavior-based identification of neuroactive small molecules in the zebrafish. *Nat Chem Biol.* 2010; 6(3):231-237.
23. Clapham D E. TRP channels as cellular sensors. *Nature.* 2003; 428(6966):517-524.
24. Rubinstein A L. Zebrafish assays for drug toxicity screening. *Expert Qpin Drug Metab Toxicol.* 2006; 2(2): 231-240.
25. van Ham T J, Mapes J, Kokel D, Peterson R T. Live imaging of apoptotic cells in zebrafish. *FASEB J.* 2010; 24(11):4336-4342.
26. Milan D J, Giokas A C, Seduce F C, Peterson R T, MacRae C A. Notchl b and neuregulin are required for specification of central cardiac conduction tissue. *Development.* 2006; 133(6):1125-1132.
27. Zhang Y, Kowal D, Kramer A, Dunlop J. Evaluation of FLIPR Calcium 3 Assay Kit—a new no-wash fluorescence calcium indicator reagent. *J Biomol Screen.* 2003; 8(5):571-577.
28. Xin H, Wang Y, Todd M J, Qi J, Minor L K. Evaluation of no-wash calcium assay kits: enabling tools for calcium mobilization. *J Biomol Screen.* 2007; 12(5):705-714.
29. Thomas D, Tovey S C, Collins T J, Bootman M D, Berridge M J, Lipp P. A comparison of fluorescent Ca2+ indicator properties and their use in measuring elementary and global Ca2+ signals. *Ceii Calcium.* 2000; 28(4):213-223.
30. Arenkiel B R, Klein M E, Davison I G, Katz L C, Ehlers M D. Genetic control of neuronal activity in mice conditionally expressing TRPV1. *Nat Methods.* 2008; 5(4): 299-302.

TABLE 1

Receptor profiling in vitro identifies no targets that are strongly inhibited by optovin derivatives. For primary screening, data represent mean % inhibition (N = 4 determinations) for compound tested at receptor subtypes. If >50% inhibition was obtained at 10 uM, Ki determinations were performed. For Ki determinations, data represent Ki (nM) values obtained from non-linear regression.

| CMPD | PRIMARY SCREENING RESULTS | | Ki DETERMINATIONS | |
| --- | --- | --- | --- | --- |
| | 16835 | 16836 | 16835 | 16836 |
| Molecular Target | 16835 % Inhibition | 16836 % Inhibition | Ki +/- SEM (nM) | Ki +/- SEM (nM) |
| 5-HT1A | 29.7 | 33.5 | | |
| 5-HT1B | 1.7 | 31.9 | | |
| 5-HT1D | 16 | 14.5 | | |
| 5-ht1e | −26.9 | 11.9 | | |
| 5-HT2A | 20 | 37.2 | | |
| 5-HT2B | 7.6 | 41 | | |
| 5-HT2C | 10.8 | 26.7 | | |
| 5-HT3 | 11.1 | 31.7 | | |
| 5-ht5a | −28.4 | 10.8 | | |
| 5-HT6 | 15.7 | 21.1 | | |
| 5-HT7 | −10 | 13.6 | | |
| Alpha1A | 8.8 | 3.2 | | |
| Alpha1B | 8.8 | 29.5 | | |
| Alpha1D | 6.1 | 7.3 | | |
| Alpha2A | 43.9 | 23.7 | | |
| Alpha2B | −1.3 | −2 | | |
| Alpha2C | −3 | −7.6 | | |
| Beta1 | 10.3 | 21.1 | | |
| Beta2 | −8.1 | 1.7 | | |
| Beta3 | 25.3 | 25.4 | | |
| P Rat Brain | 41.7 | 69.6 | | 5329 +/− 291 |
| D1 | 3.4 | 38 | | |
| D2 | −6.7 | −17.8 | | |

TABLE 1-continued

Receptor profiling in vitro identifies no targets that are strongly inhibited by optovin derivatives. For primary screening, data represent mean % inhibition (N = 4 determinations) for compound tested at receptor subtypes. If >50% inhibition was obtained at 10 uM, Ki determinations were performed. For Ki determinations, data represent Ki (nM) values obtained from non-linear regression.

| CMPD | PRIMARY SCREENING RESULTS | | Ki DETERMINATIONS | |
|---|---|---|---|---|
| | 16835 | 16836 | 16835 | 16836 |
| Molecular Target | % Inhibition | % Inhibition | Ki +/− SEM (nM) | Ki +/− SEM (nM) |
| D3 | 10 | 0.8 | | |
| D4 | 20.1 | 4.4 | | |
| D5 | 42.8 | 62.7 | | 8.434 +/− 994 |
| DAT | 18.5 | 17 | | |
| DOR | 19.2 | 48.8 | | |
| GABAA | 9.8 | 68 | | 1112 +/− 320 |
| H1 | −8.5 | 18.7 | | |
| H2 | 22.3 | 49.7 | | |
| H3 | 13.9 | 16.5 | | |
| H4 | 12.8 | 1.3 | | |
| KOR | 41.8 | 66.7 | | 8278 +/− 861 |
| M1 | −17.6 | 22.2 | | |
| M2 | 10.1 | 37.1 | | |
| M3 | −2.3 | 29.8 | | |
| M4 | 25.1 | 18 | | |
| M5 | 0.1 | 25.3 | | |
| MOR | 14.4 | 43.5 | | |
| NET | 14 | 44.7 | | |
| SERT | 12.5 | 40.1 | | |
| Sigma 1 | 42.2 | 51.6 | | 5182 +/− 335 |

TABLE 2

Receptor profiling in vitro identifies no targets that are strongly inhibited by optovin. For primary screening, data represent mean % inhibition (N = 4 determinations) for compound tested at receptor subtypes.

| Receptor | Avg % inhibition | sem |
|---|---|---|
| DOR | −7.2 | 0.7 |
| KOR | 10.9 | 2.6 |
| MOR | −0.7 | 1.4 |
| Sigma 1 | −13.7 | 6.8 |
| Sigma 2 | 16.0 | 14.8 |
| Alpha1D | 30.4 | 4.4 |
| 5-HT2B | −2.0 | 3.0 |
| 5-HT2C | 7.0 | 9.1 |
| 5-HT6 | −16.5 | 5.3 |
| 5-HT7 | −0.8 | 2.5 |
| PBR | −11.3 | 1.2 |
| Alpha2A | 40.5 | 3.0 |
| Alpha2B | 8.9 | 10.7 |
| Alpha1A | −5.4 | 2.4 |
| Alpha1B | 7.2 | 2.8 |
| Alpha2C | 3.3 | 4.5 |
| GABAA | −2.2 | 6.5 |
| A2B2 | −19.2 | 3.6 |
| A2B4 | −7.8 | 6.4 |
| A3B2 | −5.6 | 0.7 |
| A3B4 | −12.5 | 3.0 |
| A4B2 | −26.8 | 1.6 |
| A4B2** | −29.1 | 3.4 |
| A4B4 | −8.8 | 2.6 |
| Beta1 | 19.4 | 5.0 |
| Beta2 | −3.8 | 6.0 |
| Beta3 | 20.2 | 3.9 |
| 5-HT1D | 12.9 | 17.5 |
| 5-HT2A | −1.1 | 6.3 |
| 5-ht1e | −21.5 | 7.0 |
| D1 | 9.0 | 10.4 |
| D2 | −6.8 | 10.3 |
| D3 | 34.3 | 11.5 |
| D4 | 0.2 | 3.9 |
| D5 | 13.6 | 2.7 |
| M1 | 32.9 | 4.2 |
| M1 | 16.9 | 7.5 |
| M2 | 6.6 | 13.6 |
| M3 | 9.1 | 3.5 |
| M4 | 3.5 | 4.8 |
| M5 | 3.7 | 5.2 |
| NET | −1.3 | 7.5 |
| 5-HT1A | 6.7 | 3.7 |
| 5-HT1B | 11.8 | 1.2 |
| BZP Rat Brain Site | 5.3 | 1.3 |
| 5-HT3 | −1.7 | 5.8 |
| 5-ht5a | −17.7 | 4.8 |
| H1 | 1.1 | 8.5 |
| H2 | 41.1 | 14.2 |
| DAT | 1.5 | 8.7 |
| SERT | 75.8 | 4.2 | human TrpA1 polypeptide NCBI Ref: NP_015628.2
SEQ ID NO: 01

```
  1 mkrslrkmwr pgekkepqgv vyedvpddte dfkeslkvvf
    egsayglqnf nkqkklkrcd 61 dmdtfflhya aaegqielme kitrdsslev lhemddygnt
    plhcaveknq iesvkfllsr 121 ganpnlrnfn mmaplhiavq gmnnevmkvl lehrtidvnl
    egengntavi iacttnnsea 181 lqillkkgak pcksnkwgcf pihqaafsgs kecmeiilrf
    geehgysrql hinfmnngka 241 tplhlavqng dlemikmcld ngaqidpvek grctaihfaa
    tqgateivkl missysgsvd 301 ivnttdgche tmlhraslfd hheladylis vgadinkids
    egrsplilat asaswnivnl 361 llskgaqvdi kdnfgrnflh ltvqqpyglk nlrpefmqmq
    qikelvmded ndgctplhya 421 crqggpgsvn nllgfnvsih skskdkkspl hfaasygrin
    tcqrllqdis dtrllnegdl 481 hgmtplhlaa knghdkvvql llkkgalfls dhngwtalhh
    asmggytqtm kvildtnlkc 541 tdrldedgnt alhfaaregh akavalllsh nadivlnkqq
    asflhlalhn krkevvltii 601 rskrwdeclk ifshnspgnk cpitemieyl pecmkvlldf
    cmlhstedks crdyyieynf 661 kylqcpleft kktptqdviy epltalnamv qnnriellnh
    pvckeyllmk wlaygfrahm 721 mnlgsyclgl ipmtilvvni kpgmafnstg iinetsdhse
    ildttnsyli ktcmilvfls 781 sifgyckeag qifqqkrnyf mdisnvlewi iyttgiifvl
    plfveipahl qwqcgaiavy 841 fywmnfllyl qrfencgifi vmlevilktl lrstvvfifl
    llafglsfyi llnlqdpfss 901 pllsiiqtfs mmlgdinyre sflepylrne lahpvlsfaq
    lvsftifvpi vlmnlligla
```

```
 961 vgdiaevqkh aslkriamqv elhtslekkl plwflrkvdq
     kstivypnkp rsggmlfhif 1021 cflfctgeir qeipnadksl emeilkqkyr lkdltfllek
     qhelikliiq kmeiiseted 1081 ddshcsfqdr fkkeqmeqrn srwntvlrav kakthhlep human TrpA1 mRNA NCBI Ref: NM_007332.2
                                          SEQ ID NO: 02
   1 ccagaagttc tccagggctt ccgcagagcg acttttcgc
     tgcctgtgag ctgcagcgcg 61 ggagagctcg ggctcgcgcg gaccccagcg cctggcaggc
     tgacagcgct ctctcgcccc 121 aggtgcccgc gcgcgtggtg agcagctgca ccaggtggcg
     tccggggtgg ggtcaatgaa 181 gcgcagcctg aggaagatgt ggcgccctgg agaaaagaag
     gagccccagg gcgttgtcta 241 tgaggatgtg ccggacgaca cggaggattt caaggaatcg
     cttaaggtgg ttttgaagg 301 aagtgcatat ggattacaaa actttaataa gcaaaagaaa
     ttaaaaagat gtgacgatat 361 ggacaccttc ttcttgcatt atgctgcagc agaaggccaa
     attgagctaa tggagaagat 421 caccagagat tcctctttgg aagtgctgca tgaaatggat
     gattatgaa ataccctct 481 gcattgtgct gtagaaaaa accaaattga aagcgttaag
     tttcttctca gcagaggagc 541 aaacccaaat ctccgaaact tcaacatgat ggctcctctc
     cacatagctg tgcagggcat 601 gaataatgag gtgatgaagg tcttgcttga gcatagaact
     attgatgtta atttggaagg 661 agaaaatgga acacagctg tgatcattgc gtgcaccaca
     aataatagcg aagcattgca 721 gattttgctt aaaaaaggag ctaagccatg taaatcaaat
     aaatggggat gtttccctat 781 tcaccaagct gcattttcag gttccaaaga atgcatggaa
     ataatactaa ggtttggtga 841 agagcatggg tacagtagac agttgcacat taactttatg
     aataatggga aagccacccc 901 tctccacctg gctgtgcaaa atggtgactt ggaaatgatc
     aaaatgtgcc tggacaatgg 961 tgcacaaata gacccagtgg agaagggaag gtgcacagcc
     attcattttg ctgccaccca 1021 gggagccact gagattgtta aactgatgat atcgtcctat
     tctggtagcg tggatattgt 1081 taacacaacc gatggatgtc atgagaccat gcttcacaga
     gcttcattgt ttgatcacca 1141 tgagctagca gactatttaa tttcagtggg agcagatatt
     aataagatcg attctgaagg 1201 acgctctcca cttatattag caactgcttc tgcatcttgg
     aatattgtaa atttgctact 1261 ctctaaaggt gcccaagtag acataaaaga taattttgga
     cgtaattttc tgcatttaac 1321 tgtacagcaa ccttatggat taaaaaatct gcgacctgaa
     tttatgcaga tgcaacagat
```

```
1381 caaagagctg gtaatggatg aagacaacga tgggtgtact
     cctctacatt atgcatgtag 1441 acaggggggc cctggttctg taaataacct acttggcttt
     aatgtgtcca ttcattccaa 1501 aagcaaagat aagaaatcac ctctgcattt tgcagccagt
     tatgggcgta tcaatacctg 1561 tcagaggctc ctacaagaca taagtgatac gaggcttctg
     aatgaaggtg accttcatgg 1621 aatgactcct ctccatctgg cagcaaagaa tggacatgat
     aaagtagttc agcttcttct 1681 gaaaaaaggt gcattgtttc tcagtgacca caatggctgg
     acagctttgc atcatgcgtc 1741 catgggcggg tacactcaga ccatgaaggt cattcttgat
     actaatttga agtgcacaga 1801 tcgcctggat gaagacggga acactgcact tcactttgct
     gcaagggaag gccacgccaa 1861 agccgttgcg cttcttctga gccacaatgc tgacatagtc
     ctgaacaagc agcaggcctc 1921 cttttttgcac cttgcacttc acaataagag gaaggaggtt
     gttcttacga tcatcaggag 1981 caaaagatgg gatgaatgtc ttaagatttt cagtcataat
     tctccaggca ataaatgtcc 2041 aattacagaa atgatagaat acctccctga atgcatgaag
     gtactttag atttctgcat 2101 gttgcattcc acagaagaca gtcctgccg agactattat
     atcgagtata atttcaaata 2161 tctttcaatgt ccattagaat tcaccaaaaa aacacctaca
     caggatgtta tatatgaacc 2221 gcttacagcc ctcaacgcaa tggtacaaaa taaccgcata
     gagcttctca atcatcctgt 2281 gtgtaaagaa tatttactca tgaaatggtt ggcttatgga
     tttagagctc atatgatgaa 2341 tttaggatct tactgtcttg gtctcatacc tatgaccatt
     ctcgttgtca atataaaacc 2401 aggaatggct ttcaactcaa ctggcatcat caatgaaact
     agtgatcatt cagaaatact 2461 agataccacg aattcatatc taataaaaac ttgtatgatt
     ttagtgtttt tatcaagtat 2521 atttgggtat tgcaaagaag cggggcaaat tttccaacag
     aaaaggaatt attttatgga 2581 tataagcaat gttcttgaat ggattatcta acgacgggc
     atcatttttg tgctgccctt 2641 gtttgttgaa ataccagctc atctgcagtg caatgtgga
     gcaattgctg tttacttcta 2701 ttggatgaat ttcttattgt atcttcaaag atttgaaaat
     tgtggaattt ttattgttat 2761 gttggaggta attttgaaaa ctttgttgag gtctacagtt
     gtattatct tccttcttct 2821 ggcttttgga ctcagctttt acatcctcct gaatttacag
     gatccctcta gtctccatt 2881 gctttctata atccagacct tcagcatgat gctaggagat
     atcaattatc gagagtcctt 2941 cctagaacca tatctgagaa atgaattggc acatccagtt
     ctgtcctttg cacaacttgt
```

-continued

```
3001 ttccttcaca atatttgtcc caattgtcct catgaattta
     cttattggtt tggcagttgg 3061 cgacattgct gaggtccaga acatgcatc attgaagagg
     atagctatgc aggtggaact 3121 tcataccagc ttagagaaga agctgccact ttggtttcta
     cgcaaagtgg atcagaaatc 3181 caccatcgtg tatcccaaca aacccagatc tggtgggatg
     ttattccata tattctgttt 3241 tttattttgc actggggaaa taagacaaga aataccaaat
     gctgataaat ctttagaaat 3301 ggaaatatta aagcagaaat accggctgaa ggatcttact
     tttctcctgg aaaaacagca 3361 tgagctcatt aaactgatca ttcagaagat ggagatcatc
     tctgagacag aggatgatga 3421 tagccattgt tcttttcaag acaggtttaa gaaagagcag
     atggaacaaa ggaatagcag 3481 atggaatact gtgttgagag cagtcaaggc aaaaacacac
     catcttgagc cttagctcct 3541 cagaccttca gtgaggcttc taatgggggg tgcatgactt
     gctggttcta actttcaatt 3601 taaaaagagt gaggaagaag cagaatgatt cattttgctg
     cgtgtgaaat catggttcct 3661 gcatgctgta taaaagtaaa ccatcttttta tcctctattc
     atattttcta ccaatcacta 3721 tgtattgggg atatctttgc agatatgttc aaattggact
     ggactttgat gagatataat 3781 ctcattattt gaatgggtag aaaatgaatt tgctagaaca
     cacattttta atgaaaagaa 3841 gtaataaatg taactattaa gctaaaatgc aaatgtcagt
     actgaattcc tgcttgttaa 3901 ttacataata tgtgatgctc tagaaaatag tcacaagtat
     taataatgcc ttagatgata 3961 gtcttaaata ttaggttgag gtctacctaa cctaagctgc
     ttcctggaaa gcttcatgtt 4021 gaaagaacct atgggtggca ccatgtggac ttttctgtcc
     ctactgtgat gaatagcccc 4081 acccttcttg ctgtccccaa cacacctgat gtcactttga
     gccatatagt tgaagtacaa 4141 attaataggc cttatgatat gcacgaattt tactatagat
     aatatatgtt gtttctggtt 4201 ttgtttgcca atgagcataa taaatgtaaa acctatatag
     tatccctgtg attattgtat 4261 gagcctttgt ttgagatttg aaaacaacat ggctccatca
     catattccct ttttttcttt 4321 gatgtctact caaatcatga attaatcaca tacctcatca
     ttaatctttt caaggtcctt 4381 ctattgtttt gtctgatttt ctccatcatc ctgattagca
     tgtttattcc ctcactaccc 4441 ccaggagata ttcactgtaa tgaatatgtc tttggctatg
     tatgtgtcct tgtgttatgt 4501 tgtacagtgt tgttttgagt ctgttattat ttacacagat
     gttattatgc tatagcttct 4561 atttctgttt ttgcttctta tttctcttat aattctcact
     tatttcctat tttttctact 4621 catttctatt tgttactcct ttttactgga catgatgttt
     acaagataca actgtgttac 4681 tgtattccat ctagtacggg gcctttggtg tggcttacta
     tttcattgtg tgcacccacc 4741 cacccaccac actggacttt tctagagatg gacagcttgg
     ttacctccac cttcctgcac 4801 tcattctcaa acatactgat gttcatacaa accagcagag
     tgctgaggga cgatatgtac 4861 tattacaaaa ccagacactt ttacattcat ggtccaacag
     atcacatggc ctagaggcaa 4921 tgttgcatat accttaatct ttgatatgaa taatatcttt
     gttctttata tttcttaaaa 4981 cagaaagggt ggaaaatcac tatacagaag caatatccaa
     agatctcctg atcataaaga 5041 caaggggtct tttcagtctt ccctctcctc aaaccttgtg
     tagcattgca caatatagat 5101 ctcagtcaac attcactgag tgccaagaat gtgagaaaca
     ctgtaccatg cctgtcatgc 5161 gaaatattta aataaacaga ttgtcttaca
```

What is claimed herein is:

1. A method of modulating the activity of a neuron, the method comprising;
   a) contacting the neuron with a compound of formula Ia or Ib:

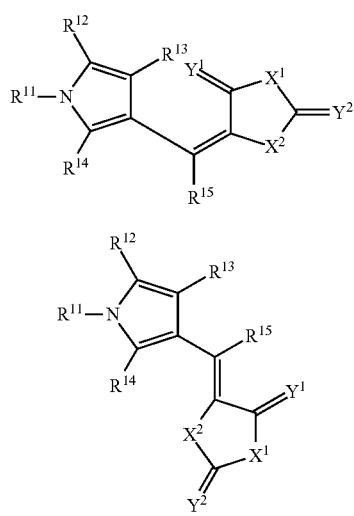

wherein R$^{11}$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)R$^B$; —CO$_2$R$^B$; or —C(R$^B$)$_3$; wherein each occurrence of R$^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

R$^{12}$, R$^{13}$, and R$^{14}$, are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)R$^B$; —CO$_2$R$^B$; -; —CN; —SCN; —SR$^B$; —SOR$^B$; —SO$_2$R$^B$; —NO$_2$; —N(R$^B$)$_2$; —NHC(O)R$^B$; or —C(R$^B$)$_3$; wherein each occurrence of R$^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

R$^{15}$ is hydrogen;
Y$^1$ is O;
Y$^2$ is S;
X$^1$ is NH;
X$^2$ is NH or S; and b) exposing the neuron to electromagnetic radiation comprising a wavelength of from about 300 nm to about 700 nm.

2. The method of claim 1, wherein only neurons contacted with the compound and exposed to the electromagnetic radiation are activated.

3. The method of claim 1, wherein the activity of the neuron is increased.

4. The method of claim 1, wherein the functional output of the neuron is decreased.

5. The method of claim 1, wherein the neuron is functionally ablated.

6. The method of claim 1, wherein the neuron is ablated.

7. The method of claim 1, wherein the neuron is a neuron of a subject in need of treatment for pain or inflammation.

8. The method of claim 7, wherein the pain is neuropathic.

9. The method of claim 1, wherein the subject has a spinal cord injury.

10. A method of performing deep brain stimulation, the method comprising:
    a) contacting a neuron in the brain with a compound of formula Ia or Ib:

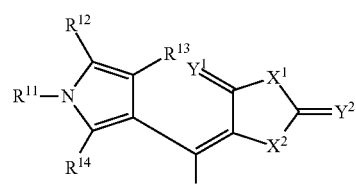

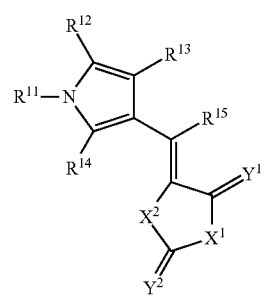

wherein R$^{11}$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)R$^B$; —CO$_2$R$^B$; or —C(R$^B$)$_3$; wherein each occurrence of R$^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

R$^{12}$, R$^{13}$, and R$^{14}$, are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)R$^B$; —CO$_2$R$^B$; -; —CN; —SCN; —SR$^B$; —SOR$^B$; —SO$_2$R$^B$; —NO$_2$; —N(R$^B$)$_2$; —NHC(O)R$^B$; or —C(R$^B$)$_3$; wherein each occurrence of R$^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$R^{15}$ is hydrogen;

$Y^1$ is O;

$Y^2$ is S;

$X^1$ is NH;

$X^2$ is NH or S; and b) exposing the neuron to electromagnetic radiation comprising a wavelength of from about 300 nm to about 700 nm.

11. The method of claim 1, wherein the compound is selected from the group consisting of:

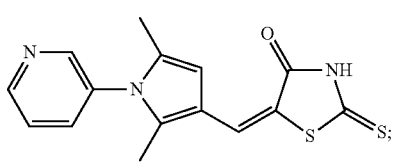

Formula III

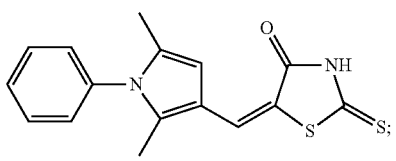

Formula IV

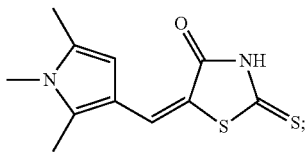

Formula V

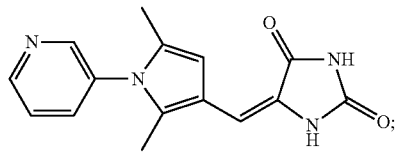

Formula VI

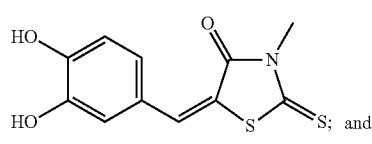

Formula VII

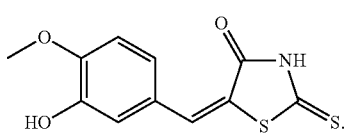

Formula VIII

12. The method of claim 1, wherein the electromagnetic radiation comprises a wavelength of from about 360 nm to about 450 nm.

13. The method of claim 1, wherein the neuron comprises at least one TrpA1 channel.

14. The method of claim 1, wherein $R^{13}$ is hydrogen; and wherein $R^{12}$ and $R^{14}$ are methyl.

15. The method of claim 1, wherein $R^{11}$ is selected from methyl;

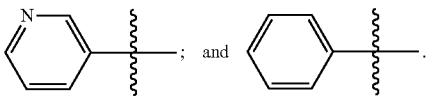

* * * * *